US007524948B2

(12) United States Patent
Keetman et al.

(10) Patent No.: US 7,524,948 B2
(45) Date of Patent: Apr. 28, 2009

(54) EXPRESSION CASSETTES FOR VASCULAR TISSUE-PREFERENTIAL EXPRESSION IN PLANTS

(75) Inventors: Ulrich Keetman, Quedlinburg (DE); Karin Herbers, Neustadt (DE); Helke Hillebrand, Mannheim (DE)

(73) Assignee: SunGene GmbH (DE)

( * ) Notice: Subject to any disclaimer, the term of this patent is extended or adjusted under 35 U.S.C. 154(b) by 57 days.

(21) Appl. No.: 11/296,444

(22) Filed: Dec. 7, 2005

(65) Prior Publication Data

US 2006/0162025 A1    Jul. 20, 2006

(30) Foreign Application Priority Data

| Dec. 8, 2004 | (EP) | ................................. 04029025 |
| Feb. 3, 2005 | (EP) | ................................. 05002263 |
| Feb. 11, 2005 | (EP) | ................................. 05002854 |

(51) Int. Cl.
*C12N 15/82* (2006.01)
*C07H 21/04* (2006.01)
*C12N 15/63* (2006.01)
*A01H 5/00* (2006.01)

(52) U.S. Cl. ..................... 536/24.1; 536/24.3; 435/419; 435/320.1; 800/278; 800/298

(58) Field of Classification Search ........................ None
See application file for complete search history.

(56) References Cited

U.S. PATENT DOCUMENTS 6,797,859 B2 * 9/2004 Abbitt et al. ................. 800/287

FOREIGN PATENT DOCUMENTS

| WO | WO-97/41152 A1 | 11/1997 |
| WO | WO-01/98480 A2 | 12/2001 |
| WO | WO-2004/048595 A2 | 6/2004 |

OTHER PUBLICATIONS

Kim et al 1994, Plant Molecular Biology 24:105-117.*
Donald et al 1990, EMBO J. 9:1717-1726.*
Dolferus et al 1994, Plant Physiology 105: 1075-1087.*
Liu, Z.-Z., et al., "The promoter of a rice glycine-rich protien gene, *Osgrp-2*, confers vascular-specific expression in transgenic plants", Planta, vol. 216 (2003), pp. 824-833.
Chaves, M. M., et al., "Mechanisms underlying plant resilience to water deficits: prospects for water-saving agriculture", Journal of Experimental Botany, vol. 55, No. 407 (2004), pp. 2365-2384.
DeCroocq, V. et al., "Elaborating Cell-Specific Resistance to Plum Pox Potyvirus", Proc. 18th Ins. Symp. on Fruit Tree Virus Diseases, Acta Hort., vol. 550, No. 2 (2001), pp. 397-403.
Gittins, J. R., et al., "Transgene expression in the vegetative tissues of apple driven by the vascular-specific roIC and CoYMV promoters", Transgenic Research, vol. 12 (2003), pp. 391-402.
Ramos, P. L., et al., "Identification of the minimal sequence required for vascular-specific activity of Tomato mottle Taino virus Replication-associated protein promoter in transgenic plants", Virus Research, 102 (2004), pp. 125-132.
Sobeih, W. Y., et al., "Long-distance signals regulating stomatal conductance and leaf growth in tomato (*Lycopersicon esculentum*) plants subjected to partial root-zone drying", Journal of Experimental Botany, vol. 55, No. 407 (2004), pp. 2353-2363.
"*Arabidopsis thaliana* DNA binding AT4G00940 mRNA, complete cds.", GenBank Accession No. NM_116321, Feb. 17, 2004.
"Unknown protein [*Arabidopsis thaliana* ]", GenBank Accession No. NP_191925, Nov. 4, 2005.
"Rhodopsin-like receptor [*Arabidopsis thaliana*]", GenBank Accession No. NP_568642, Nov. 4, 2005.
"Unknown protein [*Arabidoposis thaliana*]", GenBank Accession No. NP_564929, Nov. 4, 2005.
"ATP binding / kinase/ protein serine/threonine kinase [*Arabidopsis thaliana*]", GenBank Accession No. NP_201529, Nov. 4, 2005.
"*Arabidopsis thaliana*rhodopsin-like receptor AT5G45350 mRNA, complete cds.", GenBank Accession No. NM_123903, May 13, 2003.
"*Arabidopsis thaliana*zinc ion binding AT2G39830 mRNA, complete cds.", GenBank Accession No. NM_129542, Feb. 17, 2004.
"*Arabidopsis thaliana* unknown protein At1G68430 mRNA, complete cds.", GenBank Accession No. NM_105514, May 13, 2003.
"*Arabidopsis thaliana*ATP binding / kinase/ protein serine/threonine kinase AT5G67280 mRNA, complete cds.", GenBank Accession No. NM_126128, Feb. 17, 2004.
"Zinc ion binding [*Arabidopsis thaliana*]", GenBank Accession No. NP_181513, Feb. 17, 2004.
"F6N15.19 protein (Hypothetical protein At4g00140)", Nov. 1, 1998, Accession No. 081315.
Dietrich, D., Et Al., "AtPTR1, a plasma membrane peptide transporter expressed during seed germination and in vascular tissue of *Arabidopsis*", The Plant Journal, 2004, vol. 40, pp. 488-499.
Ziegler, C., Et Al., "Regulation of promoter activity of ferredoxin-dependent glutamate synthase", Plant Physiology and Biochemistry, 2003, vol. 41, pp. 649-655.

* cited by examiner

*Primary Examiner*—Russell Kallis
*Assistant Examiner*—Brent Page
(74) *Attorney, Agent, or Firm*—Connolly Bove Lodge & Hutz LLP

(57) ABSTRACT

The present invention relates to expression cassettes comprising transcription regulating sequences with vascular tissue-preferential or vascular tissue-specific expression profiles in plants obtainable from *Arabidopsis thaliana* genes At4g00140, At5g45350, At2g39830, At1g68430, or At5g67280.

14 Claims, No Drawings

EXPRESSION CASSETTES FOR VASCULAR TISSUE-PREFERENTIAL EXPRESSION IN PLANTS

RELATED APPLICATIONS

This application claims benefit to European Application 04029025.6 filed Dec. 8, 2004, European Application 05002263.1 filed Feb. 3, 2005, and European Application 05002854.7 filed Feb. 11, 2005.

FIELD OF THE INVENTION

The present invention relates to expression cassettes comprising transcription regulating nucleotide sequences with vascular tissue-preferential or vascular tissue-specific expression profiles in plants obtainable from *Arabidopsis thaliana* genes At4g00140, At5g45350, At2g39830, At1g68430, or At5g67280.

BACKGROUND OF THE INVENTION

Manipulation of plants to alter and/or improve phenotypic characteristics (such as productivity or quality) requires the expression of heterologous genes in plant tissues. Such genetic manipulation relies on the availability of a means to drive and to control gene expression as required. For example, genetic manipulation relies on the availability and use of suitable promoters which are effective in plants and which regulate gene expression so as to give the desired effect(s) in the transgenic plant.

The vascular tissue-preferential or vascular tissue-specific promoters are useful for improving the transport capacities within a plant. The number of promoters which are capable to regulate expression in vascular tissue is limited (see e.g., WO2004048595; Gittins 2003; Liu ZZ 2003; Ramos 2004).

There is, therefore, a great need in the art for the identification of novel sequences that can be used for expression of selected transgenes in economically important plants. It is thus an objective of the present invention to provide new and alternative expression cassettes for vascular tissue-preferential or vascular tissue-specific expression of transgenes in plants. The objective is solved by the present invention.

SUMMARY OF THE INVENTION

Accordingly, a first embodiment of the invention relates to an expression cassette for vascular tissue-specific or vascular tissue-preferential transcription of an operatively linked nucleic acid sequence in plants comprising
i) at least one transcription regulating nucleotide sequence of a plant gene, said plant gene selected from the group of genes described by the GenBank *Arabidopsis thaliana* genome loci At4g00140, At5g45350, At2g39830, At1g68430, or At5g67280, or a functional equivalent thereof, and functionally linked thereto
ii) at least one nucleic acid sequence which is heterologous in relation to said transcription regulating nucleotide sequence.

Preferably, the transcription regulating nucleotide sequence (or the functional equivalent thereof) is selected from the group of sequences consisting of
i) the sequences described by SEQ ID NOs: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, and 45;
ii) a fragment of at least 50 consecutive bases of a sequence under i) which has substantially the same promoter activity as the corresponding transcription regulating nucleotide sequence described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45;
iii) a nucleotide sequence having substantial similarity (e.g., with a sequence identity of at least 40, 50, 60, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99%) to a transcription regulating nucleotide sequence described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45;
iv) a nucleotide sequence capable of hybridizing (preferably under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a transcription regulating nucleotide sequence described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45, or the complement thereof;
v) a nucleotide sequence capable of hybridizing (preferably under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a nucleic acid comprising 50 to 200 or more consecutive nucleotides of a transcription regulating nucleotide sequence described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, and 45 or the complement thereof;
vi) a nucleotide sequence which is the complement or reverse complement of any of the previously mentioned nucleotide sequences under i) to v).

The functional equivalent of the transcription regulating nucleotide sequence is obtained or obtainable from plant genomic DNA from a gene encoding a polypeptide which has at least 70% amino acid sequence identity to a polypeptide selected from the group described by SEQ ID NO: 7, 17, 27, 37, and 47, respectively.

The expression cassette may be employed for numerous expression purposes such as for example expression of a protein, or expression of a antisense RNA, sense or double-stranded RNA. Preferably, expression of the nucleic acid sequence confers to the plant an agronomically valuable trait.

Other embodiments of the invention relate to vectors comprising an expression cassette of the invention, and transgenic host cell or non-human organism comprising an expression cassette or a vector of the invention. Preferably the organism is a plant.

Another embodiment of the invention relates to a method for identifying and/or isolating a sequence with vascular tissue-specific or vascular tissue-preferential transcription regulating activity characterized that said identification and/or isolation utilizes a nucleic acid sequence encoding a amino acid sequence as described by SEQ ID NO: 7, 17, 27, 37, or 47 or a part of at least 15 bases thereof. Preferably the nucleic acid sequences is described by SEQ ID NO: 6, 16, 26, 36, or 46 or a part of at least 15 bases thereof. More preferably, identification and/or isolation is realized by a method selected from polymerase chain reaction, hybridization, and database screening.

Another embodiment of the invention relates to a method for providing a transgenic expression cassette for vascular tissue-specific or vascular tissue-preferential expression comprising the steps of:

I. isolating of a vascular tissue-preferential or vascular tissue-specific transcription regulating nucleotide sequence utilizing at least one nucleic acid sequence or a part thereof, wherein said sequence is encoding a polypeptide described by SEQ ID NO: 7, 17, 27, 37, or 47, or a part of at least 15 bases thereof, and II. functionally linking said vascular tissue-preferential vascular tissue-specific transcription regulating nucleotide sequence to another nucleotide sequence of interest, which is heterologous in relation to said vascular tissue-preferential or vascular tissue-specific transcription regulating nucleotide sequence.

Definitions

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 per-cent up or down (higher or lower).

As used herein, the word "or" means any one member of a particular list and also includes any combination of members of that list.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

The term "native" or "wild type" gene refers to a gene that is present in the genome of an untransformed cell, i.e., a cell not having a known mutation.

A "marker gene" encodes a selectable or screenable trait.

The term "chimeric gene" refers to any gene that contains

1) DNA sequences, including regulatory and coding sequences, that are not found together in nature, or
2) sequences encoding parts of proteins not naturally adjoined, or
3) parts of promoters that are not naturally adjoined.

Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

An "oligonucleotide" corresponding to a nucleotide sequence of the invention, e.g., for use in probing or amplification reactions, may be about 30 or fewer nucleotides in length (e.g., 9, 12, 15, 18, 20, 21 or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

The terms "protein," "peptide" and "polypeptide" are used interchangeably herein.

The nucleotide sequences of the invention can be introduced into any plant. The genes to be introduced can be conveniently used in expression cassettes for introduction and expression in any plant of interest. Such expression cassettes will comprise the transcriptional initiation region of the invention linked to a nucleotide sequence of interest. Preferred promoters include constitutive, tissue-specific, developmental-specific, inducible and/or viral promoters, most preferred are the vascular tissue-specific or vascular tissue-preferential promoters of the invention. Such an expression cassette is provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions (see also, Guerineau 1991; Proudfoot 1991; Sanfacon 1991; Mogen 1990; Munroe 1990; Ballas 1989; Joshi 1987).

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Transcription regulating nucleotide sequence", transcription regulating nucleotide sequence "regulatory sequences", and "suitable regulatory sequences", each refer to nucleotide sequences influencing the transcription, RNA processing or stability, or translation of the associated (or functionally linked) nucleotide sequence to be transcribed. The transcription regulating nucleotide sequence may have various localizations with the respect to the nucleotide sequences to be transcribed. The transcription regulating nucleotide sequence may be located upstream (5' non-coding sequences), within, or downstream (3' noncoding sequences) of the sequence to be transcribed (e.g., a coding sequence). The transcription regulating nucleotide sequences may be selected from the group comprising enhancers, promoters, translation leader sequences, introns, 5'-untranslated sequences, 3'-untranslated sequences, and polyadenylation signal sequences. They include natural and synthetic sequences as well as sequences, which may be a combination of synthetic and natural sequences. As is noted above, the term "transcription regulating nucleotide sequence" is not limited to promoters. However, preferably a transcription regulating nucleotide sequence of the invention comprises at least one promoter sequence (e.g., a sequence localized upstream of the transcription start of a gene capable to induce transcription of the downstream sequences). In one preferred embodiment the transcription regulating nucleotide sequence of the invention comprises the promoter sequence of the corresponding gene and—optionally and preferably—the native 5'-untranslated region of said gene. Furthermore, the 3'-untranslated region and/or the polyadenylation region of said gene may also be employed.

"5'non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner 1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

The term "transit peptide" as used herein refers part of a expressed polypeptide (preferably to the amino terminal extension of a polypeptide), which is translated in conjunction with the polypeptide forming a precursor peptide and which is required for its entrance into a cell organelle (such as the plastids (e.g., chloroplasts) or mitochondria). The term "transit sequence" refers to a nucleotide sequence that encodes the transit peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant.

Each of the transcription-activating elements do not exhibit an absolute tissue-specificity, but mediate transcriptional activation in most plant parts at a level of at least 1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Inducible promoter" refers to those regulated promoters that can be turned on in one or more cell types by an external stimulus, such as a chemical, light, hormone, stress, or a pathogen.

"Operably-linked" or "functionally linked" refers preferably to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Specific expression" is the expression of gene products which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

The "expression pattern" of a promoter (with or without enhancer) is the pattern of expression levels which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates.

The rate of degradation can however be considered to proceed at a fixed rate when the transcribed sequences are identical, and thus this value can serve as a measure of synthesis rates. When promoters are compared in this way techniques available to those skilled in the art are hybridization S1-RNAse analysis, northern blots and competitive RT-PCR. This list of techniques in no way represents all available techniques, but rather describes commonly used procedures used to analyze transcription activity and expression levels of mRNA.

The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription. A commonly used procedure to analyze expression patterns and levels is through determination of the 'steady state' level of protein accumulation in a cell. Commonly used candidates for the reporter gene, known to those skilled in the art are beta-glucuronidase (GUS), chloramphenicol acetyl transferase (CAT) and proteins with fluorescent properties, such as green fluorescent protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression.

Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

"Overexpression" refers to the level of expression in transgenic cells or organisms that exceeds levels of expression in normal or untransformed (non-transgenic) cells or organisms.

"Antisense inhibition" refers to the production of antisense RNA transcripts capable of suppressing the expression of protein from an endogenous gene or a transgene.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes (English 1996). Gene silencing includes virus-induced gene silencing (Ruiz et al. 1998).

The terms "heterologous DNA sequence," "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Homologous to" in the context of nucleotide sequence identity refers to the similarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

The term "substantially similar" refers to nucleotide and amino acid sequences that represent functional and/or structural equivalents of *Arabidopsis* sequences disclosed herein.

In its broadest sense, the term "substantially similar" when used herein with respect to a nucleotide sequence means that the nucleotide sequence is part of a gene which encodes a polypeptide having substantially the same structure and function as a polypeptide encoded by a gene for the reference nucleotide sequence, e.g., the nucleotide sequence comprises a promoter from a gene that is the ortholog of the gene corresponding to the reference nucleotide sequence, as well as promoter sequences that are structurally related the promoter sequences particularly exemplified herein, i.e., the substantially similar promoter sequences hybridize to the complement of the promoter sequences exemplified herein under high or very high stringency conditions. For example, altered nucleotide sequences which simply reflect the degeneracy of the genetic code but nonetheless encode amino acid sequences that are identical to a particular amino acid sequence are substantially similar to the particular sequences. The term "substantially similar" also includes nucleotide sequences wherein the sequence has been modified, for example, to optimize expression in particular cells, as well as nucleotide sequences encoding a variant polypeptide having one or more amino acid substitutions relative to the (unmodified) polypeptide encoded by the reference sequence, which substitution(s) does not alter the activity of the variant polypeptide relative to the unmodified polypeptide.

In its broadest sense, the term "substantially similar" when used herein with respect to polypeptide means that the polypeptide has substantially the same structure and function as the reference polypeptide. In addition, amino acid sequences that are substantially similar to a particular sequence are those wherein overall amino acid identity is at least 65% or greater to the instant sequences. Modifications that result in equivalent nucleotide or amino acid sequences are well within the routine skill in the art. The percentage of amino acid sequence identity between the substantially similar and the reference polypeptide is at least 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99%, wherein the reference polypeptide is an *Arabidopsis* polypeptide encoded by a gene with a promoter having any one of SEQ ID NOs: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45, a nucleotide sequence comprising an open reading frame having any one of SEQ ID NOs: 6, 16, 26, 36, or 46 which encodes one of SEQ ID NOs: 7, 17, 27, 37, or 47. One indication that two polypeptides are substantially similar to each other, besides having substantially the same function, is that an agent, e.g., an antibody, which specifically binds to one of the polypeptides, also specifically binds to the other.

Sequence comparisons maybe carried out using a Smith-Waterman sequence alignment algorithm (see e.g., Waterman (1995)). The localS program, version 1.16, is preferably used with following parameters: match: 1, mismatch penalty: 0.33, open-gap penalty: 2, extended-gap penalty: 2.

Moreover, a nucleotide sequence that is "substantially similar" to a reference nucleotide sequence is said to be "equivalent" to the reference nucleotide sequence. The skilled artisan recognizes that equivalent nucleotide sequences encompassed by this invention can also be defined by their ability to hybridize, under low, moderate and/or stringent conditions (e.g., 0.1×SSC, 0.1% SDS, 65° C.), with the nucleotide sequences that are within the literal scope of the instant claims.

What is meant by "substantially the same activity" when used in reference to a polynucleotide or polypeptide fragment is that the fragment has at least 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99% of the activity of the full length polynucleotide or full length polypeptide.

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes, and will be under the control of suitable regulatory sequences.

Thus, the regulatory sequences in the target gene may come from any source, including the virus. Target genes may include coding sequences that are either heterologous or homologous to the genes of a particular plant to be transformed. However, target genes do not include native viral genes. Typical target genes include, but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

The term "altered plant trait" means any phenotypic or genotypic change in a transgenic plant relative to the wild-type or non-transgenic plant host.

"Replication gene" refers to a gene encoding a viral replication protein. In addition to the ORF of the replication protein, the replication gene may also contain other overlapping or non-overlapping ORF(s), as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

"Chimeric trans-acting replication gene" refers either to a replication gene in which the coding sequence of a replication protein is under the control of a regulated plant promoter other than that in the native viral replication gene, or a modified native viral replication gene, for example, in which a site specific sequence(s) is inserted in the 5' transcribed but untranslated region. Such chimeric genes also include insertion of the known sites of replication protein binding between the promoter and the transcription start site that attenuate transcription of viral replication protein gene.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include Agrobacterium-mediated transformation (De Blaere 1987) and particle bombardment technology (U.S. Pat. No. 4,945,050). Whole plants may be regenerated from transgenic cells by methods well known to the skilled artisan (see, for example, Fromm 1990).

"Transformed," "transgenic," and "recombinant" refer to a host organism such as a bacterium or a plant into which a heterologous nucleic acid molecule has been introduced. The nucleic acid molecule can be stably integrated into the genome generally known in the art and are disclosed (Sambrook 1989; Innis 1995; Gelfand 1995; Innis & Gelfand 1999. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as Agrobacterium-mediated transformation or biolistic bombardment), but not selected for stable maintenance.

"Stably transformed" refers to cells that have been selected and regenerated on a selection media following transformation.

"Transient expression" refers to expression in cells in which a virus or a transgene is introduced by viral infection or by such methods as Agrobacterium-mediated transformation, electroporation, or biolistic bombardment, but not selected for its stable maintenance.

"Genetically stable" and "heritable" refer to chromosomally-integrated genetic elements that are stably maintained in the plant and stably inherited by progeny through successive generations.

"Primary transformant" and "T0 generation" refer to transgenic plants that are of the same genetic generation as the tissue which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Wild-type" refers to a virus or organism found in nature without any known mutation.

"Genome" refers to the complete genetic material of an organism.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer 1991; Ohtsuka 1985; Rossolini 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals.

The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

The nucleic acid molecules of the invention can be "optimized" for enhanced expression in plants of interest (see, for example, WO 91/16432; Perlak 1991; Murray 1989). In this manner, the open reading frames in genes or gene fragments can be synthesized utilizing plant-preferred codons (see, for example, Campbell & Gowri, 1990 for a discussion of host-preferred codon usage). Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass, sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art (see, for example, Stemmer 1994; Stemmer 1994; Crameri 1997; Moore 1997; Zhang 1997; Crameri 1998; and U.S. Pat. Nos. 5,605,793 and 5,837,458).

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art (see, for example, Kunkel 1985; Kunkel 1987; U.S. Pat. No. 4,873,192; Walker & Gaastra, 1983 and the references cited therein). Guidance as to appropriate amino acid substitutions that do not affect biological activity of the protein of interest may be found in the model of Dayhoff et al. (1978). Conservative substitutions, such as exchanging one amino acid with another having similar properties, are preferred.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to a nucleotide sequence of interest, which is—optionally—operably linked to termination signals and/or other regulatory elements. An expression cassette may also comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. Likewise, a nucleic acid sequence to be expressed may be placed (or inserted) downstream of an endogenous promoter sequence thereby forming an expression cassette. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development (e.g., the vascular tissue-specific or vascular tissue-preferential promoters of the invention).

"Vector" is defined to include, inter alia, any plasmid, cosmid, phage or Agrobacterium binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

A "transgenic plant" is a plant having one or more plant cells that contain an expression vector.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described (Higgins 1988, 1989; Corpet 1988; Huang 1992; Pearson 1994). The ALIGN program is based on the algorithm of Myers and Miller, supra. The BLAST programs of Altschul et al., 1990, are based on the algorithm of Karlin and Altschul, supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments. or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) (i) The term "substantial identity" or "substantial similarity" of polynucleotide sequences means (preferably for a protein encoding sequence) that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. The term "substantial identity" or "substantial similarity" of polynucleotide sequences (preferably for promoter sequence) means (as described above for variants) that a polynucleotide comprises a sequence that has at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984:

$$T_m=81.5° C.+16.6(\log_{10}M)+0.41(\% GC)-0.61(\% \text{form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH. An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C.

"DNA shuffling" is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA preferably encodes a variant polypeptide modified with respect to the polypeptide encoded by the template DNA, and may have an altered biological activity with respect to the polypeptide encoded by the template DNA.

"Recombinant DNA molecule" is a combination of DNA sequences that are joined together using recombinant DNA technology and procedures used to join together DNA sequences as described, for example, in Sambrook et al., 1989.

The word "plant" refers to any plant, particularly to agronomically useful plants (e.g., seed plants), and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ differentiated into a structure that is present at any stage of a plant's development. Such structures include one or more plant organs including, but are not limited to, fruit, shoot, stem, leaf, flower petal, etc. Preferably, the term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same.

The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom. Preferred are plants and plant materials of the following plant families: Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxifragaceae, Scrophulariaceae, Solanaceae, Tetragoniaceae.

Annual, perennial, monocotyledonous and dicotyledonous plants are preferred host organisms for the generation of transgenic plants. The use of the recombination system, or method according to the invention is furthermore advantageous in all ornamental plants, forestry, fruit, or ornamental trees, flowers, cut flowers, shrubs or turf. Said plant may include—but shall not be limited to—bryophytes such as, for example, Hepaticae (hepaticas) and Musci (mosses); pteridophytes such as ferns, horsetail and club-mosses; gymnosperms such as conifers, cycads, ginkgo and Gnetaeae; algae such as Chlorophyceae, Phaeophyceae, Rhodophyceae, Myxophyceae, Xanthophyceae, Bacillariophyceae (diatoms) and Euglenophyceae.

Plants for the purposes of the invention may comprise the families of the Rosaceae such as rose, Ericaceae such as rhododendrons and azaleas, Euphorbiaceae such as poinsettias and *croton*, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geraniums, Liliaceae such as Drachaena, Moraceae such as ficus, Araceae such as philodendron and many others.

The transgenic plants according to the invention are furthermore selected in particular from among dicotyledonous crop plants such as, for example, from the families of the Leguminosae such as pea, alfalfa and soybean; the family of the Umbelliferae, particularly the genus *Daucus* (very particularly the species *carota* (carrot)) and *Apium* (very particularly the species *graveolens* var. *dulce* (celery)) and many others; the family of the Solanaceae, particularly the genus *Lycopersicon*, very particularly the species *esculentum* (tomato) and the genus *Solanum*, very particularly the species *tuberosum* (potato) and *melongena* (aubergine), tobacco and many others; and the genus *Capsicum*, very particularly the species *annum* (pepper) and many others; the family of the Leguminosae, particularly the genus *Glycine*, very particularly the species *max* (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, particularly the genus *Lactuca*, very particularly the species *sativa* (lettuce) and many others.

The transgenic plants according to the invention may be selected among monocotyledonous crop plants, such as, for example, cereals such as wheat, barley, sorghum and millet, rye, triticale, maize, rice or oats, and sugarcane. Further preferred are trees such as apple, pear, quince, plum, cherry, peach, nectarine, apricot, papaya, mango, and other woody species including coniferous and deciduous trees such as poplar, pine, *sequoia*, cedar, oak, etc. Especially preferred are

*Arabidopsis thaliana, Nicotiana tabacum*, oilseed rape, soybean, corn (maize), wheat, linseed, potato and tagetes.

"Significant increase" is an increase that is larger than the margin of error inherent in the measurement technique, preferably an increase by about 2-fold or greater.

"Significantly less" means that the decrease is larger than the margin of error inherent in the measurement technique, preferably a decrease by about 2-fold or greater.

DETAILED DESCRIPTION OF THE INVENTION

The present invention thus provides for isolated nucleic acid molecules comprising a plant nucleotide sequence that directs vascular tissue-preferential or vascular tissue-specific transcription of an operably linked nucleic acid fragment in a plant cell.

Specifically, the present invention provides transgenic expression cassettes for regulating vascular tissue-preferential or vascular tissue-specific expression in plants comprising i) at least one transcription regulating nucleotide sequence of a plant gene, said plant gene selected from the group of genes described by the GenBank *Arabidopsis thaliana* genome locii At4g00140, At5g45350, At2g39830, At1g68430, or At5g67280, or a functional equivalent thereof, and functionally linked thereto ii) at least one nucleic acid sequence which is heterologous in relation to said transcription regulating nucleotide sequence.

The term "vasculature-specific" or "vascular tissue-preferential" in the context of the inventions means a expression in one or more vascular tissue of a plant. Vascular tissue are is the tissue in which long distance transport of water and various dissolved substances is located. Vascular tissue can essentially be divided into phloem and xylem and a cambial region separating both tissue sub-types. Phloem constitutes cells in which photosynthates (i.e. photosynthetic products as e.g. sugars and amino acids, signal molecules, as e.g. hormones and micro RNAs) are transported from their site of production (i.e. source tissue as e.g. fully grown leaves) to their site of storage and consumption (i.e. sink tissue as e.g. flowers, tubers, seeds). This fluid is also referred to as "phloem sap". The transport of solutes in the sieve elements of the phloem is highly dependent on the neighboring companion cells that provide energy to the sieve element cells and also function in loading and unloading solutes into and from the sieve elements, respectively. Xylem vessels consist of fused cells and are surrounded by parenchyma cells. Xylem vessels are instrumental in transporting water and minerals from the root to the shoot, a process that is driven by transpiration of water vapor in the above-ground organs of a plant. Vascular tissue in the context of the invention comprises all of the cell types described afore regardless of different anatomical organization of phloem and xylem in roots, stems/stalks, flowers or leaves. In leaves, vascular bundles of different order are formed during the development. This is also referred to as leave veins of different order.

The vascular tissue-preferential or vascular tissue-specific promoters may be useful for improving the transport capacities within a plant. Promoters specifically active in the vascular tissue of plants could serve in driving effect genes, e.g. encoding transporters, in the phloem involved in loading or unloading solutes. One might manipulate this process in order to make it more efficient or more selective for particular solutes and by this alter storage compound allocation. Promoters active in the xylem might be useful in enhancing water use efficiency of plants (see e.g., Chaves 2004). Furthermore it is known that micro RNAs and other signal molecules (as e.g. hormones) implied in the systemic or directed spread of signals are also transported in the phloem. One might engineer constructs interfering with these processes by using vascular tissue-specific promoters (see e.g., Sobeih 2004). It is also proposed that pathogens as e.g. viruses make use of the vascular system when infecting plants (see e.g., Decroocq 2001). Promoters specifically active in vascular tissue might therefore also be useful in preventing pathogens from systemic spread.

One might combine approaches in which vascular tissue-specific promoters drive certain effect genes with approaches in which root-specific promoters are employed, e.g. in order to enhance nutrient uptake from the soil. By this combinatorial approach uptake into and distribution within the plant might be improved. Another field of application for vascular tissue-specific promoters might be the alteration of fiber composition, structure or content, by driving trait genes coding for e.g. cell wall modifying enzymes possibly involved in lignification. Theses approaches would aim at the improvement of food or feed quality, or at modified fiber characteristics important for industrial applications.

"Vascular tissue-specific transcription" in the context of this invention means the transcription of a nucleic acid sequence by a transcription regulating element in a way that transcription of said nucleic acid sequence in seeds contribute to more than 90%, preferably more than 95%, more preferably more than 99% of the entire quantity of the RNA transcribed from said nucleic acid sequence in the entire plant during any of its developmental stage. All of the transcription regulating nucleotide sequences specified herein (designated pSUK416, pSUK416 GB, pSUK418, pSUK418 GB, pSUK418LGB, pSUK420, pSUK420 GB, pSUK422, pSUK422 GB, pSUK424L, pSUK424LGB, pSUK424S, pSUK424SGB, pSUK426L, pSUK426LGB, pSUK426S, pSUK426SGB, pSUK428L, pSUK428LGB, pSUK428S, pSUK428SGB, pSUK430L, pSUK430LGB, pSUK430S, pSUK430SGB, pSUK436L, pSUK436LGB, pSUK436S, pSUK436SGB, pSUK438L, pSUK438LGB, pSUK438S, pSUK438SGB) are considered to be vascular tissue-specific transcription regulating nucleotide sequences.

"Vascular tissue-preferential transcription" in the context of this invention means the transcription of a nucleic acid sequence by a transcription regulating element in a way that transcription of said nucleic acid sequence in seeds contribute to more than 50%, preferably more than 70%, more preferably more than 80% of the entire quantity of the RNA transcribed from said nucleic acid sequence in the entire plant during any of its developmental stage.

Preferably a transcription regulating nucleotide sequence of the invention comprises at least one promoter sequence of the respective gene (e.g., a sequence localized upstream of the transcription start of the respective gene capable to induce transcription of the downstream sequences). The transcription regulating nucleotide sequence may comprise the promoter sequence of said genes but may further comprise other elements such as the 5'-untranslated sequence, enhancer, introns etc. Preferably, said promoter sequence directs vascular tissue-preferential or vascular tissue-specific transcription of an operably linked nucleic acid segment in a plant or plant cell e.g., a linked plant DNA comprising an open reading frame for a structural or regulatory gene.

The following Table 1 illustrates the genes from which the promoters of the invention are preferably isolated, the function of said genes, the cDNA encoded by said genes, and the protein (ORF) encoded by said genes.

TABLE 1

Genes from which the promoters of the invention are preferably isolated,
putative function of said genes, cDNA and the protein encoded by said genes.

| Gene Locus | Putative function | Promotor SEQ ID | mRNA locus ID cDNA SEQ ID | Proteine ID Protein SEQ ID |
|---|---|---|---|---|
| At4g00140 | encoding *Arabidopsis thaliana* expressed protein | SEQ ID NO: 1,2,3,4,5 | NM_116231 SEQ ID NO: 6 | NP_191925 SEQ ID NO: 7 |
| At5g45350 | encoding *Arabidopsis thaliana* proline-rich family protein | SEQ ID NO: 8,9,10,11,12,13, 14,15 | NM_123903 SEQ ID NO: 16 | NP_568642.1 SEQ ID NO: 17 |
| At2g39830 | encoding LIM domain-containing protein | SEQ ID NO: 18,19,20,21,22, 23,24,25, | NM_129542 SEQ ID NO: 26 | NP_181513 SEQ ID NO: 27 |
| At1g68430 | encoding expressed protein | SEQ ID NO: 28,29,30,31,32, 33,34,35, | NM_105514 SEQ ID NO: 36 | NP_564929 SEQ ID NO: 37 |
| At5g67280 | encoding putative leucine-rich repeat transmembrane protein kinase | SEQ ID NO: 38,39,40,41,42, 43,44,45 | NM_126128 SEQ ID NO: 46 | NP_201529 SEQ ID NO: 47 |

Preferably the transcription regulating nucleotide sequence (or the functional equivalent thereof) is selected from the group of sequences consisting of i) the sequences described by SEQ ID NOs: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, and 45 ii) a fragment of at least 50 consecutive bases of a sequence under i) which has substantially the same promoter activity as the corresponding transcription regulating nucleotide sequence described by 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45;

iii) a nucleotide sequence having substantial similarity (e.g., with a sequence identity of at least 40, 50, 60, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%; 97%, to 98% and 99%) to a transcription regulating nucleotide sequence described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45;

iv) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C. (more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate 20 (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a transcription regulating nucleotide sequence described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45, or the complement thereof;

v) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0. 1% SDS at 50° C. (more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides of a transcription regulating nucleotide sequence described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45, or the complement thereof;

vi) a nucleotide sequence which is the complement or reverse complement of any of the previously mentioned nucleotide sequences under i) to v).

A functional equivalent of the transcription regulating nucleotide sequence can also be obtained or is obtainable from plant genomic DNA from a gene encoding a polypeptide which is substantially similar and preferably has at least 70%, preferably 80%, more preferably 90%, most preferably 95% amino acid sequence identity to a polypeptide encoded by an *Arabidopsis thaliana* gene comprising any one of SEQ ID NOs: 7, 17, 27, 37, or 47, respectively, or a fragment of said transcription regulating nucleotide sequence which exhibits promoter activity in a vascular tissue-preferential or vascular tissue-specific fashion.

The activity of a transcription regulating nucleotide sequence is considered equivalent if transcription is initiated in a vascular tissue-preferential or vascular tissue-specific fashion (as defined above). Such expression profile is preferably demonstrated using reporter genes operably linked to said transcription regulating nucleotide sequence. Preferred reporter genes (Schenborn 1999) in this context are green fluorescence protein (GFP) (Chui 1996; Leffel 1997), chloramphenicol transferase, luciferase (Millar 1992), β-glucuronidase or □-galactosidase. Especially preferred is β-glucuronidase (Jefferson 1987).

Beside this the transcription regulating activity of a function equivalent may vary from the activity of its parent sequence, especially with respect to expression level. The expression level may be higher or lower than the expression level of the parent sequence. Both derivations may be advantageous depending on the nucleic acid sequence of interest to be expressed. Preferred are such functional equivalent sequences which—in comparison with its parent sequence—does not derivate from the expression level of said parent sequence by more than 50%, preferably 25%, more preferably 10% (as to be preferably judged by either mRNA expression or protein (e.g., reporter gene) expression). Furthermore preferred are equivalent sequences which demonstrate an increased expression in comparison to its parent sequence, preferably an increase my at least 50%, more preferably by at least 100%, most preferably by at least 500%.

Preferably functional equivalent of the transcription regulating nucleotide sequence can be obtained or is obtainable from plant genomic DNA from a gene expressing a mRNA described by a cDNA which is substantially similar and preferably has at least 70%, preferably 80%, more preferably 90%, most preferably 95% sequence identity to a sequence described by any one of SEQ ID NOs: 6, 16, 26, 36, or 46, respectively, or a fragment of said transcription regulating nucleotide sequence which exhibits promoter activity in a vascular tissue-preferential or vascular tissue-specific fashion.

Such functional equivalent of the transcription regulating nucleotide sequence may be obtained from other plant species by using the vascular tissue-preferential or vascular tissue-specific *Arabidopsis* promoter sequences described herein as probes to screen for homologous structural genes in other plants by hybridization under low, moderate or stringent hybridization conditions. Regions of the vascular tissue-preferential or vascular tissue-specific promoter sequences of the present invention which are conserved among species could also be used as PCR primers to amplify a segment from a species other than *Arabidopsis*, and that segment used as a hybridization probe (the latter approach permitting higher stringency screening) or in a transcription assay to determine promoter activity. Moreover, the vascular tissue-preferential or vascular tissue-specific promoter sequences could be employed to identify structurally related sequences in a database using computer algorithms.

More specifically, based on the *Arabidopsis* nucleic acid sequences of the present invention, orthologs may be identified or isolated from the genome of any desired organism, preferably from another plant, according to well known techniques based on their sequence similarity to the *Arabidopsis* nucleic acid sequences, e.g., hybridization, PCR or computer generated sequence comparisons. For example, all or a portion of a particular *Arabidopsis* nucleic acid sequence is used as a probe that selectively hybridizes to other gene sequences present in a population of cloned genomic DNA fragments or cDNA fragments (i.e., genomic or cDNA libraries) from a chosen source organism. Further, suitable genomic and cDNA libraries may be prepared from any cell or tissue of an organism. Such techniques include hybridization screening of plated DNA libraries (either plaques or colonies; see, e.g., Sambrook 1989) and amplification by PCR using oligonucleotide primers preferably corresponding to sequence domains conserved among related polypeptide or subsequences of the nucleotide sequences provided herein (see, e.g., Innis 1990). These methods are particularly well suited to the isolation of gene sequences from organisms closely related to the organism from which the probe sequence is derived. The application of these methods using the *Arabidopsis* sequences as probes is well suited for the isolation of gene sequences from any source organism, preferably other plant species. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the sequence of the invention. Methods for preparation of probes for hybridization and for construction of cDNA and genomic libraries are generally known in the art and are disclosed in Sambrook et al. (1989). In general, sequences that hybridize to the sequences disclosed herein will have at least 40% to 50%, about 60% to 70% and even about 80% 85%, 90%, 95% to 98% or more identity with the disclosed sequences. That is, the sequence similarity of sequences may range, sharing at least about 40% to 50%, about 60% to 70%, and even about 80%, 85%, 90%, 95% to 98% sequence similarity.

The nucleic acid molecules of the invention can also be identified by, for example, a search of known databases for genes encoding polypeptides having a specified amino acid sequence identity or DNA having a specified nucleotide sequence identity. Methods of alignment of sequences for comparison are well known in the art and are described hereinabove.

Hence, the isolated nucleic acid molecules of the invention include the orthologs of the *Arabidopsis* sequences disclosed herein, i.e., the corresponding nucleotide sequences in organisms other than *Arabidopsis*, including, but not limited to, plants other than *Arabidopsis*, preferably dicotyledonous plants, e.g., *Brassica napus*, alfalfa, sunflower, soybean, cotton, peanut, tobacco or sugar beet, but also cereal plants such as corn, wheat, rye, turfgrass, sorghum, millet, sugarcane, barley and banana. An orthologous gene is a gene from a different species that encodes a product having the same or similar function, e.g., catalyzing the same reaction as a product encoded by a gene from a reference organism. Thus, an ortholog includes polypeptides having less than, e.g., 65% amino acid sequence identity, but which ortholog encodes a polypeptide having the same or similar function. Databases such GenBank may be employed to identify sequences related to the *Arabidopsis* sequences, e.g., orthologs in other dicotyledonous plants such as *Brassica napus* and others. Alternatively, recombinant DNA techniques such as hybridization or PCR may be employed to identify sequences related to the *Arabidopsis* sequences or to clone the equivalent sequences from different *Arabidopsis* DNAs.

The transcription regulating nucleotide sequences of the invention or their functional equivalents can be obtained or isolated from any plant or non-plant source, or produced synthetically by purely chemical means. Preferred sources include, but are not limited to the plants defined in the DEFINITION section above.

Thus, another embodiment of the invention relates to a method for identifying and/or isolating a sequence with vascular tissue-preferential or vascular tissue-specific transcription regulating activity utilizing a nucleic acid sequence encoding a amino acid sequence as described by SEQ ID NO: 7, 17, 27, 37, or 47 or a part thereof. Preferred are nucleic acid sequences described by SEQ ID NO: 6, 16, 26, 36, or 46 or parts thereof. "Part" in this context means a nucleic acid sequence of at least 15 bases preferably at least 25 bases, more preferably at least 50 bases. The method can be based on (but is not limited to) the methods described above such as polymerase chain reaction, hybridization or database screening. Preferably, this method of the invention is based on a polymerase chain reaction, wherein said nucleic acid sequence or its part is utilized as oligonucleotide primer. The person skilled in the art is aware of several methods to amplify and isolate the promoter of a gene starting from part of its coding sequence (such as, for example, part of a cDNA). Such methods may include but are not limited to method such as inverse PCR ("iPCR") or "thermal asymmetric interlaced PCR" ("TAIL PCR").

Another embodiment of the invention is related to a method for providing a transgenic expression cassette for vascular tissue-preferential or vascular tissue-specific expression comprising the steps of:

I. isolating of a vascular tissue-preferential or vascular tissue-specific transcription regulating nucleotide sequence utilizing at least one nucleic acid sequence or a part thereof, wherein said sequence is encoding a polypeptide described by SEQ ID NO: 7, 17, 27, 37, or 47, or a part of at least 15 bases thereof, and II. functionally linking said vascular tissue-preferential or vascular tissue-specific transcription regulating nucleotide sequence to another nucleotide sequence of interest, which is heterologous in relation to said vascular tissue-preferential or vascular tissue-specific transcription regulating nucleotide sequence.

Preferably, the nucleic acid sequence employed for the isolation comprises at least 15 base, preferably at least 25 bases, more preferably at least 50 bases of a sequence described by SEQ ID NO: 6, 16, 26, 36, or 46. Preferably, the isolation of the vascular tissue-preferential or vascular tissue-specific transcription regulating nucleotide sequence is realized by a polymerase chain reaction utilizing said nucleic acid sequence as a primer. The operable linkage can be realized by standard cloning method known in the art such as ligation-mediated cloning or recombination-mediated cloning.

Preferably, the transcription regulating nucleotide sequences and promoters of the invention include a consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, and 45, or the promoter orthologs thereof, which include the minimal promoter region.

In a particular embodiment of the invention said consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, has at least 75%, preferably 80%, more preferably 90% and most preferably 95%, nucleic acid sequence identity with a corresponding consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, and 45, or the promoter orthologs thereof, which include the minimal promoter region. The above defined stretch of contiguous nucleotides preferably comprises one or more promoter motifs selected from the group consisting of TATA box, GC-box, CAAT-box and a transcription start site.

The transcription regulating nucleotide sequences of the invention or their functional equivalents are capable of driving vascular tissue-preferential or vascular tissue-specific expression of a coding sequence in a target cell, particularly in a plant cell. The promoter sequences and methods disclosed herein are useful in regulating vascular tissue-preferential or vascular tissue-specific expression, respectively, of any heterologous nucleotide sequence in a host plant in order to vary the phenotype of that plant. These promoters can be used with combinations of enhancer, upstream elements, and/or activating sequences from the 5' flanking regions of plant expressible structural genes. Similarly the upstream element can be used in combination with various plant promoter sequences.

The transcription regulating nucleotide sequences and promoters of the invention are useful to modify the phenotype of a plant. Various changes in the phenotype of a transgenic plant are desirable, i.e., modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in an alteration in the phenotype of the transformed plant.

Generally, the transcription regulating nucleotide sequences and promoters of the invention may be employed to express a nucleic acid segment that is operably linked to said promoter such as, for example, an open reading frame, or a portion thereof, an anti-sense sequence, a sequence encoding for a double-stranded RNA sequence, or a transgene in plants.

An operable linkage may—for example—comprise an sequential arrangement of the transcription regulating nucleotide sequence of the invention (for example a sequence as described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45) with a nucleic acid sequence to be expressed, and—optionally—additional regulatory elements such as for example polyadenylation or transcription termination elements, enhancers, introns etc, in a way that the transcription regulating nucleotide sequence can fulfill its function in the process of expression the nucleic acid sequence of interest under the appropriate conditions the term "appropriate conditions" mean preferably the presence of the expression cassette in a plant cell. Preferred are arrangements, in which the nucleic acid sequence of interest to be expressed is placed down-stream (i.e., in 3'-direction) of the transcription regulating nucleotide sequence of the invention in a way, that both sequences are covalently linked. Optionally additional sequences may be inserted in-between the two sequences. Such sequences may be for example linker or multiple cloning sites. Furthermore, sequences can be inserted coding for parts of fusion proteins (in case a fusion protein of the protein encoded by the nucleic acid of interest is intended to be expressed). Preferably, the distance between the nucleic acid sequence of interest to be expressed and the transcription regulating nucleotide sequence of the invention is not more than 200 base pairs, preferably not more than 100 base pairs, more preferably no more than 50 base pairs.

An operable linkage in relation to any expression cassette or of the invention may be realized by various methods known in the art, comprising both in vitro and in vivo procedure. Thus, an expression cassette of the invention or an vector comprising such expression cassette may by realized using standard recombination and cloning techniques well known in the art (see e.g., Maniatis 1989; Silhavy 1984; Ausubel 1987).

An expression cassette may also be assembled by inserting a transcription regulating nucleotide sequence of the invention (for example a sequence as described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45) into the plant genome. Such insertion will result in an operable linkage to a nucleic acid sequence of interest which as such already existed in the genome. By the insertion the nucleic acid of interest is expressed in a vascular tissue-preferential or vascular tissue-specific way due to the transcription regulating properties of the transcription regulating nucleotide sequence. The insertion may be directed or by chance. Preferably the insertion is directed and realized by for example homologous recombination. By this procedure a natural promoter may be exchanged against the transcription regulating nucleotide sequence of the invention, thereby modifying the expression profile of an endogenous gene. The transcription regulating nucleotide sequence may also be inserted in a way, that antisense mRNA of an endogenous gene is expressed, thereby inducing gene silencing.

Similar, a nucleic acid sequence of interest to be expressed may by inserted into a plant genome comprising the transcription regulating nucleotide sequence in its natural genomic environment (i.e. linked to its natural gene) in a way that the inserted sequence becomes operably linked to the transcription regulating nucleotide sequence, thereby forming an expression cassette of the invention.

The open reading frame to be linked to the transcription regulating nucleotide sequence of the invention may be obtained from an insect resistance gene, a disease resistance gene such as, for example, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a positive selectable marker, a gene affecting plant agronomic characteristics, i.e., yield, standability, and the like, or an environment or stress resistance gene, i.e., one or more genes that confer herbicide resistance or tolerance, insect resistance or tolerance, disease resistance or tolerance (viral, bacterial, fungal, oomycete, or nematode), stress tolerance or resistance (as exemplified by resistance or tolerance to drought, heat, chilling, freezing, excessive moisture, salt stress, or oxidative stress), increased yields, food content and makeup, physical appearance, male sterility, drydown, standability, prolificacy, starch properties or quantity, oil quantity and quality, amino acid or protein composition, and the like. By "resistant" is meant a plant which exhibits substantially no phenotypic changes as a consequence of agent administration, infection with a pathogen, or exposure to stress. By "tolerant" is meant a plant which, although it may exhibit some phenotypic changes as a consequence of infection, does not have a substantially decreased reproductive capacity or substantially altered metabolism.

Vascular tissue-preferential or vascular tissue-specific transcription regulating nucleotide sequences (e.g., promoters) are useful for expressing a wide variety of genes including those which alter metabolic pathways, confer disease resistance, for protein production, e.g., antibody production, or to improve nutrient uptake and the like. Vascular tissue-preferential or vascular tissue-specific transcription regulating nucleotide sequences (e.g., promoters) may be modified so as to be regulatable, e.g., inducible. The genes and transcription regulating nucleotide sequences (e.g., promoters) described hereinabove can be used to identify orthologous genes and their transcription regulating nucleotide sequences (e.g., promoters) which are also likely expressed in a particular tissue and/or development manner. Moreover, the orthologous transcription regulating nucleotide sequences (e.g., promoters) are useful to express linked open reading frames. In addition, by aligning the transcription regulating nucleotide sequences (e.g., promoters) of these orthologs, novel cis elements can be identified that are useful to generate synthetic transcription regulating nucleotide sequences (e.g., promoters).

The expression regulating nucleotide sequences specified above may be optionally operably linked to other suitable regulatory sequences, e.g., a transcription terminator sequence, operator, repressor binding site, transcription factor binding site and/or an enhancer.

The present invention further provides a recombinant vector containing the expression cassette of the invention, and host cells comprising the expression cassette or vector, e.g., comprising a plasmid. The expression cassette or vector may augment the genome of a transformed plant or may be maintained extra chromosomally. The expression cassette or vector of the invention may be present in the nucleus, chloroplast, mitochondria and/or plastid of the cells of the plant. Preferably, the expression cassette or vector of the invention is comprised in the chromosomal DNA of the plant nucleus. The present invention also provides a transgenic plant prepared by this method, a seed from such a plant and progeny plants from such a plant including hybrids and inbreds. The expression cassette may be operatively linked to a structural gene, the open reading frame thereof, or a portion thereof. The expression cassette may further comprise a Ti plasmid and be contained in an *Agrobacterium tumefaciens* cell; it may be carried on a microparticle, wherein the microparticle is suitable for ballistic transformation of a plant cell; or it may be contained in a plant cell or protoplast. Further, the expression cassette or vector can be contained in a transformed plant or cells thereof, and the plant may be a dicot or a monocot. In particular, the plant may be a dicotyledonous plant. Preferred transgenic plants are transgenic maize, soybean, barley, alfalfa, sunflower, canola, soybean, cotton, peanut, sorghum, tobacco, sugarbeet, rice, wheat, rye, turfgrass, millet, sugarcane, tomato, or potato.

The invention also provides a method of plant breeding, e.g., to prepare a crossed fertile transgenic plant. The method comprises crossing a fertile transgenic plant comprising a particular expression cassette of the invention with itself or with a second plant, e.g., one lacking the particular expression cassette, to prepare the seed of a crossed fertile transgenic plant comprising the particular expression cassette. The seed is then planted to obtain a crossed fertile transgenic plant. The plant may be a monocot or a dicot. In a particular embodiment, the plant is a dicotyledonous plant. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants.

The transcription regulating nucleotide sequences of the invention further comprise sequences which are complementary to one (hereinafter "test" sequence) which hybridizes under stringent conditions with a nucleic acid molecule as described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45 as well as RNA which is transcribed from the nucleic acid molecule. When the hybridization is performed under stringent conditions, either the test or nucleic acid molecule of invention is preferably supported, e.g., on a membrane or DNA chip. Thus, either a denatured test or nucleic acid molecule of the invention is preferably first bound to a support and hybridization is effected for a specified period of time at a temperature of, e.g., between 55 and 70° C., in double strength citrate buffered saline (SC) containing 0.1% SDS followed by rinsing of the support at the same temperature but with a buffer having a reduced SC concentration. Depending upon the degree of stringency required such reduced concentration buffers are typically single strength SC containing 0.1% SDS, half strength SC containing 0.1% SDS and one-tenth strength SC containing 0.1% SDS. More preferably hybridization is carried out under high stringency conditions (as defined above).

Virtually any DNA composition may be used for delivery to recipient plant cells, e.g., dicotyledonous cells, to ultimately produce fertile transgenic plants in accordance with the present invention. For example, DNA segments or fragments in the form of vectors and plasmids, or linear DNA segments or fragments, in some instances containing only the DNA element to be expressed in the plant, and the like, may be employed. The construction of vectors which may be employed in conjunction with the present invention will be known to those of skill of the art in light of the present disclosure (see, e.g., Sambrook 1989; Gelvin 1990).

Vectors, plasmids, cosmids, YACs (yeast artificial chromosomes), BACs (bacterial artificial chromosomes) and DNA segments for use in transforming such cells will, of course, generally comprise the cDNA, gene or genes which one desires to introduce into the cells. These DNA constructs can further include structures such as promoters, enhancers, polylinkers, or even regulatory genes as desired. The DNA segment, fragment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki 1991). These vectors are capable of autonomous replication in maize cells as well as E. coli, and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs 1990) that transposition of these elements within the maize genome requires DNA replication. It is also contemplated that transposable elements would be useful for introducing DNA segments or fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells. The use of a transposable element such as Ac, Ds, or Mu may actively promote integration of the DNA of interest and hence increase the frequency of stably transformed cells. Transposable elements may be useful to allow separation of genes of interest from elements necessary for selection and maintenance of a plasmid vector in bacteria or selection of a transformant. By use of a transposable element, desirable and undesirable DNA sequences may be transposed apart from each other in the genome, such that through genetic segregation in progeny, one may identify plants with either the desirable undesirable DNA sequences.

The nucleotide sequence of interest linked to one or more of the transcription regulating nucleotide sequences of the invention can, for example, code for a ribosomal RNA, an antisense RNA or any other type of RNA that is not translated into protein. In another preferred embodiment of the invention, said nucleotide sequence of interest is translated into a protein product. The transcription regulating nucleotide sequence and/or nucleotide sequence of interest linked thereto may be of homologous or heterologous origin with respect to the plant to be transformed. A recombinant DNA molecule useful for introduction into plant cells includes that which has been derived or isolated from any source, that may be subsequently characterized as to structure, size and/or function, chemically altered, and later introduced into plants. An example of a nucleotide sequence or segment of interest "derived" from a source, would be a nucleotide sequence or segment that is identified as a useful fragment within a given organism, and which is then chemically synthesized in essentially pure form. An example of such a nucleotide sequence or segment of interest "isolated" from a source, would be nucleotide sequence or segment that is excised or removed from said source by chemical means, e.g., by the use of restriction endonucleases, so that it can be further manipulated, e.g., amplified, for use in the invention, by the methodology of genetic engineering. Such a nucleotide sequence or segment is commonly referred to as "recombinant."

Therefore a useful nucleotide sequence, segment or fragment of interest includes completely synthetic DNA, semi-synthetic DNA, DNA isolated from biological sources, and DNA derived from introduced RNA. Generally, the introduced DNA is not originally resident in the plant genotype which is the recipient of the DNA, but it is within the scope of the invention to isolate a gene from a given plant genotype, and to subsequently introduce multiple copies of the gene into the same genotype, e.g., to enhance production of a given gene product such as a storage protein or a protein that confers tolerance or resistance to water deficit.

The introduced recombinant DNA molecule includes but is not limited to, DNA from plant genes, and non-plant genes such as those from bacteria, yeasts, animals or viruses. The introduced DNA can include modified genes, portions of genes, or chimeric genes, including genes from the same or different geno-type. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed plant.

The introduced recombinant DNA molecule used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant plant. Generally, the introduced recombinant DNA molecule will be relatively small, i.e., less than about 30 kb to minimize any susceptibility to physical, chemical, or enzymatic degradation which is known to increase as the size of the nucleotide molecule increases. As noted above, the number of proteins, RNA transcripts or mixtures thereof which is introduced into the plant genome is preferably preselected and defined, e.g., from one to about 5-10 such products of the introduced DNA may be formed.

Two principal methods for the control of expression are known, viz.: overexpression and underexpression. Overexpression can be achieved by insertion of one or more than one extra copy of the selected gene. It is, however, not unknown for plants or their progeny, originally transformed with one or more than one extra copy of a nucleotide sequence, to exhibit the effects of underexpression as well as overexpression. For underexpression there are two principle methods which are commonly referred to in the art as "antisense downregulation" and "sense downregulation" (sense downregulation is also referred to as "cosuppression"). Generically these processes are referred to as "gene silencing". Both of these methods lead to an inhibition of expression of the target gene.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

It is specifically contemplated by the inventors that one could mutagenize a promoter to potentially improve the utility of the elements for the expression of transgenes in plants. The mutagenesis of these elements can be carried out at random and the mutagenized promoter sequences screened for activity in a trial-by-error procedure. Alternatively, particular sequences which provide the promoter with desirable expression characteristics, or the promoter with expression enhancement activity, could be identified and these or similar sequences introduced into the sequences via mutation. It is further contemplated that one could mutagenize these sequences in order to enhance their expression of transgenes in a particular species.

The means for mutagenizing a DNA segment encoding a promoter sequence of the current invention are well-known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids also are routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the promoter. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (1990) and Upender et al. (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

As used herein; the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Rarnstad, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224. A number of template dependent processes are available to amplify the target sequences of interest present in a sample, such methods being well known in the art and specifically disclosed herein below.

Where a clone comprising a promoter has been isolated in accordance with the instant invention, one may wish to delimit the essential promoter regions within the clone. One efficient, targeted means for preparing mutagenizing promoters relies upon the identification of putative regulatory elements within the promoter sequence. This can be initiated by comparison with promoter sequences known to be expressed in similar tissue-specific or developmentally unique manner. Sequences which are shared among promoters with similar expression patterns are likely candidates for the binding of transcription factors and are thus likely elements which confer expression patterns. Confirmation of these putative regulatory elements can be achieved by deletion analysis of each putative regulatory region followed by functional analysis of each deletion construct by assay of a reporter gene which is functionally attached to each construct. As such, once a starting promoter sequence is provided, any of a number of different deletion mutants of the starting promoter could be readily prepared.

Functionally equivalent fragments of a transcription regulating nucleotide sequence of the invention can also be obtained by removing or deleting non-essential sequences without deleting the essential one. Narrowing the transcription regulating nucleotide sequence to its essential, transcription mediating elements can be realized in vitro by trial-and-arrow deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the BIOBASE database "Transfac" (Biologische Datenbanken GmbH, Braunschweig; Wingender 2001) or the database PlantCARE (Lescot 2002).

Preferably, functional equivalent fragments of one of the transcription regulating nucleotide sequences of the invention comprises at least 100 base pairs, preferably, at least 200 base pairs, more preferably at least 500 base pairs of a transcription regulating nucleotide sequence as described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, or 45. More preferably this fragment is starting from the 3'-end of the indicated sequences.

Especially preferred are equivalent fragments of transcription regulating nucleotide sequences, which are obtained by deleting the region encoding the 5'-untranslated region of the mRNA, thus only providing the (untranscribed) promoter region. The 5'-untranslated region can be easily determined by methods known in the art (such as 5'-RACE analysis). Accordingly, some of the transcription regulating nucleotide sequences of the invention are equivalent fragments of other sequences (see Table 2 below).

TABLE 2

Relationship of transcription regulating nucleotide sequences of the invention

| Transcription regulating sequence | Equivalent sequence | Equivalent fragment |
| --- | --- | --- |
| SEQ ID NO: 5 (3977 bp) | | SEQ ID NO: 1 (1043 bp) |
| | | SEQ ID NO: 2 (1057 bp) |
| | | SEQ ID NO: 3 (2464 bp) |
| | | SEQ ID NO: 4 (2478 bp) |
| SEQ ID NO: 12 (1931 bp) | SEQ ID NO: 13 (1945 bp) | SEQ ID NO: 8 (1147 bp) |
| | | SEQ ID NO: 9 (1161 bp) |
| | | SEQ ID NO: 10 (304 bp) |
| | | SEQ ID NO: 11 (316 bp) |
| | | SEQ ID NO: 14 (1088 bp) |
| | | SEQ ID NO: 15 (1100 bp) |

TABLE 2-continued

Relationship of transcription regulating nucleotide sequences of the invention

| Transcription regulating sequence | Equivalent sequence | Equivalent fragment |
| --- | --- | --- |
| SEQ ID NO: 22 (2399 bp) | SEQ ID NO: 23 (2413 bp) | SEQ ID NO: 18 (1235 bp) |
| | | SEQ ID NO: 19 (1249 bp) |
| | | SEQ ID NO: 20 (1135 bp) |
| | | SEQ ID NO: 21 (1147 bp) |
| | | SEQ ID NO: 24 (2299 bp) |
| | | SEQ ID NO: 25 (2311 bp) |
| SEQ ID NO: 32 (2096 bp) | SEQ ID NO: 33 (2110 bp) | SEQ ID NO: 28 (1051 bp) |
| | | SEQ ID NO: 29 (1065 bp) |
| | | SEQ ID NO: 30 (1038 bp) |
| | | SEQ ID NO: 31 (1050 bp) |
| | | SEQ ID NO: 34 (2083 bp) |
| | | SEQ ID NO: 35 (2095 bp) |
| SEQ ID NO: 42 (2022 bp) | SEQ ID NO: 43 (2036 bp) | SEQ ID NO: 38 (1030 bp) |
| | | SEQ ID NO: 39 (1044 bp) |
| | | SEQ ID NO: 40 (968 bp) |
| | | SEQ ID NO: 41 (980 bp) |
| | | SEQ ID NO: 44 (1960 bp) |
| | | SEQ ID NO: 45 (1972 bp) |

As indicated above, deletion mutants, deletion mutants of the promoter of the invention also could be randomly prepared and then assayed. With this strategy, a series of constructs are prepared, each containing a different portion of the clone (a subclone), and these constructs are then screened for activity. A suitable means for screening for activity is to attach a deleted promoter or intron construct which contains a deleted segment to a selectable or screenable marker, and to isolate only those cells expressing the marker gene. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous genes.

An expression cassette of the invention may comprise further regulatory elements. The term in this context is to be understood in the a broad meaning comprising all sequences which may influence construction or function of the expression cassette. Regulatory elements may for example modify transcription and/or translation in prokaryotic or eukaryotic organism. In an preferred embodiment the expression cassette of the invention comprised downstream (in 3'-direction) of the nucleic acid sequence to be expressed a transcription termination sequence and—optionally additional regulatory elements—each operably liked to the nucleic acid sequence to be expressed (or the transcription regulating nucleotide sequence).

Additional regulatory elements may comprise additional promoter, minimal promoters, or promoter elements, which may modify the expression regulating properties. For example the expression may be made depending on certain stress factors such water stress, abscisin (Lam 1991) or heat stress (Schoffl 1989). Furthermore additional promoters or promoter elements may be employed, which may realized expression in other organisms (such as *E. coli* or *Agrobacterium*). Such regulatory elements can be find in the promoter sequences or bacteria such as amy and SPO2 or in the promoter sequences of yeast or fungal promoters (such as ADC1, MFa, AC, P-60, CYC1, GAPDH, TEF, rp28, and ADH).

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters which are useful for plant transgene expression include those that are inducible, viral, synthetic, constitutive (Odell 1985), temporally regulated, spatially regulated, tissue-specific, and spatial-temporally regulated.

Where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A variety of 5' and 3' transcriptional regulatory sequences are available for use in the present invention. Transcriptional terminators are responsible for the termination of transcription and correct mRNA polyadenylation. The 3' nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, one also could use a gamma coixin, oleosin 3 or other terminator from the genus *Coix*.

Preferred 3' elements include those from the nopaline synthase gene of *Agrobacterium tumefaciens* (Bevan 1983), the terminator for the T7 transcript from the octopine synthase gene of *Agrobacterium tumefaciens*, and the 3' end of the protease inhibitor 1 or 11 genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will be most preferred.

Preferred regulatory elements also include the 5'-untranslated region, introns and the 3'-untranslated region of genes. Such sequences that have been found to enhance gene expression in transgenic plants include intron sequences (e.g., from Adh1, bronze1, actin1, actin 2 (WO 00/760067), or the sucrose synthase intron; see: The Maize Handbook, Chapter 116, Freeling and Walbot, Eds., Springer, New York (1994)) and viral leader sequences (e.g., from TMV, MCMV and AMV; Gallie 1987). For example, a number of non-translated leader sequences derived from viruses are known to enhance expression. Specifically, leader sequences from Tobacco Mosaic Virus (TMV), Maize Chlorotic Mottle Virus (MCMV), and Alfalfa Mosaic Virus (AMV) have been shown to be effective in enhancing expression (e.g., Gallie 1987; Skuzeski 1990). Other leaders known in the art include but are not limited to: Picornavirus leaders, for example, EMCV leader (Encephalomyocarditis 5' noncoding region) (Elroy-Stein 1989); Potyvirus leaders, for example, TEV leader (Tobacco Etch Virus); MDMV leader (Maize Dwarf Mosaic Virus); Human immunoglobulin heavy-chain binding protein (BiP) leader, (Macejak 1991); Untranslated leader from the coat protein mRNA of alfalfa mosaic virus (AMV RNA 4), (Jobling 1987; Tobacco mosaic virus leader (TMV), (Gallie 1989; and Maize Chlorotic Mottle Virus leader (MCMV) (Lommel 1991. See also, Della-Cioppa 1987. Regulatory elements such as Adh intron 1 (Callis 1987), sucrose synthase intron (Vasil 1989) or TMV omega element (Gallie 1989), may further be included where desired. Especially preferred are the 5'-untranslated region, introns and the 3'-untranslated region from the genes described by the GenBank *Arabidopsis thaliana* genome loci At4g00140, At5g45350, At2g39830, At1g68430, or At5g67280, or of functional equivalent thereof.

Additional preferred regulatory elements are enhancer sequences or polyadenylation sequences. Preferred polyadenylation sequences are those from plant genes or *Agrobacterium* T-DNA genes (such as for example the terminator sequences of the OCS (octopine synthase) or NOS (nopaline synthase) genes).

Examples of enhancers include elements from the CaMV 35S promoter, octopine synthase genes (Ellis et al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Vectors for use in accordance with the present invention may be constructed to include the ocs enhancer element. This element was first identified as a 16 bp palindromic enhancer from the octopine synthase (ocs) gene of ultilane (Ellis 1987), and is present in at least 10 other promoters (Bouchez 1989). The use of an enhancer element, such as the ocs elements and particularly multiple copies of the element, will act to increase the level of transcription from adjacent promoters when applied in the context of plant transformation.

An expression cassette of the invention (or a vector derived therefrom) may comprise additional functional elements, which are to be understood in the broad sense as all elements which influence construction, propagation, or function of an expression cassette or a vector or a transgenic organism comprising them. Such functional elements may include origin of replications (to allow replication in bacteria; for the ORI of pBR322 or the P15A ori; Sambrook 1989), or elements required for *Agrobacterium* T-DNA transfer (such as for example the left and/or rights border of the T-DNA).

Ultimately, the most desirable DNA segments for introduction into, for example, a dicot genome, may be homologous genes or gene families which encode a desired trait (e.g., increased yield per acre) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the expression of a gene in a vascular tissue-preferential or vascular tissue-specific manner.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance gene, such as the EPSPS gene, to a particular organelle such as the chloroplast rather than to the cytoplasm. This is exemplified by the use of the rbcs transit peptide which confers plastid-specific targeting of proteins. In addition, it is proposed that it may be desirable to target certain genes responsible for male sterility to the mitochondria, or to target certain genes for resistance to phytopathogenic organisms to the extracellular spaces, or to target proteins to the vacuole.

By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. Targeting of certain proteins may be desirable in order to enhance the stability of the protein (U.S. Pat. No. 5,545,818).

It may be useful to target DNA itself within a cell. For example, it may be useful to target introduced DNA to the nucleus as this may increase the frequency of transformation. Within the nucleus itself it would be useful to target a gene in order to achieve site specific integration. For example, it would be useful to have an gene introduced through transformation replace an existing gene in the cell. Other elements include those that can be regulated by endogenous or exogenous agents, e.g., by zinc finger proteins, including naturally occurring zinc finger proteins or chimeric zinc finger proteins (see, e.g., U.S. Pat. No. 5,789,538, WO 99/48909; WO 99/45132; WO 98/53060; WO 98/53057; WO 98/53058; WO 00/23464; WO 95/19431; and WO 98/54311) or myb-like transcription factors. For example, a chimeric zinc finger protein may include amino acid sequences which bind to a specific DNA sequence (the zinc finger) and amino acid sequences that activate (e.g., GAL 4 sequences) or repress the transcription of the sequences linked to the specific DNA sequence.

It is one of the objects of the present invention to provide recombinant DNA molecules comprising a nucleotide sequence according to the invention operably linked to a nucleotide segment of interest.

A nucleotide segment of interest is reflective of the commercial markets and interests of those involved in the development of the crop. Crops and markets of interest changes, and as developing nations open up world markets, new crops and technologies will also emerge. In addition, as the understanding of agronomic traits and characteristics such as yield and heterosis increase, the choice of genes for transformation will change accordingly. General categories of nucleotides of interest include, for example, genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in starch, oil, carbohydrate, or nutrient metabolism, as well as those affecting kernel size, sucrose loading, zinc finger proteins, see, e.g., U.S. Pat. No. 5,789,538, WO 99/48909; WO 99/45132; WO 98/53060; WO 98/53057; WO 98/53058; WO 00/23464; WO 95/19431; and WO 98/54311, and the like.

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric Cre transgene, it can be crossed with lines carrying different inactive replicons or inactive transgene for activation.

Other sequences which may be linked to the gene of interest which encodes a polypeptide are those which can target to a specific organelle, e.g., to the mitochondria, nucleus, or plastid, within the plant cell. Targeting can be achieved by providing the polypeptide with an appropriate targeting peptide sequence, such as a secretory signal peptide (for secretion or cell wall or membrane targeting, a plastid transit peptide, a chloroplast transit peptide, e.g., the chlorophyll a/b binding protein, a mitochondrial target peptide, a vacuole targeting peptide, or a nuclear targeting peptide, and the like. For example, the small subunit of ribulose bisphosphate carboxylase transit peptide, the EPSPS transit peptide or the dihydrodipicolinic acid synthase transit peptide may be used. For examples of plastid organelle targeting sequences (see WO 00/12732). Plastids are a class of plant organelles derived from proplastids and include chloroplasts, leucoplasts, amyloplasts, and chromoplasts. The plastids are major sites of biosynthesis in plants. In addition to photosynthesis in the chloroplast, plastids are also sites of lipid biosynthesis, nitrate reduction to ammonium, and starch storage. And while plastids contain their own circular, genome, most of the proteins localized to the plastids are encoded by the nuclear genome and are imported into the organelle from the cytoplasm.

Transgenes used with the present invention will often be genes that direct the expression of a particular protein or polypeptide product, but they may also be non-expressible DNA segments, e.g., transposons such as Ds that do no direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch properties; oil quantity and quality; and the like. One may desire to incorporate one or more genes conferring any such desirable trait or traits, such as, for example, a gene or genes encoding pathogen resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

1. Exemplary Transgenes 1.1 Insect Resistance

An important aspect of the present invention concerns the introduction of insect resistance-conferring genes into plants. Especially for preventing damages caused by sucking insects expression of insecticidal protein in vascular tissues is contemplated to be useful. Potential insect resistance genes which can be introduced include *Bacillus thuringiensis* crystal toxin genes or Bt genes (Watrud 1985). Bt genes may provide resistance to lepidopteran or coleopteran pests such as European Corn Borer (ECB) and corn rootworm (CRW). Preferred Bt toxin genes for use in such embodiments include the CrylA(b) and CrylA(c) genes. Endotoxin genes from other species of *B. thuringiensis* which affect insect growth or development may also be employed in this regard. Protease inhibitors may also provide insect resistance (Johnson 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes which encode inhibitors of the insects' digestive system, or those that encode enzymes or co-factors that facilitate the production of inhibitors, may also be useful. This group may be exemplified by cystatin and amylase inhibitors, such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock 1990; Czapla & Lang, 1990). Lectin genes contemplated to be useful include, for example, barley and wheat germ agglutinin (WGA) and rice lectins (Gatehouse 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated, that the expression of juvenile hormone esterase, directed towards specific insect pests, may also result in insecticidal activity, or perhaps cause cessation of metamorphosis (Hammock 1990).

Transgenic plants expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming plants to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway (Dunn 1981). The introduction of genes that can regulate the production of maysin, and genes involved in the production of dhurrin in sorghum, is also contemplated to be of use in facilitating resistance to earworm and rootworm, respectively.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson & Guss, 1972).

Further genes encoding proteins characterized as having potential insecticidal activity may also be used as transgenes in accordance herewith. Such genes include, for example, the cowpea trypsin inhibitor (CpTI; Hilder 1987) which may be used as a rootworm deterrent; genes encoding avermectin (Campbell 1989; Ikeda 1987) which may prove particularly useful as a corn rootworm deterrent; ribosome inactivating protein genes; and even genes that regulate plant structures. Transgenic maize including anti-insect antibody genes and genes that code for enzymes that can covert a non-toxic insecticide (pro-insecticide) applied to the outside of the plant into an insecticide inside the plant are also contemplated.

1.2 Environment or Stress Resistance

Improvement of a plant's ability to tolerate various environmental stresses such as, but not limited to, drought, excess moisture, chilling, freezing, high temperature, salt, and oxidative stress, can also be effected through expression of heterologous, or overexpression of homologous genes. Especially expression of genes improving transport capabilities in vascular tissue is contemplated to be useful in the context of the present invention. Benefits may be realized in terms of increased resistance to freezing temperatures through the introduction of an "antifreeze" protein such as that of the Winter Flounder (Cutler 1989) or synthetic gene derivatives thereof. Improved chilling tolerance may also be conferred through increased expression of glycerol-3-phosphate acetyltransferase in chloroplasts (Murata 1992; Wolter 1992). Resistance to oxidative stress (often exacerbated by conditions such as chilling temperatures in combination with high light intensities) can be conferred by expression of superoxide dismutase (Gupta 1993), and may be improved by glutathione reductase (Bowler 1992). Such strategies may allow for tolerance to freezing in newly emerged fields as well as extending later maturity higher yielding varieties to earlier relative maturity zones.

Expression of novel genes that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a gene encoding the biosynthesis of osmotically-active solutes can impart protection against drought. Within this class of genes are DNAs encoding mannitol dehydrogenase (Lee and Saier, 1982) and trehalose-6-phosphate synthase (Kaasen 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski 1992).

Similarly, the efficacy of other metabolites in protecting either enzyme function (e.g. alanopine or propionic acid) or membrane integrity (e.g., alanopine) has been documented (Loomis 1989), and therefore expression of gene encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson 1992), sorbitol, dulcitol (Karsten 1992), glucosylglycerol, (Reed 1984; Erdmann 1992), sucrose, stachyose (Koster & Leopold 1988; Blackman 1992), ononitol and pinitol (Vernon & Bohnert 1992), and raffinose (Bernal-Lugo & Leopold 1992). Other osmotically active solutes which are not sugars include, but are not limited to, proline and glycine-betaine (Wyn-Jones and Storey, 1981). Continued canopy growth and increased reproductive fitness during times of stress can be augmented by introduction and expression of genes such as those controlling the osmotically active compounds discussed above and other such compounds, as represented in one exemplary embodiment by the enzyme myoinositol 0-methyltransferase.

It is contemplated that the expression of specific proteins may also increase drought tolerance. Three classes of Late Embryogenic Proteins have been assigned based on structural similarities (see Dure 1989). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (e.g. Mundy and Chua, 1988; Piatkowski 1990; Yamaguchi-Shinozaki 1992). Recently, expression of a Type-III LEA (HVA-1) in tobacco was found to influence plant height, maturity and drought tolerance (Fitzpatrick, 1993). Expression of structural genes from all three groups may therefore confer drought tolerance. Other types of proteins induced during water stress include thiol proteases, aldolases and transmembrane transporters (Guerrero 1990), which may confer various protective and/or repair-type functions during drought stress. The expression of a gene that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in maize. Many of these genes also improve freezing tolerance (or resistance); the physical stresses incurred during freezing and drought are similar in nature and may be mitigated in similar fashion. Benefit may be conferred via constitutive or tissue-specific expression of these genes, but the preferred means of expressing these novel genes may be through the use of a turgor-induced promoter (such as the promoters for the turgor-induced genes described in Guerrero et al. 1990 and Shagan 1993). Spatial and temporal expression patterns of these genes may enable maize to better withstand stress.

Expression of genes that are involved with specific morphological traits that allow for increased water extractions from drying soil would be of benefit. For example, introduction and expression of genes that alter root characteristics may enhance water uptake. Expression of genes that enhance reproductive fitness during times of stress would be of significant value. For example, expression of DNAs that improve the synchrony of pollen shed and receptiveness of the female flower parts, i.e., silks, would be of benefit. In addition, expression of genes that minimize kernel abortion during times of stress would increase the amount of grain to be harvested and hence be of value. Regulation of cytokinin levels in monocots, such as maize, by introduction and expression of an isopentenyl transferase gene with appropriate regulatory sequences can improve monocot stress resistance and yield (Gan 1995).

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Improved protection of the plant to abiotic stress factors such as drought, heat or chill, can also be achieved—for example—by overexpressing antifreeze polypeptides from

*Myoxocephalus Scorpius* (WO 00/00512), *Myoxocephalus octodecemspinosus*, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature-Biotechnology 17:192-196), oxalate oxidase (WO 99/04013; Dunwell J M (1998) Biotechn Genet Eng Rev 15:1-32), DREBLA factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

1.3 Disease Resistance

It is proposed that increased resistance to diseases may be realized through introduction of genes into plants period. Especially expression of genes that confer resistance against systemically acting pathogens (such as bacteria or virus), which utilize the vascular tissue to migrate throughout the plant, is thought to be useful. It is possible to produce resistance to diseases caused, by viruses, bacteria, fungi, root pathogens, insects and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo 1988, Hemenway 1988, Abel 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in plants may be useful in conferring resistance to bacterial disease. These genes are induced following pathogen attack on a host plant and have been divided into at least five classes of proteins (Bol 1990). Included amongst the PR proteins are beta-1,3-glucanases, chitinases, and osmotin and other proteins that are believed to function in plant resistance to disease organisms. Other genes have been identified that have anti-fungal properties, e.g., UDA (stinging nettle lectin) and hevein (Broakgert 1989; Barkai-Golan 1978). It is known that certain plant diseases are caused by the production of phytotoxins. Resistance to these diseases could be achieved through expression of a novel gene that encodes an enzyme capable of degrading or otherwise inactivating the phytotoxin. Expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants. It is proposed that it would be possible to make the plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

Furthermore, a resistance to fungi, insects, nematodes and diseases, can be achieved by by targeted accumulation of certain metabolites or proteins. Such proteins include but are not limited to glucosinolates (defense against herbivores), chitinases or glucanases and other enzymes which destroy the cell wall of parasites, ribosome-inactivating proteins (RIPs) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, a-amylase inhibitor or protease inhibitors (cowpea trypsin inhibitor), lectins such as wheatgerm agglutinin, RNAses or ribozymes. Further examples are nucleic acids which encode the *Trichoderma harzianum* chit42 endochitinase (GenBank Acc. No.: S78423) or the N-hydroxylating, multi-functional cytochrome P-450 (CYP79) protein from *Sorghum bicolor* (GenBank Acc. No.: U32624), or functional equivalents of these. The accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Broglie et al. (1991) Science 254:1194-1197), is advantageous. Resistance to pests such as, for example, the rice pest *Nilaparvata lugens* in rice plants can be achieved by expressing the snowdrop (*Galanthus nivalis*) lectin agglutinin (Rao et al. (1998) Plant J 15(4):469-77). The expression of synthetic crylA(b) and cry-1A(c) genes, which encode lepidoptera-specific *Bacillus thuringiensis* D-endotoxins can bring about a resistance to insect pests in various plants (Goyal R K et al. (2000) Crop Protection 19(5):307-312). Further target genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164).

1.4 Plant Agronomic Characteristics

Two of the factors determining where plants can be grown are the average daily temperature during the growing season and the length of time between frosts. Within the areas where it is possible to grow a particular plant, there are varying limitations on the maximal time it is allowed to grow to maturity and be harvested. The plant to be grown in a particular area is selected for its ability to mature and dry down to harvestable moisture content within the required period of time with maximum possible yield. Therefore, plant of varying maturities are developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. Genes that influence maturity and/or dry down can be identified and introduced into plant lines using transformation techniques to create new varieties adapted to different growing locations or the same growing location but having improved yield to moisture ratio at harvest. Expression of genes that are involved in regulation of plant development may be especially useful, e.g., the liguleless and rough sheath genes that have been identified in plants. Promoters, which can mediate vascular-tissue specific or -preferential expression are especially useful in this context to enhance resistance against draught.

Genes may be introduced into plants that would improve standability and other plant growth characteristics. For example, expression of novel genes which confer stronger stalks, improved root systems, or prevent or reduce ear droppage would be of great value to the corn farmer. Introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field.

Delay of late season vegetative senescence would increase the flow of assimilate into the grain and thus increase yield. Overexpression of genes within plants that are associated with "stay green" or the expression of any gene that delays senescence would be advantageous. For example, a non-yellowing mutant has been identified in *Festuca pratensis* (Davies 1990). Expression of this gene as well as others may prevent premature breakdown of chlorophyll and thus maintain canopy function.

1.5 Nutrient Utilization

The ability to utilize available nutrients and minerals may be a limiting factor in growth of many plants. It is proposed that it would be possible to alter nutrient uptake, tolerate pH extremes, mobilization through the plant, storage pools, and availability for metabolic activities by the introduction of novel genes. These modifications would allow a plant to more efficiently utilize available nutrients. It is contemplated that an increase in the activity of, for example, an enzyme that is normally present in the plant and involved in nutrient utilization would increase the availability of a nutrient. An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

1.6. Non-Protein-Expressing Sequences 1.6.1 RNA-Expressing

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA or double-stranded RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes.

An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Expression of antisense-RNA or double-stranded RNA by one of the expression cassettes of the invention is especially preferred. Also expression of sense RNA can be employed for gene silencing (co-suppression). This RNA is preferably a non-translatable RNA. Gene regulation by double-stranded RNA ("double-stranded RNA interference"; dsRNAi) is well known in the arte and described for various organism including plants (e.g., Matzke 2000; Fire A et al 1998; WO 99/32619; WO 99/53050; WO 00/68374; WO 00/44914; WO 00/44895; WO 00/49035; WO 00/63364).

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants which possess them. The transgenic plants may possess reduced levels of polypeptides including but not limited to the polypeptides cited above that may be affected by antisense RNA.

It is also possible that genes may be introduced to produce novel transgenic plants which have reduced expression of a native gene product by a mechanism of cosuppression. It has been demonstrated in tobacco, tomato, and petunia (Goring 1991; Smith 1990; Napoli 1990; van der Krol 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

1.6.2 Non-RNA-Expressing

For example, DNA elements including those of transposable elements such as Ds, Ac, or Mu, may be, inserted into a gene and cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta 1988). Once identified, the entire gene(s) for the particular trait, including control or regulatory regions where desired may be isolated, cloned and manipulated as desired. The utility of DNA elements introduced into an organism for purposed of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief 1989), which can be positioned around an expressible gene of interest to effect an increase in overall expression of the gene and diminish position dependant effects upon incorporation into the plant genome (Stief 1989; Phi-Van 1990).

Further nucleotide sequences of interest that may be contemplated for use within the scope of the present invention in operable linkage with the promoter sequences according to the invention are isolated nucleic acid molecules, e.g., DNA or RNA, comprising a plant nucleotide sequence according to the invention comprising an open reading frame that is preferentially expressed in a specific tissue, i.e., vascular-, root-, green tissue (leaf and stem), panicle-, or pollen, or is expressed constitutively.

2. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait, the green fluorescent protein (GFP)). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel 1990) molecule is well characterized in terms of molecular biology, expression and protein structure. However, any one of a variety of ultilane and/or glycine-rich wall proteins (Keller 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin, however, virtually any detectable epitope may be employed in such embodiments, as selected from the extremely wide variety of antigen-antibody combinations known to those of skill in the art. The unique extracellular epitope can then be straightforwardly detected using antibody labeling in conjunction with chromogenic or fluorescent adjuncts.

Elements of the present disclosure may be exemplified in detail through the use of the bar and/or GUS genes, and also through the use of various other markers. Of course, in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

2.1 Selectable Markers

Various selectable markers are known in the art suitable for plant transformation. Such markers can be expressed under a transcription regulating nucleotide sequence of the invention but can also be employed in operable linkage with another promoter (e.g., a constitutive promoter) as a separate expression cassette in an expression construct or vector of the invention. Such markers may include but are not limited to:

2.1.1 Negative Selection Markers

Negative selection markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Transformed plant material (e.g., cells, tissues or plantlets), which express marker genes, are capable of developing in the presence of concentrations of a corresponding selection compound (e.g., antibiotic or herbicide) which suppresses growth of an untransformed wild type tissue. Especially preferred negative selection markers are those which confer resistance to herbicides. Examples which may be mentioned are:

Phosphinothricin acetyltransferases (PAT; also named Bialophos® resistance; bar; de Block 1987; Vasil 1992, 1993; Weeks 1993; Becker 1994; Nehra 1994; Wan & Lemaux 1994; EP 0 333 033; U.S. Pat. No. 4,975,374). Preferred are the bar gene from *Streptomyces hygroscopicus* or the pat gene from *Streptomyces viridochromogenes*. PAT inactivates the active ingredient in the herbicide bialaphos, phosphinothricin (PPT). PPT inhibits glutamine synthetase, (Murakami 1986; Twell 1989) causing rapid accumulation of ammonia and cell death.

- altered 5-enolpyruvylshikimate-3-phosphate synthase (EPSPS) conferring resistance to Glyphosate® (N-(phosphonomethyl)glycine) (Hinchee 1988; Shah 1986; Della-Cioppa 1987). Where a mutant EPSP synthase gene is employed, additional benefit may be realized through the incorporation of a suitable chloroplast transit peptide, CTP (EP-A1 0 218 571).
- Glyphosate® degrading enzymes (Glyphosate® oxidoreductase; gox),
- Dalapon® inactivating dehalogenases (deh)
- sulfonylurea- and/or imidazolinone-inactivating acetolactate synthases (ahas or ALS; for example mutated ahas/ALS variants with, for example, the S4, XI12, XA17, and/or Hra mutation (EP-A1 154 204)
- Bromoxynil® degrading nitrilases (bxn; Stalker 1988)
- Kanamycin- or geneticin (G418) resistance genes (NPTII; NPT or neo; Potrykus 1985) coding e.g., for neomycin phosphotransferases (Fraley 1983; Nehra 1994)
- 2-Desoxyglucose-6-phosphate phosphatase (DOG$^R$1-Gene product; WO 98/45456; EP 0 807 836) conferring resistance against 2-desoxyglucose (Randez-Gil 1995).
- hygromycin phosphotransferase (HPT), which mediates resistance to hygromycin (Vanden Elzen 1985).
- altered dihydrofolate reductase (Eichholtz 1987) conferring resistance against methotrexat (Thillet 1988);
- mutated anthranilate synthase genes that confers resistance to 5-methyl tryptophan.

Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Hayford 1988; Jones 1987; Svab 1990; Hille 1986).

Especially preferred are negative selection markers that confer resistance against the toxic effects imposed by D-amino acids like e.g., D-alanine and D-serine (WO 03/060133; Erikson 2004). Especially preferred as negative selection marker in this contest are the dao1 gene (EC: 1.4. 3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3. 1.18; GenBank Acc.-No.: J01603).

Transformed plant material (e.g., cells, embryos, tissues or plantlets) which express such marker genes are capable of developing in the presence of concentrations of a corresponding selection compound (e.g., antibiotic or herbicide) which suppresses growth of an untransformed wild type tissue. The resulting plants can be bred and hybridized in the customary fashion. Two or more generations should be grown in order to ensure that the genomic integration is stable and hereditary. Corresponding methods are described (Jenes 1993; Potrykus 1991).

Furthermore, reporter genes can be employed to allow visual screening, which may or may not (depending on the type of reporter gene) require supplementation with a substrate as a selection compound.

Various time schemes can be employed for the various negative selection marker genes. In case of resistance genes (e.g., against herbicides or D-amino acids) selection is preferably applied throughout callus induction phase for about 4 weeks and beyond at least 4 weeks into regeneration. Such a selection scheme can be applied for all selection regimes. It is furthermore possible (although not explicitly preferred) to remain the selection also throughout the entire regeneration scheme including rooting.

For example, with the phosphinotricin resistance gene (bar) as the selective marker, phosphinotricin at a concentration of from about 1 to 50 mg/l may be included in the medium. For example, with the dao1 gene as the selective marker, D-serine or D-alanine at a concentration of from about 3 to 100 mg/l may be included in the medium. Typical concentrations for selection are 20 to 40 mg/l. For example, with the mutated ahas genes as the selective marker, PURSUIT™ at a concentration of from about 3 to 100 mg/l may be included in the medium. Typical concentrations for selection are 20 to 40 mg/l.

2.1.2 Positive Selection Marker

Furthermore, positive selection marker can be employed. Genes like isopentenyltransferase from *Agrobacterium tumefaciens* (strain:PO22; Genbank Acc.-No.: AB025109) may— as a key enzyme of the cytokinin biosynthesis—facilitate regeneration of transformed plants (e.g., by selection on cytokinin-free medium). Corresponding selection methods are described (Ebinuma 2000a,b). Additional positive selection markers, which confer a growth advantage to a transformed plant in comparison with a non-transformed one, are described e.g., in EP-A 0 601 092. Growth stimulation selection markers may include (but shall not be limited to) □-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

2.1.3 Counter-Selection Marker

Counter-selection markers are especially suitable to select organisms with defined deleted sequences comprising said marker (Koprek 1999). Examples for counter-selection marker comprise thymidin kinases (TK), cytosine deaminases (Gleave 1999; Perera 1993; Stougaard 1993), cytochrom P450 proteins (Koprek 1999), haloalkan dehalogenases (Naested 1999), iaaH gene products (Sundaresan 1995), cytosine deaminase codA (Schlaman & Hooykaas 1997), tms2 gene products (Fedoroff & Smith 1993), or □-naphthalene acetamide (NAM; Depicker 1988). Counter selection markers may be useful in the construction of transposon tagging lines. For example, by marking an autonomous transposable element such as Ac, Master Mu, or En/Spn with a counter selection marker, one could select for transformants in which the autonomous element is not stably integrated into the genome. This would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

2.2. Screenable Markers

Screenable markers that may be employed include, but are not limited to, a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta 1988); a beta-lactamase gene (Sutcliffe 1978), which encodes an enzyme for which various chromogenic substrates are known (e.g., PADAC, a chromogenic cephalosporin); a xylE gene (Zukowsky 1983) which encodes a catechol dioxygenase that can convert chromogenic catechols; an □-amylase gene (Ikuta 1990); a tyrosinase gene (Katz 1983) which encodes an enzyme capable of oxidizing tyrosine to DOPA and dopaquinone which in turn condenses to form the easily detectable compound melanin; □-galactosidase gene, which encodes an enzyme for which there are chromogenic substrates; a luciferase (lux) gene (Ow 1986), which allows for bioluminescence detection; or even an aequorin gene (Prasher 1985), which may be employed in calcium-sensitive bioluminescence detection, or a green fluorescent protein gene (Niedz 1995).

Genes from the maize R gene complex are contemplated to be particularly useful as screenable markers. The R gene complex in maize encodes a protein that acts to regulate the production of anthocyanin pigments in most seed and plant tissue. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line is dominant for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening. Where use of a screenable marker gene such as lux or GFP is desired, benefit may be realized by creating a gene fusion between the screenable marker gene and a selectable marker gene, for example, a GFP-NPTII gene fusion. This could allow, for example, selection of transformed cells followed by screening of transgenic plants or seeds.

3. Exemplary DNA Molecules

The invention provides an isolated nucleic acid molecule, e.g., DNA or RNA, comprising a plant nucleotide sequence comprising an open reading frame that is preferentially expressed in a specific plant tissue, i.e., in seeds, roots, green tissue (leaf and stem), panicles or pollen, or is expressed constitutively, or a promoter thereof.

These promoters include, but are not limited to, constitutive, inducible, temporally regulated, developmentally regulated, spatially-regulated, chemically regulated, stress-responsive, tissue-specific, viral and synthetic promoters. Promoter sequences are known to be strong or weak. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter such as the $P_{tac}$ promoter can be induced to varying levels of gene expression depending on the level of isothiopropylgalactoside added to the transformed bacterial cells. An isolated promoter sequence that is a strong promoter for heterologous nucleic acid is advantageous because it provides for a sufficient level of gene expression to allow for easy detection and selection of transformed cells and provides for a high level of gene expression when desired.

Within a plant promoter region there are several domains that are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence that defines the transcription start point for the structural gene.

The presence of the core promoter region defines a sequence as being a promoter: if the region is absent, the promoter is non-functional. Furthermore, the core promoter region is insufficient to provide full promoter activity. A series of regulatory sequences upstream of the core constitute the remainder of the promoter. The regulatory sequences determine expression level, the spatial and temporal pattern of expression and, for an important subset of promoters, expression under inductive conditions (regulation by external factors such as light, temperature, chemicals, hormones).

Regulated expression of the chimeric transacting viral replication protein can be further regulated by other genetic strategies. For example, Cre-mediated gene activation as described by Odell et al. 1990. Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of tissue- and developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al. 1997. Again, either the chimeric tRNA suppressor gene, the chimeric transacting replication gene, or both can be under the control of tissue- and developmental-specific or inducible promoters.

Frequently it is desirable to have continuous or inducible expression of a DNA sequence throughout the cells of an organism in a tissue-independent manner. For example, increased resistance of a plant t6 infection by soil- and air-borne-pathogens might be accomplished by genetic manipulation of the plant's genome to comprise a continuous promoter operably linked to a heterologous pathogen-resistance gene such that pathogen-resistance proteins are continuously expressed throughout the plant's tissues.

Alternatively, it might be desirable to inhibit expression of a native DNA sequence within the seeds of a plant to achieve a desired phenotype. In this case, such inhibition might be accomplished with transformation of the plant to comprise a promoter operably linked to an antisense nucleotide sequence, such that vascular tissue-preferential or vascular tissue-specific expression of the antisense sequence produces an RNA transcript that interferes with translation of the mRNA of the native DNA sequence.

To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins which are easily measured, including, but not limited to, chloramphenicol acetyl transferase (CAT), beta-glucuronidase (GUS), green fluorescent protein (GFP), beta-galactosidase (beta-GAL), and luciferase.

The construct containing the reporter gene under the control of the promoter is then introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography.

The level of enzyme activity corresponds to the amount of enzyme that was made, which in turn reveals the level of expression from the promoter of interest. This level of expression can be compared to other promoters to determine the relative strength of the promoter under study. In order to be sure that the level of expression is determined by the promoter, rather than by the stability of the mRNA, the level of the reporter mRNA can be measured directly, such as by Northern blot analysis.

Once activity is detected, mutational and/or deletional analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then introduced to cells and their activity determined.

In one embodiment, the promoter may be a gamma zein promoter, an oleosin ole16 promoter, a globulins promoter, an actin I promoter, an actin cI promoter, a sucrose synthetase promoter, an INOPS promoter, an EXM5 promoter, a globulin2 promoter, a b-32, ADPG-pyrophosphorylase promoter, an Ltp1 promoter, an Ltp2 promoter, an oleosin ole17 promoter, an oleosin ole18 promoter, an actin 2 promoter, a pollen-specific protein promoter, a pollen-specific pectate lyase promoter, an anther-specific protein promoter, an anther-specific gene RTS2 promoter, a pollen-specific gene promoter, a tapetum-specific gene promoter, tapetum-specific gene RAB24 promoter, a anthranilate synthase alpha subunit promoter, an alpha zein promoter, an anthranilate synthase beta subunit promoter, a dihydrodipicolinate synthase promoter, a Thil promoter, an alcohol dehydrogenase promoter, a cab binding protein promoter, an H3C4 promoter, a RUBISCO SS starch branching enzyme promoter, an ACCase promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphatelphosphotransferase promoter, an ubiquitin promoter, a beta-ketoacyl-ACP synthase promoter, a 33 kDa photosystem 11 promoter, an oxygen evolving protein promoter, a 69 kDa vacuolar ATPase subunit promoter, a metallothionein-like protein promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, an a-tubulin promoter, a cab promoter, a PEPCase promoter, an R gene promoter, a lectin promoter, a light harvesting complex promoter, a heat shock protein promoter, a chalcone synthase promoter, a zein promoter, a globulin-1 promoter, an ABA promoter, an auxin-binding protein promoter, a UDP glucose flavonoid glycosyl-transferase gene promoter, an NTI promoter, an actin promoter, an opaque 2 promoter, a b70 promoter, an oleosin promoter, a CaMV 35S promoter, a CaMV 34S promoter, a CaMV 19S promoter, a histone promoter, a turgor-inducible promoter, a pea small subunit RuBP carboxylase promoter, a Ti plasmid mannopine synthase promoter, Ti plasmid nopaline synthase promoter, a petunia chalcone isomerase promoter, a bean glycine rich protein I promoter, a CaMV 35S transcript promoter, a potato patatin promoter, or a S-E9 small subunit RuBP carboxylase promoter.

4. Transformed (Transgenic) Plants of the Invention and Methods of Preparation

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and ultilane meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Thus, the present invention provides a transformed (transgenic) plant cell, in planta or ex planta, including a transformed plastid or other organelle, e.g., nucleus, mitochondria or chloroplast. The present invention may be used for transformation of any plant species, including, but not limited to, cells from the plant species specified above in the DEFINITION section. Preferably, transgenic plants of the present invention are crop plants and in particular cereals (for example, corn, alfalfa, sunflower, rice, *Brassica*, canola, soybean, barley, soybean, sugarbeet, cotton, safflower, peanut, sorghum, wheat, millet, tobacco, etc.), and even more preferably corn, rice and soybean. Other embodiments of the invention are related to cells, cell cultures, tissues, parts (such as plants organs, leaves, roots, etc.) and propagation material (such as seeds) of such plants.

The transgenic expression cassette of the invention may not only be comprised in plants or plant cells but may advantageously also be containing in other organisms such for example bacteria. Thus, another embodiment of the invention relates to transgenic cells or non-human, transgenic organisms comprising an expression cassette of the invention. Preferred are prokaryotic and eukaryotic organism. Both microorganism and higher organisms are comprised. Preferred microorganism are bacteria, yeast, algae, and fungi. Preferred bacteria are those of the genus *Escherichia, Erwinia, Agrobacterium, Flavobacterium, Alcaligenes, Pseudomonas, Bacillus* or *Cyanobacterim* such as—for example—*Synechocystis* and other bacteria described in Brock Biology of Microorganisms Eighth Edition (pages A-8, A-9, A10 and A11).

Especially preferred are microorganisms capable to infect plants and to transfer DNA into their genome, especially bacteria of the genus *Agrobacterium*, preferably *Agrobacterium tumefaciens* and *rhizogenes*. Preferred yeasts are *Candida, Saccharomyces, Hansenula* and *Pichia*. Preferred Fungi are *Aspergillus, Trichoderma, Ashbya, Neurospora, Fusarium*, and *Beauveria*. Most preferred are plant organisms as defined above.

Transformation of plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the expression cassettes of the invention. The general descriptions of plant expression vectors and reporter genes, and *Agrobacterium* and *Agrobacterium*-mediated gene transfer, can be found in Gruber et al. (1993).

Expression vectors containing genomic or synthetic fragments can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues (Lindsey 1993; Auch & Reth 1990).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti 1985: Byrne 1987; Sukhapinda 1987; Lorz 1985; Potrykus, 1985; Park 1985: Hiei 1994). The use of T-DNA to transform plant cells has received extensive study and is amply described (EP 120516; Hoekema, 1985; Knauf, 1983; and An 1985). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (Fromm 1986) or high velocity ballistic bombardment with metal particles coated with the nucleic acid constructs (Kline 1987, and U.S. Pat. No. 4,945,050). Once transformed, the cells can be regenerated by those skilled in the art. Of particular relevance are the recently described methods to transform foreign genes into commercially important crops, such as rapeseed (De Block 1989), sunflower (Everett 1987), soybean (McCabe 1988; Hinchee 1988; Chee 1989; Christou 1989; EP 301749), rice (Hiei 1994), and corn (Gordon-Kamm 1990; Fromm 1990).

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway 1986), electroporation (Riggs 1986), *Agrobacterium*-mediated transformation (Hinchee 1988), direct gene transfer (Paszkowski 1984), and ballistic particle acceleration using devices available from Agracetus, Inc., Madison, Wis. And BioRad, Hercules, Calif. (see, for example, U.S. Pat. No. 4,945,050; and McCabe 1988). Also see, Weissinger 1988; Sanford 1987 (onion); Christou 1988 (soybean); McCabe 1988 (soybean); Datta 1990 (rice); Klein 1988 (maize); Klein 1988 (maize); Klein 1988 (maize); Fromm 1990 (maize); and Gordon-Kamm 1990 (maize); Svab 1990 (tobacco chloroplast); Koziel 1993 (maize); Shimamoto 1989 (rice); Christou 1991 (rice); European Patent Application EP 0 332 581 (orchardgrass and other Pooideae); Vasil 1993 (wheat); Weeks 1993 (wheat).

In another embodiment, a nucleotide sequence of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al., 1994. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate orthologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab 1990; Staub 1992). This resulted in stable homoplasmic transformants at a frequency of approximately one per 100 bombardments of target leaves. The presence of cloning sites between these markers allowed creation of a plastid targeting vector for introduction of foreign genes (Staub 1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3N-adenyltransferase (Svab 1993). Other selectable markers useful for plastid transformation are known in the art and encompassed within the scope of the invention. Typically, approximately 15-20 cell division cycles following transformation are required to reach a homoplastidic state. Plastid expression, in which genes are inserted by orthologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

Agrobacterium tumefaciens cells containing a vector comprising an expression cassette of the present invention, wherein the vector comprises a Ti plasmid, are useful in methods of making transformed plants. Plant cells are infected with an Agrobacterium tumefaciens as described above to produce a transformed plant cell, and then a plant is regenerated from the transformed plant cell. Numerous Agrobacterium vector systems useful in carrying out the present invention are known. Various Agrobacterium strains can be employed, preferably disarmed Agrobacterium tumefaciens or rhizogenes strains. In a preferred embodiment, Agrobacterium strains for use in the practice of the invention include octopine strains, e.g., LBA4404 or agropine strains, e.g., EHA101 or EHA105. Suitable strains of A. tumefaciens for DNA transfer are for example EHA101[pEHA101] (Hood 1986), EHA105[pEHA105] (Li 1992), LBA4404[pAL4404] (Hoekema 1983), C58C1[pMP90] (Koncz & Schell 1986), and C58C1[pGV2260] (Deblaere 1985). Other suitable strains are Agrobacterium tumefaciens C58, a nopaline strain. Other suitable strains are A. tumefaciens C58C1 (Van Larebeke 1974), A136 (Watson 1975) or LBA4011 (Klapwijk 1980). In another preferred embodiment the soil-borne bacterium is a disarmed variant of Agrobacterium rhizogenes strain K599 (NCPPB 2659). Preferably, these strains are comprising a disarmed plasmid variant of a Ti- or Ri-plasmid providing the functions required for T-DNA transfer into plant cells (e.g., the vir genes). In a preferred embodiment, the Agrobacterium strain used to transform the plant tissue pre-cultured with the plant phenolic compound contains a L,L-succinamopine type Ti-plasmid, preferably disarmed, such as pEHA101. In another preferred embodiment, the Agrobacterium strain used to transform the plant tissue pre-cultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated (Jarschow 1991).

The method of the invention can also be used in combination with particular Agrobacterium strains, to further increase the transformation efficiency, such as Agrobacterium strains wherein the vir gene expression and/or induction thereof is altered due to the presence of mutant or chimeric virA or virG genes (e.g. Hansen 1994; Chen and Winans 1991; Scheeren-Groot, 1994). Preferred are further combinations of Agrobacterium tumefaciens strain LBA4404 (Hiei 1994) with super-virulent plasmids. These are preferably pTOK246-based vectors (Ishida 1996).

A binary vector or any other vector can be modified by common DNA recombination techniques, multiplied in E. coli, and introduced into Agrobacterium by e.g., electroporation or other transformation techniques (Mozo & Hooykaas 1991).

Agrobacterium is grown and used in a manner similar to that described in Ishida (1996). The vector comprising Agrobacterium strain may, for example, be grown for 3 days on YP medium (5 g/l yeast extract, 10 g/l peptone, 5 g/l NaCl, 15 g/l agar, pH 6.8) supplemented with the appropriate antibiotic (e.g., 50 mg/l spectinomycin). Bacteria are collected with a loop from the solid medium and resuspended. In a preferred embodiment of the invention, Agrobacterium cultures are started by use of aliquots frozen at −80° C.

The transformation of the target tissue (e.g., an immature embryo) by the Agrobacterium may be carried out by merely contacting the target tissue with the Agrobacterium. The concentration of Agrobacterium used for infection and co-cultivation may need to be varied. For example, a cell suspension of the Agrobacterium having a population density of approximately from $10^5$ to $10^{11}$, preferably $10^6$ to $10^{10}$, more preferably about $10^8$ cells or cfu/ml is prepared and the target tissue is immersed in this suspension for about 3 to 10 minutes. The resulting target tissue is then cultured on a solid medium for several days together with the Agrobacterium.

Preferably, the bacterium is employed in concentration of $10^6$ to $10^{10}$ cfu/ml. In a preferred embodiment for the co-cultivation step about 1 to 10 µl of a suspension of the soil-borne bacterium (e.g., Agrobacteria) in the co-cultivation medium are directly applied to each target tissue explant and air-dried. This is saving labor and time and is reducing unintended Agrobacterium-mediated damage by excess Agrobacterium usage.

For Agrobacterium treatment, the bacteria are resuspended in a plant compatible co-cultivation medium. Supplementation of the co-culture medium with antioxidants (e.g., silver nitrate), phenol-absorbing compounds (like polyvinylpyrrolidone, Perl 1996) or thiol compounds (e.g., dithiothreitol, L-cysteine, Olhoft 2001) which can decrease tissue necrosis due to plant defence responses (like phenolic oxidation) may further improve the efficiency of Agrobacterium-mediated transformation. In another preferred embodiment, the co-cultivation medium of comprises least one thiol compound, preferably selected from the group consisting of sodium thiolsulfate, dithiotrietol (DTT) and cysteine. Preferably the concentration is between about 1 mM and 10 mM of L-Cysteine, 0.1 mM to 5 mM DTT, and/or 0.1 mM to 5 mM sodium thiolsulfate. Preferably, the medium employed during co-cultivation comprises from about 1 µM to about 10 µM of silver nitrate and from about 50 mg/L to about 1,000 mg/L of L-Cystein. This results in a highly reduced vulnerability of the target tissue against *Agrobacterium*-mediated damage (such as induced necrosis) and highly improves overall transformation efficiency.

Various vector systems can be used in combination with Agrobacteria. Preferred are binary vector systems. Common binary vectors are based on "broad host range"-plasmids like pRK252 (Bevan 1984) or pTJS75 (Watson 1985) derived from the P-type plasmid RK2. Most of these vectors are derivatives of pBIN19 (Bevan 1984). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz 1994). Improved vector systems are described also in WO 02/00900.

Methods using either a form of direct gene transfer or *Agrobacterium*-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, 1982; Bevan 1983), the bar gene which confers resistance to the herbicide phosphinothricin (White 1990, Spencer 1990), the hph gene which confers resistance to the antibiotic hygromycin (Blochlinger & Diggelmann), and the dhfr gene, which confers resistance to methotrexate (Bourouis 1983).

5. Production and Characterization of Stably Transformed Plants

Transgenic plant cells are then placed in an appropriate selective medium for selection of transgenic cells which are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA which has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region which is not native to the gene from which the transcription-initiation-region is derived.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR; "biochemical" assays, such as detecting the presence of a protein product, e.g., by immunological means (ELISAs and Western blots) or by enzymatic function; plant part assays, such as seed assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by polymerase chain reaction (PCR). Using this technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transformants have exogenous genes introduced into different sites in the, genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected, DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer 1992); Laursen 1994) indicating stable inheritance of the gene. The non-chimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays also may take many forms including but not limited to analyzing changes in the chemical composition, morphology, or physiological properties of the plant. Morphological changes may include greater stature or thicker stalks. Most often changes in response of plants or plant parts to imposed treatments are evaluated under carefully controlled conditions termed bioassays.

6. Uses of Transgenic Plants

Once an expression cassette of the invention has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants. The present invention also relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Preferably, the expression cassette in the transgenic plant is sexually transmitted. In one preferred embodiment, the coding sequence is sexually transmitted through a complete normal sexual cycle of the R0 plant to the R1 generation. Additionally preferred, the expression cassette is expressed in the cells, tissues, seeds or plant of a transgenic plant in an amount that is different than the amount in the cells, tissues, seeds or plant of a plant which only differs in that the expression cassette is absent.

The transgenic plants produced herein are thus expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed; increased vitamin, amino acid, and antioxidant content; the production of antibodies (passive immunization) and nutriceuticals), or beneficial to the food processor (e.g., improved processing traits). In such uses, the plants are generally grown for the use of their grain in human or animal foods. Additionally, the use of root-specific promoters in transgenic plants can provide beneficial traits that are localized in the consumable (by animals and humans) roots of plants such as carrots, parsnips, and beets. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules. The transgenic plants may also be used in commercial breeding programs, or may be crossed or bred to plants of related crop species. Improvements encoded by the expression cassette may be transferred, e.g., from maize cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

Thus, the transgenic plants and seeds according to the invention can be used in plant breeding which aims at the development of plants with improved properties conferred by the expression cassette, such as tolerance of drought, disease, or other stresses. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multilane breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines which for example increase the effectiveness of conventional methods such as herbicide or pesticide treatment or allow to dispense with said methods due to their modified genetic properties. Alternatively new crops with improved stress tolerance can be obtained which, due to their optimized genetic "equipment", yield harvested product of better quality than products which were not able to tolerate comparable adverse developmental conditions.

EXAMPLES

Materials and General Methods

Unless indicated otherwise, chemicals and reagents in the Examples were obtained from Sigma Chemical Company (St. Louis, Mo.), restriction endonucleases were from New England Biolabs (Beverly, Mass.) or Roche (Indianapolis, Ind.), oligonucleotides were synthesized by MWG Biotech Inc. (High Point, N.C.), and other modifying enzymes or kits regarding biochemicals and molecular biological assays were from Clontech (Palo Alto, Calif.), Pharmacia Biotech (Piscataway, N.J.), Promega Corporation (Madison, Wis.), or Stratagene (La Jolla, Calif.). Materials for cell culture media were obtained from Gibco/BRL (Gaithersburg, Md.) or DIFCO (Detroit, Mich.). The cloning steps carried out for the purposes of the present invention, such as, for example, restriction cleavages, agarose gel electrophoresis, purification of DNA fragments, transfer of nucleic acids to nitrocellulose and nylon membranes, linking DNA fragments, transformation of *E. coli* cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger (Sanger 1977).

For generating transgenic *Arabidopsis* plants *Agrobacterium tumefaciens* (strain C58C1 [pMP90]) is transformed with the various promoter::GUS vector constructs (see below). Resulting *Agrobacterium* strains are subsequently employed to obtain transgenic plants. For this purpose a isolated transformed *Agrobacterium* colony is incubated in 4 ml culture (Medium: YEB medium with 50 µg/ml Kanamycin and 25 µg/ml Rifampicin) over night at 28° C. With this culture a 400 ml culture of the same medium is inoculated and incubated over night (28° C., 220 rpm). The bacteria a precipitated by centrifugation (GSA-Rotor, 8.000 U/min, 20 min) and the pellet is resuspended in infiltration medium (½ MS-Medium; 0.5 g/l MES, pH 5.8; 50 g/l sucrose). The suspension is placed in a plant box (Duchefa) and 100 ml SILVET L-77 (Osi Specialties Inc., Cat. P030196) are added to a final concentration of 0.02%. The plant box with 8 to 12 Plants is placed into an exsiccator for 10 to 15 min. under vacuum with subsequent, spontaneous ventilation (expansion). This process is repeated 2-3 times. Thereafter all plants are transferred in to pods with wet-soil and grown under long daytime conditions (16 h light; day temperature 22-24° C., night temperature 19° C.; 65% rel. humidity). Seeds are harvested after 6 weeks.

Example 1

Growth Conditions for Plants for Tissue-Specific Expression Analysis

To obtain 4 and 7 days old seedlings, about 400 seeds (*Arabidopsis thaliana* ecotype Columbia) are sterilized with a 80% (v/v) ethanol:water solution for 2 minutes, treated with a sodium hypochlorite solution (0.5% v/v) for 5 minutes, washed three times with distilled water and incubated at 4° C. for 4 days to ensure a standardized germination. Subsequently, seeds are incubated on Petri dishes with MS medium (Sigma M5519) supplemented with 1% sucrose, 0.5 g/l MES (Sigma M8652), 0.8% Difco-BactoAgar (Difco 0140-01), adjusted to pH 5.7. The seedlings are grown under 16 h light/8 h dark cyklus (Philips 58W/33 white light) at 22° C. and harvested after 4 or 7 days, respectively.

To obtain root tissue, 100 seeds are sterilized as described above, incubated at 4° C. for 4 days, and transferred into 250 ml flasks with MS medium (Sigma M5519) supplemented with additional 3% sucrose and 0.5 g/l MES (Sigma M8652), adjusted to pH 5.7 for further growing. The seedlings are grown at a 16 h light/8 h dark cycle (Philips 58W/33 white light) at 22° C. and 120 rpm and harvested after 3 weeks. For all other plant organs employed, seeds are sown on standard soil (Type VM, Manna-Italia, Via S. Giacomo 42, 39050 San Giacomo/Laives, Bolzano, Italien), incubated for 4 days at 4° C. to ensure uniform germination, and subsequently grown under a 16 h light/8 darkness regime (OSRAM Lumi-lux Daylight 36W/12) at 22° C. Young rosette leaves are harvested at the 8-leaf stage (after about 3 weeks), mature rosette leaves are harvested after 8 weeks briefly before stem formation. Apices of out-shooting stems are harvested briefly after out-shooting. Stem, stem leaves, and flower buds are harvested in development stage 12 (Bowmann J (ed.), *Arabidopsis*, Atlas of Morphology, Springer New York, 1995) prior to stamen development. Open flowers are harvested in development stage 14 immediately after stamen development. Wilting flowers are harvested in stage 15 to 16. Green and yellow shoots used for the analysis have a length of 10 to 13 mm.

Example 2

Demonstration of Expression Profile

To demonstrate and analyze the transcription regulating properties of a promoter of the useful to operably link the promoter or its fragments to a reporter gene, which can be employed to monitor its expression both qualitatively and quantitatively. Preferably bacterial β-glucuronidase is used (Jefferson 1987). β-glucuronidase activity can be monitored in planta with chromogenic substrates such as 5-bromo-4-Chloro-3-indolyl-β-D-glucuronic acid during corresponding activity assays (Jefferson 1987). For determination of promoter activity and tissue specificity plant tissue is dissected, embedded, stained and analyzed as described (e.g., Bäumlein 1991).

For quantitative β-glucuronidase activity analysis MUG (methylumbelliferyl glucuronide) is used as a substrate, which is converted into MU (methylumbelliferone) and glucuronic acid. Under alkaline conditions this conversion can be quantitatively monitored fluorometrically (excitation at 365 nm, measurement at 455 nm; SpectroFluorimeter Thermo Life Sciences Fluoroscan) as described (Bustos 1989).

Example 3

Cloning of the Promoter Fragments

To isolate the promoter fragments described by SEQ ID NO: 1, 2, 3, 4, 5, 8, 9, 10, 11, 12, 13, 14, 15, 18, 19, 20, 21, 22, 23, 24, 25, 28, 29, 30, 31, 32, 33, 34, 35, 38, 39, 40, 41, 42, 43, 44, and 45 genomic DNA is isolated from *Arabidopsis thaliana* (ecotype Columbia) as described (Galbiati 2000). The isolated genomic DNA is employed as matrix DNA for a polymerase chain reaction (PCR) mediated amplification using the oligonucleotide primers and protocols indicated below (Table 3).

TABLE 3

PCR oligonucleotide primers for amplification of the various transcription regulating nucleotide sequences and restriction enzymes for modifying the resulting PCR products

| SEQ ID | Promoter | Forward Primer | Reverse Primer | Restriction enzymes |
|---|---|---|---|---|
| SEQ ID NO: 1 | pSUK416 | SUK416for SEQ ID NO: 48 | SUK416rev SEQ ID NO: 49 | SpeI/NcoI |
| SEQ ID NO: 2 | pSUK416GB | SUK416for SEQ ID NO: 48 | SUK416rev SEQ ID NO: 49 | SpeI/NcoI |
| SEQ ID NO: 3 | pSUK418 | SUK418for SEQ ID NO: 50 | SUK418rev SEQ ID NO: 51 | SpeI/NcoI |
| SEQ ID NO: 4 | pSUK418GB | SUK418for SEQ ID NO: 50 | SUK418rev SEQ ID NO: 51 | SpeI/NcoI |
| SEQ ID NO: 5 | pSUK418LGB | SUK418Lfor SEQ ID NO: 52 | SUK418Lrev SEQ ID NO: 53 | BamHI/NcoI |
| SEQ ID NO: 8 | pSUK420L | SUK420for SEQ ID NO: 54 | SUK420Lrev SEQ ID NO: 55 | EcoRI/NcoI |
| SEQ ID NO: 9 | pSUK420LGB | SUK420for SEQ ID NO: 54 | SUK420Lrev SEQ ID NO: 55 | EcoRI/NcoI |
| SEQ ID NO: 10 | pSUK420S | SUK420for SEQ ID NO: 54 | SUK420Srev SEQ ID NO: 56 | EcoRI/NcoI |
| SEQ ID NO: 11 | pSUK420SGB | SUK420for SEQ ID NO: 54 | SUK420Srev SEQ ID NO: 56 | EcoRI/NcoI |
| SEQ ID NO: 12 | pSUK422L | SUK422for SEQ ID NO: 57 | SUK422Lrev SEQ ID NO: 58 | BamHI/NcoI |
| SEQ ID NO: 13 | pSUK422LGB | SUK422for SEQ ID NO: 57 | SUK422Lrev SEQ ID NO: 58 | BamHI/NcoI |
| SEQ ID NO: 14 | pSUK422S | SUK422for SEQ ID NO: 57 | SUK422Srev SEQ ID NO: 59 | BamHI/NcoI |
| SEQ ID NO: 15 | pSUK422SGB | SUK422for SEQ ID NO: 57 | SUK422Srev SEQ ID NO: 59 | BamHI/NcoI |
| SEQ ID NO: 18 | pSUK424L | SUK424for SEQ ID NO: 60 | SUK424Lrev SEQ ID NO: 61 | EcoRI/NcoI |
| SEQ ID NO: 19 | pSUK424LGB | SUK424for SEQ ID NO: 60 | SUK424Lrev SEQ ID NO: 61 | EcoRI/NcoI |
| SEQ ID NO: 20 | pSUK424S | SUK424for SEQ ID NO: 60 | SUK424Srev SEQ ID NO: 62 | EcoRI/NcoI |
| SEQ ID NO: 21 | pSUK424SGB | SUK424for SEQ ID NO: 60 | SUK424Srev SEQ ID NO: 62 | EcoRI/NcoI |
| SEQ ID NO: 22 | pSUK426L | SUK426for SEQ ID NO: 63 | SUK426Lrev SEQ ID NO: 64 | BamHI/NcoI |
| SEQ ID NO: 23 | pSUK426LGB | SUK426for SEQ ID NO: 63 | SUK426Lrev SEQ ID NO: 64 | BamHI/NcoI |
| SEQ ID NO: 24 | pSUK426S | SUK426for SEQ ID NO: 63 | SUK426Srev SEQ ID NO: 65 | BamHI/NcoI |
| SEQ ID NO: 25 | pSUK426SGB | SUK426for SEQ ID NO: 63 | SUK426Srev SEQ ID NO: 65 | BamHI/NcoI |
| SEQ ID NO: 28 | pSUK428L | SUK428for SEQ ID NO: 66 | SUK428Lrev SEQ ID NO: 67 | SpeI/NcoI |
| SEQ ID NO: 29 | pSUK428LGB | SUK428for SEQ ID NO: 66 | SUK428Lrev SEQ ID NO: 67 | SpeI/NcoI |
| SEQ ID NO: 30 | pSUK428S | SUK428for SEQ ID NO: 66 | SUK428Srev SEQ ID NO: 68 | SpeI/NcoI |
| SEQ ID NO: 31 | pSUK428SGB | SUK428for SEQ ID NO: 66 | SUK428Srev SEQ ID NO: 68 | SpeI/NcoI |
| SEQ ID NO: 32 | pSUK430L | SUK430for SEQ ID NO: 69 | SUK430Lrev SEQ ID NO: 70 | SpeI/NcoI |
| SEQ ID NO: 33 | pSUK430LGB | SUK430for SEQ ID NO: 69 | SUK430Lrev SEQ ID NO: 70 | SpeI/NcoI |
| SEQ ID NO: 34 | pSUK430S | SUK430for SEQ ID NO: 69 | SUK430Srev SEQ ID NO: 71 | SpeI/NcoI |
| SEQ ID NO: 35 | pSUK430SGB | SUK430for SEQ ID NO: 69 | SUK430Srev SEQ ID NO: 71 | SpeI/NcoI |
| SEQ ID NO: 38 | pSUK436L | SUK436for SEQ ID NO: 72 | SUK436Lrev SEQ ID NO: 73 | BamHI/NcoI |
| SEQ ID NO: 39 | pSUK436LGB | SUK436for SEQ ID NO: 72 | SUK436Lrev SEQ ID NO: 73 | BamHI/NcoI |
| SEQ ID NO: 40 | pSUK436S | SUK436for SEQ ID NO: 72 | SUK436Srev SEQ ID NO: 74 | BamHI/NcoI |
| SEQ ID NO: 41 | pSUK436SGB | SUK436for SEQ ID NO: 72 | SUK436Srev SEQ ID NO: 74 | BamHI/NcoI |
| SEQ ID NO: 42 | pSUK438L | SUK438for SEQ ID NO: 75 | SUK438Lrev SEQ ID NO: 76 | BamHI/NcoI |
| SEQ ID NO: 43 | pSUK438LGB | SUK438for SEQ ID NO: 75 | SUK438Lrev SEQ ID NO: 76 | BamHI/NcoI |
| SEQ ID NO: 44 | pSUK438S | SUK438for SEQ ID NO: 75 | SUK438Srev SEQ ID NO: 77 | BamHI/NcoI |

TABLE 3-continued

PCR oligonucleotide primers for amplification of the various transcription regulating nucleotide sequences and restriction enzymes for modifying the resulting PCR products

| SEQ ID | Promoter | Forward Primer | Reverse Primer | Restriction enzymes |
|---|---|---|---|---|
| SEQ ID NO: 45 | pSUK438SGB | SUK438for SEQ ID NO: 75 | SUK438Srev SEQ ID NO: 77 | BamHI/NcoI |

Amplification is carried out as follows:
100 ng genomic DNA
1×PCR buffer
2.5 mM $MgCl_2$,
200 μM each of dATP, dCTP, dGTP und dTTP
10 pmol of each oligonucleotide primers
2.5 Units Pfu DNA Polymerase (Stratagene)
in a final volume of 50 μl The following temperature program is employed for the various amplifications (BIORAD Thermocycler):
1. 95° C. for 5 min
2. 54° C. for 1 min, followed by 72° C. for 5 min and 95° C. for 30 sec. Repeated 25 times.
3. 54° C. for 1 min, followed by 72° C. for 10 min.
4. Storage at 4° C.

The resulting PCR-products are digested with the restriction endonucleases specified in the Table above (Table 3) and cloned into the vector pSUN0301 (SEQ ID NO: 78) (pre-digested with the same enzymes) upstream and in operable linkage to the glucuronidase (GUS) gene. Following stable transformation of each of these constructs into *Arabidopsis thaliana* tissue specificity and expression profile was analyzed by a histochemical and quantitative GUS-assay, respectively.

Example 4

Expression Profile of the Various Promoter::GUS Constructs in Stably Transformed *A. thaliana* Plants 4.1 pSUK416, pSUK416 GB, pSUK418, pSUK418 GB, pSUK418LGB This vascular tissue-specific promoter is mainly active in the parenchymatic cells of the xylem. Activity is stronger in above ground organs but also detectable in roots. GUS expression driven by this promoter was detected in all organs of seedlings and adult plants tested and includes leaf veins of lower order.

4.2 pSUK420, pSUK420 GB, pSUK422, pSUK422 GB

Strong vascular tissue-specific expression is conferred by this promoter in all organs of seedlings and adult plants analyzed. Expression is not confined to parenchymatic cells of xylem but was also detectable in the phloem. The promoter is active in leave veins including vessels of the lowest order.

4.3 pSUK424L, pSUK424LGB, pSUK424S, pSUK424SGB, pSUK426L, pSUK426LGB, pSUK426S, pSUK426SGB

This vascular tissue-specific promoter is mainly active in the parenchymatic cells of the xylem. The tissue-specific activity is strong in all organs of seedlings and adult plants analyzed. The promoter is stronger in leave veins of higher order than in their lower order counterparts.

4.4 pSUK428L, pSUK428LGB, pSUK428S, pSUK428SGB, pSUK430L, pSUK 30LGB, pSUK430S, pSUK430SGB

This vascular tissue-specific promoter is mainly active in the parenchymatic cells of the xylem but weaker activity was also detected in the phloem. The promoter is active in all organs of seedlings and adult plants analyzed. Lower order leave veins revealed somewhat weaker promoter strength than veins of higher order.

4.5 pSUK436L, pSUK436LGB, pSUK436S, pSUK436SGB, pSUK438L, pSUK438L_GB, pSUK438S, pSUK438SGB

The activity of this vascular tissue-specific promoter is confined to above ground organs. It is mainly active in the parenchymatic tissue of the xylem. Leave veins of higher as well as of lower order revealed reporter gene expression driven by the promoter.

Example 5

Vector Construction for Overexpression and Gene "Knockout" Experiments 5.1 Overexpression Vectors used for expression of full-length "candidate genes" of interest in plants (overexpression) are designed to overexpress the protein of interest and are of two general types, biolistic and binary, depending on the plant transformation method to be used.

For biolistic transformation (biolistic vectors), the requirements are as follows:
1. a backbone with a bacterial selectable marker (typically, an antibiotic resistance gene) and origin of replication functional in *Escherichia coli* (*E. coli*; e.g., ColE1), and
2. a plant-specific portion consisting of:
   a. a gene expression cassette consisting of a promoter (eg. ZmUBlint MOD), the gene of interest (typically, a full-length cDNA) and a transcriptional terminator (e.g., *Agrobacterium tumefaciens* nos terminator);
   b. a plant selectable marker cassette, consisting of a suitable promoter, selectable marker gene (e.g., D-amino acid oxidase; dao1) and transcriptional terminator (eg. nos terminator).

Vectors designed for transformation by *Agrobacterium tumefaciens* (*A. tumefaciens*; binary vectors) consist of:
1. a backbone with a bacterial selectable marker functional in both *E. coli* and *A. tumefaciens* (e.g., spectinomycin resistance mediated by the aadA gene) and two origins of replication, functional in each of aforementioned bacterial hosts, plus the *A. tumefaciens* virG gene;
2. a plant-specific portion as described for biolistic vectors above, except in this instance this portion is flanked by *A. tumefaciens* right and left border sequences which mediate transfer of the DNA flanked by these two sequences to the plant.

5.2 Gene Silencing Vectors

Vectors designed for reducing or abolishing expression of a single gene or of a family or related genes (gene silencing vectors) are also of two general types corresponding to the methodology used to down-regulate gene expression: antisense or double-stranded RNA interference (dsRNAi).

(a) Anti-Sense

For antisense vectors, a full-length or partial gene fragment (typically, a portion of the cDNA) can be used in the same vectors described for full-length expression, as part of the gene expression cassette. For antisense-mediated down-regulation of gene expression, the coding region of the gene or gene fragment will be in the opposite orientation relative to the promoter; thus, mRNA will be made from the non-coding (antisense) strand in planta.

(b) dsRNAi

For dsRNAi vectors, a partial gene fragment (typically, 300 to 500 base pairs long) is used in the gene expression cassette, and is expressed in both the sense and antisense orientations, separated by a spacer region (typically, a plant intron, eg. the OsSH1 intron 1, or a selectable marker, eg. conferring kanamycin resistance). Vectors of this type are designed to form a double-stranded mRNA stem, resulting from the base pairing of the two complementary gene fragments in planta.

Biolistic or binary vectors designed for overexpression or knockout can vary in a number of different ways, including e.g., the selectable markers used in plant and bacteria, the transcriptional terminators used in the gene expression and plant selectable marker cassettes, and the methodologies used for cloning in gene or gene fragments of interest (typically, conventional restriction enzyme-mediated or Gateway™ recombinase-based cloning).

REFERENCES

1. Abel et al., Science, 232:738 (1986).
2. Altschul et al., Nucleic Acids Res., 25:3389 (1997).
3. Altschul et al., J. Mol. Biol., 215:403 (1990).
4. An et al., EMBO J., 4:277 (1985).
5. Auch & Reth, Nucleic Acids Research, 18:6743 (1990).
6. Ausubel et al. (1987) Current Protocols in Molecular Biology, Greene Publishing Assoc. and Wiley Interscience
7. Ballas et al., Nucleic Acids Res., 17:7891 (1989).
8. Barkai-Golan et al., Arch. Microbiol., 116:119 (1978).
9. Batzer et al., Nucleic Acid Res., 19:5081 (1991).
10. Bäumlein et al. Mol Gen Genet 225:121-128 (1991)
11. Becker et al. (1994) Plant J., 5:299-307,
12. Bernal-Lugo and Leopold, Plant Physiol., 98:1207 (1992).
13. Bevan et al., Nature, 304:184 (1983).
14. Bevan et al., Nucl. Acids Res., 11:369 (1983).
15. Bevan, Nucl. Acids Res., 12:8711 (1984).
16. Blackman et al., Plant Physiol., 100:225 (1992).
17. Blochlinger & Diggelmann, Mol Cell Biol, 4:2929 (1984).
18. Bol et al., Ann. Rev. Phytopath., 28:113 (1990).
19. Bouchez et al., EMBO J., 8:4197 (1989).
20. Bourouis et al., EMBO J., 2:1099 (1983).
21. Bowler et al., Ann. Rev. Plant Physiol., 43:83 (1992).
22. Branson and Guss, Proc. North Central Branch Entomological Society of America (1972).
23. Broakgert et al., Science, 245:110 (1989).
24. Bustos M M et al. (1989) Plant Gell 1:839-853
25. Byrne et al. Plant Cell Tissue and Organ Culture, 8:3 (1987).
26. Callis et al., Genes and Develop., 1:1183 (1987).
27. Campbell and Gowri, Plant Physiol., 92:1 (1990).
28. Campbell, W. C., ed. Ivermectin and Abamectin, Springer-Verlag, New York, 1989.
29. Chaves M M & Oliveira M M (2004) J Exp Bot 55 (407): 2365-2384.
30. Chee et al. Plant Physiol., 91:1212 (1989).
31. Chen and Winans (1991) J. Bacteriol. 173: 1139-1144
32. Christou et al. Proc. Natl. Acad. Sci USA, 86:7500 (1989).
33. Christou et al., Biotechnology, 9:957 (1991).
34. Christou et al., Plant Physiol., 87:671 (1988).
35. Chui et al. (1996) Curr Biol 6:325-330
36. Coe et al., In: Corn and Corn Improvement, Sprague et al. (eds.) pp. 81-258 (1988).
37. Corpet et al. Nucleic Acids Res., 16:10881 (1988).
38. Coxson et al., Biotropica, 24:121 (1992).
39. Crameri et al., Nature Biotech., 15:436 (1997).
40. Crameri et al., Nature, 391:288 (1998).
41. Crossway et al., BioTechniques, 4:320 (1986).
42. Cuozzo et al., BioTechnology, 6:549 (1988).
43. Cutler et al., J. Plant Physiol., 135:351 (1989).
44. Czapla and Lang, J. Econ. Entomol., 83:2480 (1990).
45. Datta et al., Bio/Technology, 8:736 (1990).
46. Davies et al., Plant Physiol., 93:588 (1990).
47. Dayhoff et al., Atlas of Protein Sequence and Structure, Natl. Biomed. Res. Found., Washington, D.C. (1978).
48. De Blaere et al., Meth. Enzymol., 143:277 (1987).
49. De Block et al. Plant Physiol., 91:694 (1989).
50. De Block et al., EMBO Journal, 6:2513 (1987).
51. Deblaere et al. Nucl Acids Res 13:4777-4788 (1985)
52. Decroocq V et al. (2001) Acta Horticulturae 550 (2) 397-403.
53. Della-Cioppa et al. Bio/Technology 5:579-584 (1987)
54. Della-Cioppa et al., Plant Physiology, 84:965-968 (1987).
55. Dellaporta et al., in Chromosome Structure and Function, Plenum Press, 263-282 (1988).
56. Depicker et al., Plant Cell Reports, 7:63 (1988).
57. Dunn et al., Can. J. Plant Sci., 61:583 (1981).
58. Dure et al., Plant Mol. Biol., 12:475 (1989).
59. Ebinuma et al. Proc Natl Acad Sci USA 94:2117-2121 (2000a)
60. Ebinuma et al. Selection of Marker-free transgenic plants using the oncogenes (ipt, rol A, B, C) of *Agrobacterium* as selectable markers, In Molecular Biology of Woody Plants. Kluwer Academic Publishers (2000b)
61. Eichholtz et al. Somatic Cell and Molecular Genetics 13, 67-76 (1987)
62. Ellis et al., EMBO Journal, 6:3203 (1987).
63. Elroy-Stein et al., Proc. Natl. Acad. Sci. U.S.A., 86:6126 (1989).
64. English et al., Plant Cell, 8:179 (1996).
65. Erdmann et al., J. Gen. Microbiol., 138:363 (1992).
66. Erikson et al. Nat Biotechnol. 22(4):455-8 (2004)
67. Everett et al., Bio/Technology, 5:1201(1987).
68. Fedoroff N V & Smith D L Plant J 3:273-289 (1993)
69. Fire A et al Nature 391:806-811 (1998)
70. Fitzpatrick, Gen. Engineering News, 22:7 (1993).
71. Fraley et al. Proc Natl Acad Sci USA 80:4803 (1983)
72. Fromm et al., Bio/Technology, 8:833 (1990).
73. Fromm et al., Nature (London), 319:791 (1986).
74. Galbiati et al. Funct. Integr Genozides 2000, 20 1:25-34
75. Gallie et al. Nucl Acids Res 15:8693-8711 (1987)
76. Gallie et al., Nucleic Acids Res., 15:3257 (1987).
77. Gallie et al., The Plant Cell, 1:301 (1989).
78. Gan et al., Science, 270:1986 (1995).
79. Gatehouse et al., J. Sci. Food Agric., 35:373 (1984).
80. Gelfand, eds., PCR Strategies Academic Press, New York (1995).

81. Gelvin et al., Plant Molecular Biology Manual, (1990).
82. Gittins J R et al. (2003) TRANSGENIC RESEARCH 12 (4): 391-402.
83. Gleave et al. Plant Mol. Biol. 40(2):223-35 (1999)
84. Gordon-Kamm et al., Plant Cell, 2:603 (1990).
85. Goring et al, PNAS, 88:1770 (1991).
86. Gruber, et al., Vectors for Plant Transformation, in: Methods in Plant Molecular Biology & Biotechnology" in Glich et al., (Eds; pp. 89-119, CRC Press, 1993).
87. Guerineau et al., Mol. Gen. Genet., 262:141 (1991).
88. Guerrero et al., Plant Mol. Biol., 15:11 (1990).
89. Gupta et al., PNAS, 90:1629 (1993).
90. Haines and Higgins (eds.), Nucleic Acid Hybridization, IRL Press, Oxford, U.K.
91. Hajdukiewicz et al. Plant Mol Biol 25:989-994 (1994)
92. Hammock et al., Nature, 344:458 (1990).
93. Hansen et al. Proc. Natl. Acad. Sci. USA 91:7603-7607 (1994)
94. Hayford et al. Plant Physiol. 86:1216 (1988)
95. Hemenway et al., EMBO Journal, 7:1273 (1988).
96. Henikoff & Henikoff, Proc. Natl. Acad. Sci. USA, 89:10915 (1989).
97. Hiei et al. Plant J 6: 271-282 (1994)
98. Higgins et al., Gene, 73:237 (1988).
99. Higo et al. (1999) Nucl Acids Res 27(1): 297-300
100. Hilder et al., Nature, 330:160 (1987).
101. Hille et al. Plant Mol. Biol. 7:171 (1986)
102. Hinchee et al. Bio/Technology 6:915 (1988).
103. Hoekema et al. (1983) Nature 303:179-181
104. Hoekema, In: The Binary Plant Vector System. Offsetdrukkerij Kanters B. V.; Alblasserdam (1985).
105. Hood et al. J Bacteriol 168:1291-1301 (1986)
106. Huang et al., CABIOS, 8:155 (1992).
107. Ikeda et al., J. Bacteriol., 169:5612 (1987).
108. Ikuta et al., Biotech., 8:241 (1990).
109. Ingelbrecht et al., Plant Cell, 1:671 (1989).
110. Innis and Gelfand, eds., PCR Methods Manual (Academic Press, New York) (1999).
111. Innis et al., eds., PCR Protocols: A Guide to Methods and Applications (Academic Press, New York (1995).
112. Innis et al., PCR Protocols: A Guide to Methods and Applications, Academic Press, Inc., San Diego, Calif. (1990).
113. Ishida Y et al. Nature Biotech 745-750 (1996)
114. Jefferson et al. EMBO J. 6:3901-3907 (1987)
115. Jefferson et al. Plant Mol Biol Rep 5:387-405 (1987)
116. Jenes B et al. Techniques for Gene Transfer, in: Recombinant Plants, Vol. 1, Engineering and Utilization, edited by S D Kung and R Wu, Academic Press, pp. 128-143 (1993)
117. Jobling et al., Nature, 325:622 (1987).
118. Johnson et al., PNAS USA, 86:9871 (1989)
119. Jones et al. Mol. Gen. Genet., 210:86 (1987).
120. Joshi et al., Nucleic Acid Res., 15:9627 (1987).
121. Kaasen et al., J. Bacteriol., 174:889 (1992).
122. Karlin and Altschul, Proc. Natl. Acad. Sci. USA, 87:2264 (1990).
123. Karlin and Altschul, Proc. Natl. Acad. Sci. USA, 90:5873 (1993).
124. Karsten et al., Botanica Marina, 35:11 (1992).
125. Katz et al., J. Gen. Microbiol., 129:2703 (1983).
126. Keller et al., EMBO Journal, 8:1309 (1989).
127. Keller et al., Genes Dev., 3:1639 (1989).
128. Klapwijk et al. J. Bacteriol., 141,128-136 (1980)
129. Klein et al., Bio/Technoloy, 6:559 (1988).
130. Klein et al., Plant Physiol., 91:440 (1988).
131. Klein et al., Proc. Natl. Acad. Sci. USA, 85:4305 (1988).
132. Knauf, et al., Genetic Analysis of Host Range Expression by *Agrobacterium* In: Molecular Genetics of the Bacteria-Plant Interaction, Puhler, A. ed., Springer-Verlag, New York, 1983.
133. Koncz & Schell Mol Gen Genet 204:383-396 (1986)
134. Koprek T et al. Plant J 19(6): 719-726 (1999)
135. Koster and Leopold, Plant Physiol., 88:829 (1988).
136. Koziel et al., Biotechnology, 11:194 (1993).
137. Kunkel et al., Methods in Enzymol., 154:367 (1987).
138. Kunkel, Proc. Natl. Acad. Sci. USA, 82:488 (1985).
139. Lam E und Chua N H, J Biol Chem; 266(26):17131-17135 (1991)
140. Laufs et al., PNAS, 87:7752 (1990).
141. Lawton et al., Mol. Cell Biol., 7:335 (1987).
142. Lee and Saier, J. Bacteriol., 153 (1982).
143. Leffel et al. Biotechniques 23(5):912-8 (1997)
144. Lescot et al. Nucleic Acids Res 30(1):325-7 (2002)
145. Li et al. Plant Mol Biol 20:1037-1048 (1992)
146. Lindsey et al., Transgenic Research, 2:3347 (1993).
147. Liu et al., Plant J. 8, 457-463 (1995)
148. Liu Z Z et al. (2003) Planta 216 (5): 824-833.
149. Lommel et al., Virology, 181:382 (1991).
150. Loomis et al., J. Expt. Zool., 252:9 (1989).
151. Lorz et al., Mol. Gen. Genet., 199:178 (1985).
152. Ma et al., Nature, 334:631 (1988).
153. Macejak et al., Nature, 353:90 (1991).
154. Maki et al., Methods in Plant Molecular Biology & Biotechnology, Glich et al., 67-88 CRC Press, (1993).
155. Maniatis T, Fritsch E F, and Sambrook J Molecular Cloning: A Laboratory Manual, Cold Spring Harbor Laboratory, Cold Spring Harbor (N.Y.), (1989)
156. Matzke et al. (2000) Plant Mol Biol 43:401-415;
157. McBride et al., PNAS USA, 91:7301 (1994).
158. McCabe et al., Bio/Technology, 6:923 (1988).
159. Meinkoth and Wahl, Anal. Biochem., 138:267 (1984).
160. Messing and Vierra, Gene, 19:259 (1982).
161. Michael et al., J. Mol. Biol., 26:585 (1990). (im Text steht: Michael et al. 1994)
162. Millar et al. Plant Mol Biol Rep 10:324-414 (1992)
163. Mogen et al., Plant Cell, 2:1261 (1990).
164. Moore et al., J. Mol. Biol., 272:336 (1997).
165. Mozo & Hooykaas Plant Mol. Biol. 16:917-918 (1991)
166. Mundy and Chua, EMBO J., 7:2279 (1988).
167. Munroe et al., Gene, 91:151 (1990).
168. Murakami et al., Mol. Gen. Genet., 205:42 (1986).
169. Murata et al., FEBS Lett., 296:187 (1992).
170. Murdock et al., Phytochemistry, 29:85 (1990).
171. Murray et al., Nucleic Acids Res., 17:477 (1989).
172. Myers and Miller, CABIOS, 4:11 (1988).
173. Naested H Plant J 18:571-576 (1999)
174. Napoli et al., Plant Cell, 2:279 (1990).
175. Needleman and Wunsch, J. Mol. Biol., 48:443-453 (1970).
176. Nehra et al. Plant J. 5:285-297 (1994)
177. Niedz et al., Plant Cell Reports, 14:403 (1995).
178. Odell et al., Mol. Gen. Genet., 113:369 (1990).
179. Odell et al., Nature, 313:810 (1985).
180. Ohtsuka et al., J. Biol. Chem., 260:2605 (1985)
181. Olhoft et al. Plant Cell Rep 20: 706-711 (2001)
182. Ow et al., Science, 234:856 (1986).
183. Pacciotti et al., Bio/Technology, 3:241 (1985).
184. Park et al., J. Plant Biol., 38:365 (1985).
185. Paszkowski et al., EMBO J., 3:2717 (1984).
186. Pearson and Lipman, Proc. Natl. Acad. Sci., 85:2444 (1988).
187. Pearson et al., Meth. Mol. Biol., 24:307 (1994).
188. Perera R J et al. Plant Mol. Biol. 23(4): 793-799 (1993)

189. Perlak et al., Proc. Natl. Acad. Sci. USA, 88:3324 (1991).
190. Phillips et al., In Corn & Corn Improvement, 3rd Edition 10 Sprague et al. (Eds. pp. 345-387)(1988).
191. Phi-Van et al., Mol. Cell. Biol., 10:2302 (1990).
192. Piatkowski et al., Plant Physiol., 94:1682 (1990).
193. Potrykus et al., Mol. Gen. Genet., 199:183 (1985).
194. Potrykus, Trends Biotech., 7:269 (1989).
195. Prasher et al., Biochem. Biophys. Res. Comm., 126: 1259 (1985).
196. Proudfoot, Cell, 64:671 (1991).
197. Ramos PL et al. (2004) Virus Research 102 (2): 125-132.
198. Reed et al., J. Gen. Microbiol., 130:1 (1984).
199. Riggs et al., Proc. Natl. Acad. Sci. USA, 83:5602 (1986).
200. Rossolini et al., Mol. Cell. Probes, 8:91 (1994).
201. Ruiz, Plant Cell, 10:937 (1998).
202. Sambrook et al., Molecular Cloning: A Laboratory Manual (2d ed., Cold Spring Harbor Laboratory Press, Plainview, N.Y.) (1989).
203. Sanfacon et al., Genes Dev., 5:141 (1991).
204. Sanford et al., Particulate Science and Technology, 5:27 (1987).
205. Scheeren-Groot et al. J. Bacteriol 176: 6418-6426 (1994)
206. Schenborn and Groskreutz Mol Biotechnol 13(1): 29-44 (1999)
207. Schlaman and Hooykaas Plant J 11:1377-1385 (1997)
208. Schoffl F et al. (1989) Mol Gen Genetics 217(2-3):246-53
209. Shagan et al., Plant Physiol., 101:1397 (1993).
210. Shah et al. Science 233: 478 (1986)
211. Shapiro, Mobile Genetic Elements, Academic Press, N.Y. (1983).
212. Shimamoto et al., Nature, 338:274 (1989).
213. Silhavy T J, Berman M L, and Enquist L W Experiments with Gene Fusions, Cold Spring Harbor Laboratory Press, Cold Spring Harbor (NY), (1984)
214. Skuzeski et al., Plant Molec. Biol. 15: 65-79 (1990).
215. Smith et al., Adv. Appl. Math., 2:482.(1981).
216. Smith et al., Mol. Gen. Genet., 224:447 (1990).
217. Sobeih W Y et al. (2004) J Exp Bot 55 (407): 2353-2363.
218. Spencer et al., Theor. Appl. Genet, 79:625 (1990). Spencer 1992 Referenz fehlt
219. Stalker et al., Science, 242:419 (1988).
220. Staub et al., EMBO J., 12:601 (1993).
221. Staub et al., Plant Cell, 4:39 (1992).
222. Steifel et al., The Plant Cell, 2:785 (1990).
223. Stemmer, Nature, 370:389 (1994).
224. Stemmer, Proc. Natl. Acad. Sci. USA, 91:10747 (1994).
225. Stief et al., Nature, 341:343 (1989).
226. Stougaard Plant J 3:755-761 (1993)
227. Sukhapinda et al., Plant Mol. Biol., 8:209 (1987).
228. Sundaresan et al. Gene Develop 9: 1797-1810 (1995)
229. Sutcliffe, PNAS USA, 75:3737 (1978).
230. Svab et al., Plant Mol. Biol. 14:197 (1990)
231. Svab et al., Proc. Natl. Acad. Sci. USA, 87:8526 (1990).
232. Svab et al., Proc. Natl. Acad. Sci. USA, 90:913 (1993).
233. Tarczynski et al., PNAS USA, 89:2600 (1992).
234. Thillet et al., J. Biol. Chem., 263:12500 (1988).
235. Tijssen, Laboratory Techniques in Biochemistry and Molecular Biology-Hybridization with Nucleic Acid Probes, Elsevier, N.Y. (1993).
236. Tomes et al., Plant Cell, Tissue and Organ Culture: Fundamental Methods, Springer Verlag, Berlin (1995).
237. Tomic et al., NAR, 12:1656 (1990).
238. Turner et al., Molecular Biotechnology, 3:225 (1995).
239. Twell et al., Plant Physiol., 91:1270 (1989).
240. Ugaki et al., Nucl. Acids Res., 19:371 (1991).
241. Ulmasov et al., Plant Mol: Biol., 35:417 (1997).
242. Upender et al., Biotechniques, 18:29 (1995).
243. van der Krol et al., Plant Cell, 2:291 (1990).
244. Vanden Elzen et al. Plant Mol. Biol. 5:299 (1985)
245. Vasil et al. Bio/Technology, 10:667-674 (1992)
246. Vasil et al. Bio/Technology, 11:1153-1158 (1993)
247. Vasil et al., Mol. Microbiol., 3:371 (1989).
248. Vasil et al., Plant Physiol., 91:1575 (1989).
249. Vernon and Bohnert, EMBO J., 11:2077 (1992).
250. Walker and Gaastra, eds., Techniques in Molecular Biology, MacMillan Publishing Company, New York (1983).
251. Wan & Lemaux (1994) Plant Physiol., 104:3748
252. Wang et al., Mol. Cell. Biol., 12:3399 (1992).
253. Waterman, M. S. Introduction to Computational Biology: Maps, sequences and genomes. Chapman & Hall. London (1995).
254. Watrud et al., in Engineered Organisms and the Environment (1985).
255. Watson et al. J. Bacteriol 123, 255-264 (1975)
256. Watson et al., Corn: Chemistry and Technology (1987).
257. Weeks et al. Plant Physiol 102:1077-1084 (1993)
258. Weissinger et al., Annual Rev. Genet., 22:421 (1988).
259. White et al, Nucl Acids Res, 18, 1062 (1990).
260. Wingender E et al. Nucleic Acids Res 29(1):281-3 (2001)
261. Wolter et al., EMBO Journal, 11:4685 (1992).
262. Wyn-Jones and Storey, Physiology and Biochemistry of Drought Resistance in Plants, Paleg et al. (eds.), pp. 171-204 (1981).
263. Yamaguchi-Shinozaki et al., Plant Cell Physiol., 33:217 (1992).
264. Zhang et al., Proc. Natl. Acad. Sci. USA, 94:4504 (1997).
265. Zukowsky et al., PNAS USA, 80:1101 (1983).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. An expression cassette for regulating vascular tissue-preferential or vascular tissue-specific expression in plants comprising
   i) at least one transcription regulating nucleotide sequence, and
   ii) at least one nucleic acid sequence which is operably linked to and heterologous in relation to said transcription regulating nucleotide sequence,
   wherein the transcription regulating nucleotide sequence comprises
   the nucleotide sequence described by SEQ ID NOs: 1, 2, 3, 4, or 5, or a fragment thereof having the same promoter activity as the nucleotide sequence of SEQ ID NO: 1, 2, 3, 4, or 5,
   wherein the transcription regulating nucleotide sequence directs vascular tissue-preferential or vascular tissue-specific transcription of the operably linked nucleic acid sequence in a plant cell.

2. The expression cassette of claim 1, wherein expression of the nucleic acid sequence results in expression of a protein, or expression of an antisense RNA, sense or double-stranded RNA.

3. The expression cassette of claim 1, wherein expression of the nucleic acid sequence confers to the plant an agronomically valuable trait.

4. A vector comprising the expression cassette of claim 1.

5. A transgenic host cell or non-human organism comprising the expression cassette of claim 1.

6. A transgenic host cell or non-human organism comprising the vector of claim 4.

7. A transgenic plant comprising the expression cassette of claim 1.

8. A transgenic plant comprising the vector of claim 4.

9. A transgenic plant comprising the cell of claim 5.

10. A method for identifying and/or isolating a sequence with vascular tissue-preferential or vascular tissue-specific transcription regulating activity comprising
    a) utilizing a nucleic acid sequence encoding the amino acid sequence as described by SEQ ID NO: 7 or a part thereof as a PCR primer or a probe;
    b) obtaining a gene sequence from a genomic or cDNA library or a database of an organism;
    c) isolating the associated transcription regulating sequence; and
    d) testing the isolated transcription regulating sequence for vascular tissue-preferential or vascular tissue-specific activity.

11. The method of claim 10, wherein the nucleic acid sequence is described by SEQ ID NO: 6 or a part thereof.

12. A method for providing a transgenic expression cassette for vascular tissue-preferential or vascular tissue-specific expression comprising the steps of:
    I. isolating the vascular tissue-preferential or vascular tissue-specific transcription regulating nucleotide sequence obtained by the method of claim 10, and
    II. functionally linking said vascular tissue-preferential or vascular tissue-specific transcription regulating nucleotide sequence to another nucleotide sequence of interest, which is heterologous in relation to said vascular tissue-preferential or vascular tissue-specific transcription regulating nucleotide sequence.

13. A method for producing a transgenic plant cell, comprising transforming a plant cell with the expression cassette of claim 1.

14. A method for producing a transgenic plant, comprising transforming a plant cell with the expression cassette of claim 1, and generating from the plant cell the transgenic plant.

* * * * *

SEQUENCE LISTING

<160> NUMBER OF SEQ ID NOS: 78

<210> SEQ ID NO 1
<211> LENGTH: 1043
<212> TYPE: DNA
<213> ORGANISM: Arabidopsis thaliana

```
<220> FEATURE:
<221> NAME/KEY: promoter
<222> LOCATION: (1)..(1043)
<223> OTHER INFORMATION: transcription regulating sequence from
      Arabidopsis thaliana gene At4g00140

<400> SEQUENCE: 1
gtccttgaaa atcagttaca tgtttctttt gttcttatct ttagtctttt gtgttttctc      60
ttttggcctt ttttcttcct ttatctattt acaagtcaag tcagcttatt aacaacgcgg     120
tatttccatc cccacaaaat cttcttatgg ctacttttat atatatatac atatcaaact     180
atactgacga caaaataaat aaattaagaa aaaaaagaa agagaaagtg ggtgtaggcc      240
atgcattatc ttaccaataa cacgtttcac accattcgca ttgcgctctc tccttccttc     300
atatgatcat atagaacgaa aggtggaaac tttcttattt tgtatggatc gtatacgcaa     360
tatggttgga caaactaat ctgtttcaaa caaatacat gaaatatccc acaagaaaca       420
aagcaaacta taaaaaaat aatgcggtaa acacggaaaa tatcacatat acgaatcctt      480
tttcggatgt gttttcaatc ctttgaatta aatatgtcca cactcgatat gtaaaaacaa     540
cttgacccat cacaattatg atcataaaat accaacgtac tgttagccta atgataaatc     600
tcccaagcag aggtgtttag ttcgagttat gttgtaaggg attttttctc ctaaggaaat     660
aaatttaatt tgatgtgaat tctaggaaat atagggcctc tcgacttaaa ctttcaaata    720
ttaaaaaaaa taaaaataat gatcatcatg agctattggg ttttcaatga tttatcagca    780
gagtgttcaa tgagagtcca agtatttggg ctgtaatatc aatatgggcc caaggtaaag    840
cccaacataa tcaatcggct attgggtatt ctaaattctc tcattataga agtgttcaat    900
gagggcccaa gtaattggtc ttaatatggg cccaagtaat tggtcttaat atgagcccaa    960
gttaaaccca acttaaacga ttgttggagg cggcaaaata aacaaatccc aaactctgga   1020
gaatcaaatt cctaattagc taa                                           1043

<210> SEQ ID NO 2
<211> LENGTH: 1057
<212> TYPE: DNA
<213> ORGANISM: Arabidopsis thaliana
<220> FEATURE:
<221> NAME/KEY: promoter
<222> LOCATION: (1)..(1057)
<223> OTHER INFORMATION: transcription regulating sequence from
      Arabidopsis thaliana gene At4g00140

<400> SEQUENCE: 2
gaccatactc atgtccttga aaatcagtta catgtttctt ttgttcttat ctttagtctt      60
ttgtgttttc tcttttggcc ttttttcttc ctttatctat ttacaagtca agtcagctta    120
ttaacaacgc ggtatttcca tccccacaaa atcttcttat ggctactttt atatatatat    180
acatatcaaa ctatactgac gacaaaataa ataaattaag aaaaaaaaag aaagagaaag    240
tgggtgtagg ccatgcatta tcttaccaat aacacgtttc acaccattcg cattgcgctc    300
tctccttcct tcatatgatc atatagaacg aaaggtggaa actttcttat tttgtatgga    360
tcgtatacgc aatatggttg gacaaaacta atctgtttca aacaaaatac atgaaatatc    420
ccacaagaaa caaagcaaac tataaaaaaa ataatgcggt aaacacggaa aatatcacat    480
atacgaatcc ttttcggat gtgttttcaa tcctttgaat taaatatgtc cacactcgat    540
atgtaaaaac aacttgaccc atcacaatta tgatcataaa ataccaacgt actgttagcc    600
taatgataaa tctcccaagc agaggtgttt agttcgagtt atgttgtaag gatttttc     660
```

```
tcctaaggaa ataaatttaa tttgatgtga attctaggaa atatagggcc tctcgactta    720
aactttcaaa tattaaaaaa aataaaaata atgatcatca tgagctattg ggttttcaat    780
gatttatcag cagagtgttc aatgagagtc caagtatttg ggctgtaata tcaatatggg    840
cccaaggtaa agcccaacat aatcaatcgg ctattgggta ttctaaattc tctcattata    900
gaagtgttca atgagggccc aagtaattgg tcttaatatg ggcccaagta attggtctta    960
atatgagccc aagttaaacc caacttaaac gattgttgga ggcggcaaaa taaacaaatc   1020
ccaaactctg gagaatcaaa ttcctaatta gctaaca                            1057
```

<210> SEQ ID NO 3
<211> LENGTH: 2464
<212> TYPE: DNA
<213> ORGANISM: Arabidopsis thaliana
<220> FEATURE:
<221> NAME/KEY: promoter
<222> LOCATION: (1)..(2464)
<223> OTHER INFORMATION: transcription regulating sequence from
      Arabidopsis thaliana gene At4g00140

<400> SEQUENCE: 3

```
cacacatcga agcatactct tgataatata tggacaggga aatacatatt agaaagctat     60
caaactttct cttcctttt tttttgtttg ctgggtttca tctttcacta tattgtatgt    120
gtgacatgtc attaagaaat gaataacaac aggctattca ttgctttttt ctattcattg    180
cttacaaaaa gtaaaatgat gataaaatac gcagcttttg gtgttatttg tccttcaact    240
aattgagtta tcatttttct tttactcctt ttagacaccg catatgtact tttgtctcaa    300
agaagactct cctaggagtt aggaagattt tgattttgtt ataatcagac tttaactcac    360
atctgtcttc catcatccca ctgttttca agtatttat tattagttgt taaaaacttc     420
tacgtccaaa atctcaatca ctacgagtat tgcaatgttg atattgtgcg ttaaatgtat    480
atgtatataa ttccaaattt ccaacaattg gtttataaac gatggcacta acataacctc    540
atatattgtg atacaacgaa aggcaccgga tggtggaacg catcacgcat catgcatcct    600
cgatcccttt tcaagtggt atgtaagaga tcattatttc aacataacat acatttgcta    660
tgatgacgca ttttagtcaa attagttgtt tgttcaatca tattaataag ggtcaacaga    720
tatttatacg aactgtaatt aaaatgataa aatccaaagc gacaagtttg ctactaccaa    780
atgtgtgttt aatatatata atttagaaac attgaatttg agaaaatgag tatacggttg    840
cacaaaagaa gaagaagaag aggagtatac caacaaaagg ttgtacgtaa tataattccg    900
accccctaaa aagatatata ataaggtgga gagcgaggga tctgaaattg atgggtgtgt    960
ttttgtgtgc ataacaaaag ttaaaaatgt atttatatta ttttttaattt taaaattctt   1020 ttcttacttg tgtttatta ttagttaaat aaataattta atgagagaag cttttgatac    1080 aattttact ctctttcaat ctccatctca acttttgtag atgccaagct tgcccaccat    1140
atctgctcct caacctctca ctttacaagt acttcattta tttcttagt tagtctattt    1200 atttcaataa acaaactcta ctcaagttca tcaagattcg taacagtgga atcctttatt   1260
aatgttagat catcaaactc tacacatgtt tattccatc tctatgcatg cctttatatt    1320
gcttaagttg tatacacgta catatacact tcactactct tattatctag ttccatatta   1380
cgctatatat ttatgaattt atatacatag accatactca tgtccttgaa aatcagttac    1440
atgtttcttt tgttcttatc tttagtcttt tgtgttttct cttttggcct ttttcttcc    1500 tttatctatt tacaagtcaa gtcagcttat taacaacgcg gtatttccat ccccacaaaa    1560
```

-continued

```
tcttcttatg gctactttta tatatatata catatcaaac tatactgacg acaaaataaa      1620
taaattaaga aaaaaaaga aagagaaagt gggtgtaggc catgcattat cttaccaata      1680
acacgtttca caccattcgc attgcgctct ctccttcctt catatgatca tatagaacga      1740
aaggtggaaa ctttcttatt ttgtatggat cgtatacgca atatggttgg acaaaactaa      1800
tctgtttcaa acaaaataca tgaaatatcc cacaagaaac aaagcaaact ataaaaaaaa      1860
taatgcggta aacacggaaa atatcacata tacgaatcct ttttcggatg tgttttcaat      1920
cctttgaatt aaatatgtcc acactcgata tgtaaaaaca acttgaccca tcacaattat      1980
gatcataaaa taccaacgta ctgttagcct aatgataaat ctcccaagca gaggtgttta      2040
gttcgagtta tgttgtaagg gattttttct cctaaggaaa taaatttaat ttgatgtgaa      2100
ttctaggaaa tatagggcct ctcgacttaa actttcaaat attaaaaaaa ataaaaataa      2160
tgatcatcat gagctattgg gttttcaatg atttatcagc agagtgttca atgagagtcc      2220
aagtatttgg gctgtaatat caatatgggc ccaaggtaaa gcccaacata atcaatcggc      2280
tattgggtat tctaaattct ctcattatag aagtgttcaa tgagggccca agtaattggt      2340
cttaatatgg gcccaagtaa ttggtcttaa tatgagccca agttaaaccc aacttaaacg      2400
attgttggag gcggcaaaat aaacaaatcc caaactctgg agaatcaaat tcctaattag      2460
ctaa                                                                  2464
```

<210> SEQ ID NO 4
<211> LENGTH: 2478
<212> TYPE: DNA
<213> ORGANISM: Arabidopsis thaliana
<220> FEATURE:
<221> NAME/KEY: promoter
<222> LOCATION: (1)..(2478)
<223> OTHER INFORMATION: transcription regulating sequence from
      Arabidopsis thaliana gene At4g00140

<400> SEQUENCE: 4

```
gacgggactg atcacacatc gaagcatact cttgataata tatggacagg gaaatacata       60
ttagaaagct atcaaacttt ctcttccttt ttttttttgtt tgctgggttt catctttcac      120
tatattgtat gtgtgacatg tcattaagaa atgaataaca acaggctatt cattgctttt      180
ttctattcat tgcttacaaa aagtaaaatg atgataaaat acgcagcttt tggtgttatt      240
tgtccttcaa ctaattgagt tatcatttt ctttactcc ttttagacac cgcatatgta        300
cttttgtctc aaagaagact ctcctaggag ttaggaagat tttgattttg ttataatcag      360
actttaactc acatctgtct tccatcatcc cactgttttt caagtatttt attattagtt      420
gttaaaaact tctacgtcca aaatctcaat cactacgagt attgcaatgt tgatattgtg      480
cgttaaatgt atatgtatat aattccaaat ttccaacaat tggtttataa acgatggcac      540
taacataacc tcatatattg tgatacaacg aaaggcaccg gatggtggaa cgcatcacgc      600
atcatgcatc ctcgatccct tttcaaagtg gtatgtaaga gatcattatt tcaacataac      660
atacatttgc tatgatgacg catttttagtc aaattagttg tttgttcaat catattaata      720
agggtcaaca gatattttata cgaactgtaa ttaaaatgat aaaatccaaa gcgacaagtt      780
tgctactacc aaatgtgtgt ttaatatata taatttagaa acattgaatt tgagaaaatg      840
agtatacggt tgcacaaaag aagaagaaga agaggagtat accaacaaaa ggttgtacgt      900
aatataattc cgacccccta aaaagatata taataaggtg gagagcgagg gatctgaaat      960
tgatgggtgt gttttttgtgt gcataacaaa agttaaaaat gtatttatat tatttttaat      1020
```

```
tttaaaattc ttttcttact tgtgtttatt tattagttaa ataaataatt taatgagaga    1080
agcttttgat acaatttta ctctctttca atctccatct caacttttgt agatgccaag    1140
cttgcccacc atatctgctc ctcaacctct cactttacaa gtacttcatt tattttctta    1200
gttagtctat ttatttcaat aaacaaactc tactcaagtt catcaagatt cgtaacagtg    1260
gaatccttta ttaatgttag atcatcaaac tctacacatg tttatttcca tctctatgca    1320
tgcctttata ttgcttaagt tgtatacacg tacatataca cttcactact cttattatct    1380
agttccatat tacgctatat atttatgaat ttatatacat agaccatact catgtccttg    1440
aaaatcagtt acatgtttct tttgttctta tctttagtct tttgtgtttt ctcttttggc    1500 ctttttttctt cctttatcta tttacaagtc aagtcagctt attaacaacg cggtatttcc    1560
atccccacaa aatcttctta tggctacttt tatatatata tacatatcaa actatactga    1620
cgacaaaata aataaattaa gaaaaaaaaa gaaagagaaa gtgggtgtag gccatgcatt    1680
atcttaccaa taacacgttt cacaccattc gcattgcgct ctctccttcc ttcatatgat    1740
catatagaac gaaaggtgga aactttctta ttttgtatgg atcgtatacg caatatggtt    1800
ggacaaaact aatctgtttc aaacaaaata catgaaatat cccacaagaa acaaagcaaa    1860
ctataaaaaa aataatgcgg taaacacgga aaatatcaca tatcgaatc cttttcgga    1920 tgtgttttca atcctttgaa ttaaatatgt ccacactcga tatgtaaaaa caacttgacc    1980
catcacaatt atgatcataa aataccaacg tactgttagc ctaatgataa atctcccaag    2040
cagaggtgtt tagttcgagt tatgttgtaa gggattttt ctcctaagga aataaattta    2100
atttgatgtg aattctagga aatatagggc ctctcgactt aaactttcaa atattaaaaa    2160
aaataaaaat aatgatcatc atgagctatt gggttttcaa tgatttatca gcagagtgtt    2220
caatgagagt ccaagtattt gggctgtaat atcaatatgg gcccaaggta agcccaaca    2280 taatcaatcg ctattgggt attctaaatt ctctcattat agaagtgttc aatgagggcc    2340
caagtaattg gtcttaatat gggcccaagt aattggtctt aatatgagcc caagttaaac    2400
ccaacttaaa cgattgttgg aggcggcaaa ataaacaaat cccaaactct ggagaatcaa    2460
attcctaatt agctaaca                                                  2478
```

<210> SEQ ID NO 5
<211> LENGTH: 3977
<212> TYPE: DNA
<213> ORGANISM: Arabidopsis thaliana
<220> FEATURE:
<221> NAME/KEY: promoter
<222> LOCATION: (1)..(3977)
<223> OTHER INFORMATION: transcription regulating sequence from
      Arabidopsis thaliana gene At4g00140

<400> SEQUENCE: 5

```
tccaccggag tttcaattat taaaaaaata ttttccttaa ttcaatttat cttaaatgac      60 aaattttag tttctgattt tattttgctc agtgcgatgg attttaaat ttaagtttca      120 cacaaatata taaattttg tgagaagtta attaattgtc tgattatcaa acacttattg     180
tataacacat tcaatatata ttaattgtgg ggattatttt tgatcgacta aataacgtga     240
tagaataatg cttggattag ctcaatacta tatttttcta attaaaaatg aatggggtgt     300
tgattttgat gcgaggcaga aagctactgc tcattattgt gattatatga ttatataatg     360
gttagagttt gttgtggttt gtgtctttgc gaggggtcta ttttttaattt ataaacatat    420 gtctccatga tgtcacatgg gtcttgtatt attttattta tttggaccac aatacatttt    480
```

```
tgtgtgcgcc gtttctaacc ttttttttc tccgacgaaa caaaggtttg cttttctcc      540 tttaaatggt ccatacgcat tacatatata atgcgcccat ttgctttacg cattaactgc    600
atttctctat agaaatattt cagaaacaaa ccaagtgtat acaatacatc aacatgtttt    660
ttttggggtt ttaatgtgaa gatttcattt caataaaaag attacaagct aatctaagta    720
atacaaacca acatattttg gtttactctt tatattaaaa catcatttag gataattatt    780
taaaatatat attcaaacat ctaaggtcct aattaagcat tacaaaagat ttccgttta     840 gaaacatatc aagagttgat taaatggaga aagacgacta aaatttgtga gtgaaaaatg    900
acaatatgcc gcaagttatt gtctcttgtg caataaacgt tggttggata cagacacatt    960
tgattgaatg tgaatagttt agttttgaca gatcataagc cgtgtcctca agcagaagac    1020
cggtcgtgat cggtcaatct acacgtgtac ggcagaaaca catgtgtcgt ttccctgtga    1080
gagatgatca accaaatcaa cggtcagttt ttgtcaacta atgtgtgtat tgatttgtaa    1140
catgcctacg tgaacataag ctagtcacgc aacaagcaag gcctgggtca cgcaggctcg    1200
gctccactaa gacgcgccga cgtagtcact catcatatat cacatgtcta gattcaaatg    1260
gtaaccgttt tgatgagcgca gtaagtagaa acattgaccg gtccaggcga ggtctagcaa    1320
atactattag aattaaaatt gatgtaatca atcactgata aatactatta gaactactct    1380 acttacact cacgtattcc atcatttaat atacatacgt gagtgtaaag tatttcttca     1440
caatttattt ttgaaaatag cttttaaccc atagcaaatg cctatgttgc catggggtag    1500
acgggactga tcacacatcg aagcatactc ttgataatat atggacaggg aaatacatat    1560
tagaaagcta tcaaactttc tcttccttt tttttgttt gctgggtttc atctttcact      1620
atattgtatg tgtgacatgt cattaagaaa tgaataacaa caggctattc attgcttttt    1680
tctattcatt gcttacaaaa agtaaaatga tgataaaata cgcagcttt ggtgttattt      1740 gtccttcaac taattgagtt atcatttttc ttttactcct tttagacacc gcatatgtac    1800
ttttgtctca aagaagactc tcctaggagt taggaagatt ttgattttgt tataatcaga    1860
ctttaactca catctgtctt ccatcatccc actgttttc aagtatttta ttattagttg      1920
ttaaaaactt ctacgtccaa aatctcaatc actacgagta ttgcaatgtt gatattgtgc    1980
gttaaatgta tatgtatata attccaaatt tccaacaatt ggtttataaa cgatggcact    2040
aacataaact catatattgt gatacaacga aaggcaccgg atggtggaac gcatcacgca    2100
tcatgcatcc tcgatccctt ttcaaagtgg tatgtaagag atcattattt caacataaca    2160
tacatttgct atgatgacgc attttagtca aattagttgt ttgttcaatc atattaataa    2220
gggtcaacag atatttatac gaactgtaat taaaatgata aaatccaaag cgacaagttt    2280
gctactacca aatgtgtgtt taatatatat aatttagaaa cattgaattt gagaaaatga    2340
gtatacggtt gcacaaaaga agaagaagaa gaggagtata ccaacaaaag gttgtacgta    2400
atataattcc gacccctaa aaagatatat aataaggtgg agagcgaggg atctgaaatt      2460
gatgggtgtg tttttgtgtg cataacaaaa gttaaaaatg tatttatatt attttttaatt    2520 ttaaaattct tttcttactt gtgtttattt attagttaaa taaataattt aatgagagaa    2580
gcttttgata caattttac tctctttcaa tctccatctc aacttttgta gatgccaagc      2640
ttgcccacca tatctgctcc tcaacctctc actttacaag tacttcattt attttcttag    2700
ttagtctatt tatttcaata aacaaactct actcaagttc atcaagattc gtaacagtgg    2760
aatcctttat taatgttaga tcatcaaact ctacacatgt ttatttccat ctctatgcat    2820
gcctttatat tgcttaagtt gtatacacgt acatatacac ttcactactc ttattatcta    2880
```

-continued

```
gttccatatt acgctatata tttatgaatt tatatacata gaccatactc atgtccttga      2940
aaatcagtta catgtttctt tgttcttat ctttagtctt ttgtgttttc tcttttggcc       3000
ttttttcttc ctttatctat ttacaagtca agtcagctta ttaacaacgc ggtatttcca      3060
tccccacaaa atcttcttat ggctactttt atatatatat acatatcaaa ctatactgac      3120
gacaaaataa ataaattaag aaaaaaaaag aaagagaaag tgggtgtagg ccatgcatta      3180
tcttaccaat aacacgtttc acaccattcg cattgcgctc tctccttcct tcatatgatc      3240
atatagaacg aaaggtggaa actttcttat tttgtatgga tcgtatacgc aatatggttg      3300
gacaaaacta atctgtttca aacaaatac atgaaatatc ccacaagaaa caaagcaaac       3360
tataaaaaaa ataatgcggt aaacacggaa aatatcacat atacgaatcc tttttcggat      3420
gtgttttcaa tcctttgaat taaatatgtc cacactcgat atgtaaaaac aacttgaccc      3480
atcacaatta tgatcataaa ataccaacgt actgttagcc taatgataaa tctcccaagc      3540
agaggtgttt agttcgagtt atgttgtaag ggattttttc tcctaaggaa ataaatttaa      3600
tttgatgtga attctaggaa atatagggcc tctcgactta aactttcaaa tattaaaaaa      3660
aataaaaata atgatcatca tgagctattg ggttttcaat gatttatcag cagagtgttc      3720
aatgagagtc caagtatttg ggctgtaata tcaatatggg cccaaggtaa agcccaacat      3780
aatcaatcgg ctattgggta ttctaaattc tctcattata gaagtgttca atgagggccc      3840
aagtaattgg tcttaatatg ggcccaagta attggtctta tatgagccc aagttaaacc       3900 caacttaaac gattgttgga ggcggcaaaa taaacaaatc ccaaactctg gagaatcaaa      3960
ttcctaatta gctaaca                                                    3977
```

<210> SEQ ID NO 6
<211> LENGTH: 774
<212> TYPE: DNA
<213> ORGANISM: Arabidopsis thaliana
<220> FEATURE:
<221> NAME/KEY: CDS
<222> LOCATION: (1)..(774)

<400> SEQUENCE: 6

```
atg gcg agg gga gaa tcg gag gga gag agc tca gga agt gaa cga gag        48
Met Ala Arg Gly Glu Ser Glu Gly Glu Ser Ser Gly Ser Glu Arg Glu
1               5                   10                  15 agt tcg agc tcg agt tcc ggc aac gaa tcg gag ccg ata aag ggg aaa        96
Ser Ser Ser Ser Ser Ser Gly Asn Glu Ser Glu Pro Ile Lys Gly Lys
                20                  25                  30 atc tcg gaa tat gag aag cag agg ttg tca agg atc gct gag aac aaa       144
Ile Ser Glu Tyr Glu Lys Gln Arg Leu Ser Arg Ile Ala Glu Asn Lys
            35                  40                  45 gcg aga ttg gat gca ctc gga att ccg gca ata gcg ctt tct cta cag       192
Ala Arg Leu Asp Ala Leu Gly Ile Pro Ala Ile Ala Leu Ser Leu Gln
        50                  55                  60 ggc tct gtt gca gga ggc tct cgt acg aaa aat acg aga agc gat aaa       240
Gly Ser Val Ala Gly Gly Ser Arg Thr Lys Asn Thr Arg Ser Asp Lys
65                  70                  75                  80 gag gct gca act atg aag aag aaa aga cag gaa ggt gga aaa ggg ttc       288
Glu Ala Ala Thr Met Lys Lys Lys Arg Gln Glu Gly Gly Lys Gly Phe
                85                  90                  95 att act cgg aga gat gtg gcg aaa atg gca acg gtg cat gac ttc aca       336
Ile Thr Arg Arg Asp Val Ala Lys Met Ala Thr Val His Asp Phe Thr
            100                 105                 110
```

```
tgg aca gaa gag gaa tta caa gac atg att cgt tcc ttt gac atg gac    384
Trp Thr Glu Glu Glu Leu Gln Asp Met Ile Arg Ser Phe Asp Met Asp
        115                 120                 125 aag gac gga aag gtg ggt act aag ttg aag gta ttc acg ttt att aga    432
Lys Asp Gly Lys Val Gly Thr Lys Leu Lys Val Phe Thr Phe Ile Arg
    130                 135                 140 gaa aca tta ttg cta aac atc ttt aat ttt ggg cag cta agc tgc cga    480
Glu Thr Leu Leu Leu Asn Ile Phe Asn Phe Gly Gln Leu Ser Cys Arg
145                 150                 155                 160 tcg tct gac gga acg ggt cgg aca gac cga tcg tcg gat ggg atg gat    528
Ser Ser Asp Gly Thr Gly Arg Thr Asp Arg Ser Ser Asp Gly Met Asp
                165                 170                 175 cga gaa aag tgt tcg agg aag cac aag gat aag tgc atc cga aca cac    576
Arg Glu Lys Cys Ser Arg Lys His Lys Asp Lys Cys Ile Arg Thr His
            180                 185                 190 cca agg gtc gcc cat gga tgc aat ctt acc ggt aaa ggg aga aag cac    624
Pro Arg Val Ala His Gly Cys Asn Leu Thr Gly Lys Gly Arg Lys His
        195                 200                 205 caa gaa tgg gta agg aac gtg att cac cat ata gga tca aca tcg cgg    672
Gln Glu Trp Val Arg Asn Val Ile His His Ile Gly Ser Thr Ser Arg
    210                 215                 220 ccg cct tca tgt atc tat ctc ctc agc cat ggt gaa acc gat caa aga    720
Pro Pro Ser Cys Ile Tyr Leu Leu Ser His Gly Glu Thr Asp Gln Arg
225                 230                 235                 240 tcg gta aga cca aag ggt gac tcg atg gat aac caa cgg gaa agt cca    768
Ser Val Arg Pro Lys Gly Asp Ser Met Asp Asn Gln Arg Glu Ser Pro
                245                 250                 255 cgg tga                                                            774
Arg

<210> SEQ ID NO 7
<211> LENGTH: 257
<212> TYPE: PRT
<213> ORGANISM: Arabidopsis thaliana

<400> SEQUENCE: 7

Met Ala Arg Gly Glu Ser Glu Gly Glu Ser Ser Gly Ser Glu Arg Glu
1               5                   10                  15

Ser Ser Ser Ser Ser Gly Asn Glu Ser Glu Pro Ile Lys Gly Lys
            20                  25                  30

Ile Ser Glu Tyr Glu Lys Gln Arg Leu Ser Arg Ile Ala Glu Asn Lys
        35                  40                  45

Ala Arg Leu Asp Ala Leu Gly Ile Pro Ala Ile Ala Leu Ser Leu Gln
    50                  55                  60

Gly Ser Val Ala Gly Gly Ser Arg Thr Lys Asn Thr Arg Ser Asp Lys
65                  70                  75                  80

Glu Ala Ala Thr Met Lys Lys Lys Arg Gln Glu Gly Gly Lys Gly Phe
                85                  90                  95

Ile Thr Arg Arg Asp Val Ala Lys Met Ala Thr Val His Asp Phe Thr
            100                 105                 110

Trp Thr Glu Glu Glu Leu Gln Asp Met Ile Arg Ser Phe Asp Met Asp
        115                 120                 125

Lys Asp Gly Lys Val Gly Thr Lys Leu Lys Val Phe Thr Phe Ile Arg
    130                 135                 140

Glu Thr Leu Leu Leu Asn Ile Phe Asn Phe Gly Gln Leu Ser Cys Arg
145                 150                 155                 160

Ser Ser Asp Gly Thr Gly Arg Thr Asp Arg Ser Ser Asp Gly Met Asp
                165                 170                 175
```

Arg Glu Lys Cys Ser Arg Lys His Lys Asp Lys Cys Ile Arg Thr His
            180                 185                 190

Pro Arg Val Ala His Gly Cys Asn Leu Thr Gly Lys Gly Arg Lys His
        195                 200                 205

Gln Glu Trp Val Arg Asn Val Ile His His Ile Gly Ser Thr Ser Arg
    210                 215                 220

Pro Pro Ser Cys Ile Tyr Leu Leu Ser His Gly Glu Thr Asp Gln Arg
225                 230                 235                 240

Ser Val Arg Pro Lys Gly Asp Ser Met Asp Asn Gln Arg Glu Ser Pro
                245                 250                 255

Arg

<210> SEQ ID NO 8
<211> LENGTH: 1147
<212> TYPE: DNA
<213> ORGANISM: Arabidopsis thaliana
<220> FEATURE:
<221> NAME/KEY: promoter
<222> LOCATION: (1)..(1147)
<223> OTHER INFORMATION: transcription regulating sequence from
      Arabidopsis thaliana gene At5g45350

<400> SEQUENCE: 8

| | | | | | |
|---|---|---|---|---|---|
| tctcctttgc | ccccacagtt | taatatattt | cataaacacc | cccacgagaa | attaaaaacc | 60 |
| gttccaaatt | tgaaaaaata | caacaaacaa | ttcatgaaaa | tattcaatct | ataagcaaaa | 120 |
| cattggtagt | gttacatgtg | tcgtccttcg | tgctgaaaat | ttggatagca | ttgttaatta | 180 |
| tgacaacgta | agtgtagcct | gtgattcata | gtaaaatata | aggactaaaa | ataaaaatat | 240 |
| atcttttttg | gaaatcgtac | cgcgtaagaa | acatgtataa | atacctataa | ggtcttattt | 300 |
| ttttctcttc | caatttcgtt | tcgacatatt | tcgcgattcg | tctaaggtaa | aaaaaaactc | 360 |
| atctttttt | cttttagatc | gttaattttt | gatcagcgat | tcgctcttct | gatctgtgtt | 420 |
| ctttaagctt | gtcttctctc | ttgattcgat | ctgctgaaaa | cctagaaatt | tttgattttt | 480 |
| ttgtttgttt | tgctccatgt | gtatgggtat | atttacgatt | ttaacaaaac | aaaaatatga | 540 |
| attgaggttt | tttatttagc | gaattggggtt | ttaattgttc | acattcgttt | ggctctctcg | 600 |
| aggtgagtga | taaagtatag | aactttctta | tgcttaggat | cttaaattcg | agttctttga | 660 |
| tttacctgtc | atgtgttatt | gattgatctc | atttatattg | tgtctgcttg | atgtttaaag | 720 |
| cttggtgtat | gcaatttgat | tgggtttact | ggagattgat | ctgtgaccta | atcaatgagt | 780 |
| gataacattg | ctggttcatc | tgatttctca | tctggtgtgt | ctgctcgatt | ccctgaagaa | 840 |
| agtttgaaac | tcaggcttgg | tttgtgcagt | ttgattgatt | tatctcatta | cttgactctg | 900 |
| gtgtacttga | ttctttgatg | aaagcttgaa | gttaatgttt | ggtttgtgca | atatgattgg | 960 |
| gattaactgc | atttgatctc | tgaccaaaat | cagtgattaa | ttacattgct | tggttatctc | 1020 |
| attacttgag | tttggtgttc | ctgcatgatc | ccctgagctt | gaagttcatg | cttggtttgt | 1080 |
| ccaattgtga | cctaaattga | tgttttcttg | tggtatcttt | tcgtaggttt | tgttactgat | 1140 |
| tgagaaa | | | | | | 1147 |

<210> SEQ ID NO 9
<211> LENGTH: 1161
<212> TYPE: DNA
<213> ORGANISM: Arabidopsis thaliana
<220> FEATURE:
<221> NAME/KEY: promoter
<222> LOCATION: (1)..(1161)
<223> OTHER INFORMATION: transcription regulating sequence from
      Arabidopsis thaliana gene At5g45350

<400> SEQUENCE: 9

| | | | | | |
|---|---|---|---|---|---|
| ttctcataat | tctctccttt | gcccccacag | tttaatatat | ttcataaaca | ccccacgag | 60 |
| aaattaaaaa | ccgttccaaa | tttgaaaaaa | tacaacaaac | aattcatgaa | aatattcaat | 120 |
| ctataagcaa | acattggta | gtgttacatg | tgtcgtcctt | cgtgctgaaa | atttggatag | 180 |
| cattgttaat | tatgacaacg | taagtgtagc | ctgtgattca | tagtaaaata | taaggactaa | 240 |
| aaataaaaat | atatcttttt | tggaaatcgt | accgcgtaag | aaacatgtat | aaataccta | 300 |
| aaggtcttat | ttttttctct | tccaatttcg | tttcgacata | tttcgcgatt | cgtctaaggt | 360 |
| aaaaaaaaac | tcatcttttt | ttcttttaga | tcgttaattt | ttgatcagcg | attcgctctt | 420 |
| ctgatctgtg | ttctttaagc | ttgtcttctc | tcttgattcg | atctgctgaa | acctagaaa | 480 |
| tttttgattt | ttttgtttgt | tttgctccat | gtgtatgggt | atatttacga | ttttaacaaa | 540 |
| acaaaaatat | gaattgaggt | ttttattta | gcgaattggg | ttttaattgt | tcacattcgt | 600 |
| ttggctctct | cgaggtgagt | gataaagtat | agaactttct | tatgcttagg | atcttaaatt | 660 |
| cgagttcttt | gatttacctg | tcatgtgtta | ttgattgatc | tcatttatat | tgtgtctgct | 720 |
| tgatgtttaa | agcttggtgt | atgcaatttg | attgggttta | ctggagattg | atctgtgacc | 780 |
| taatcaatga | gtgataacat | tgctggttca | tctgatttct | catctggtgt | gtctgctcga | 840 |
| ttccctgaag | aaagtttgaa | actcaggctt | ggtttgtgca | gtttgattga | tttatctcat | 900 |
| tacttgactc | tggtgtactt | gattctttga | tgaaagcttg | aagttaatgt | ttggtttgtg | 960 |
| caatatgatt | gggattaact | gcatttgatc | tctgaccaaa | atcagtgatt | aattacattg | 1020 |
| cttggttatc | tcattacttg | agtttggtgt | tcctgcatga | tccctgagc | ttgaagttca | 1080 |
| tgcttggttt | gtccaattgt | gacctaaatt | gatgttttct | tgtggtatct | tttcgtaggt | 1140 |
| tttgttactg | attgagaaaa | c | | | | 1161 |

<210> SEQ ID NO 10
<211> LENGTH: 304
<212> TYPE: DNA
<213> ORGANISM: Arabidopsis thaliana
<220> FEATURE:
<221> NAME/KEY: promoter
<222> LOCATION: (1)..(304)
<223> OTHER INFORMATION: transcription regulating sequence from
      Arabidopsis thaliana gene At5g45350

<400> SEQUENCE: 10

| | | | | | |
|---|---|---|---|---|---|
| tctcctttgc | ccccacagtt | taatatattt | cataaacacc | cccacgagaa | attaaaaacc | 60 |
| gttccaaatt | tgaaaaaata | caacaaacaa | ttcatgaaaa | tattcaatct | ataagcaaaa | 120 |
| cattggtagt | gttacatgtg | tcgtccttcg | tgctgaaaat | ttggatagca | ttgttaatta | 180 |
| tgacaacgta | agtgtagcct | gtgattcata | gtaaaatata | aggactaaaa | ataaaaatat | 240 |
| atcttttttg | gaaatcgtac | cgcgtaagaa | acatgtataa | atacctataa | ggtcttattt | 300 |
| tttt | | | | | | 304 |

<210> SEQ ID NO 11
<211> LENGTH: 316
<212> TYPE: DNA
<213> ORGANISM: Arabidopsis thaliana
<220> FEATURE:
<221> NAME/KEY: promoter
<222> LOCATION: (1)..(316)
<223> OTHER INFORMATION: transcription regulating sequence from
      Arabidopsis thaliana gene At5g45350

<400> SEQUENCE: 11

| | | | | | |
|---|---|---|---|---|---|
| ttctcataat | tctctccttt | gcccccacag | tttaatatat | ttcataaaca | cccccacgag | 60 |
| aaattaaaaa | ccgttccaaa | tttgaaaaaa | tacaacaaac | aattcatgaa | aatattcaat | 120 |
| ctataagcaa | aacattggta | gtgttacatg | tgtcgtcctt | cgtgctgaaa | atttggatag | 180 |
| cattgttaat | tatgacaacg | taagtgtagc | ctgtgattca | tagtaaaata | taaggactaa | 240 |
| aaataaaaat | atatctttt | tggaaatcgt | accgcgtaag | aaacatgtat | aaatacctat | 300 |
| aaggtcttat | tttttt | | | | | 316 |

<210> SEQ ID NO 12
<211> LENGTH: 1931
<212> TYPE: DNA
<213> ORGANISM: Arabidopsis thaliana
<220> FEATURE:
<221> NAME/KEY: promoter
<222> LOCATION: (1)..(1931)
<223> OTHER INFORMATION: transcription regulating sequence from
      Arabidopsis thaliana gene At5g45350

<400> SEQUENCE: 12

| | | | | | |
|---|---|---|---|---|---|
| gctgagcaaa | agtctcgacc | ttttgtccaa | tttcataagg | cctactttct | gtaaggtctt | 60 |
| ctctctctct | ctctctctga | cctgattctg | cctgggttct | gtggagttga | aatgaatcaa | 120 |
| atgtagctct | tgttttaatc | agtcagcttt | gtaacgtata | catatatatc | attgtatgtg | 180 |
| attaacattg | tccttaaaaa | gtgttacacc | tagtaattac | gttccaactt | tatcagtaaa | 240 |
| cctattggta | actagtaatt | tgctcccgat | attggttttc | tcattaattt | ttatagccat | 300 |
| tctttgttca | tttaaaccat | attacaaatt | tgtcctggtt | agaactgatt | atgatgacaa | 360 |
| atcgatgatt | agttcaaaat | gaagtttata | gcaatatatt | ctaataacta | tacatcaatt | 420 |
| atcaccactg | atgtgtttga | atgaaaaatg | aattgataat | cttaataaat | gtttgattt | 480 |
| atagataagt | ataaagtatg | aatggattta | gaaaatttta | gtatttagtg | agataagcat | 540 |
| aagcaaaact | agaaaatgaa | aattattatt | aaataaattc | attaatacac | attggcaatg | 600 |
| tgacattgcc | taaaatcaaa | tatgtactaa | ttcaattaat | gttaataaga | attttttgga | 660 |
| ttcgattctc | ttgcgaaagt | gcaaattaaa | agacattct | atctcctacg | taaacagaat | 720 |
| cacgcgtcca | ttgcgcgttc | tcgcaacgct | aaaatattta | cgttggaaaa | tattctcata | 780 |
| attctctcct | tgcccccac | agtttaatat | atttcataaa | cacccccacg | agaaattaaa | 840 |
| aaccgttcca | aatttgaaaa | aatacaacaa | acaattcatg | aaaatattca | atctataagc | 900 |
| aaaacattgg | tagtgttaca | tgtgtcgtcc | ttcgtgctga | aaatttggat | agcattgtta | 960 |
| attatgacaa | cgtaagtgta | gcctgtgatt | catagtaaaa | tataaggact | aaaaataaaa | 1020 |
| atatatcttt | tttggaaatc | gtaccgcgta | agaaacatgt | ataaatacct | ataaggtctt | 1080 |
| attttttct | cttccaattt | cgtttcgaca | tatttcgcga | ttcgtctaag | gtaaaaaaaa | 1140 |
| actcatcttt | ttttctttta | gatcgttaat | ttttgatcag | cgattcgctc | ttctgatctg | 1200 |
| tgttcttta | gcttgtcttc | tctcttgatt | cgatctgctg | aaaacctaga | aattttgat | 1260 |
| tttttgttt | gttttgctcc | atgtgtatgg | gtatatttac | gatttaaca | aaacaaaaat | 1320 |
| atgaattgag | gttttttatt | tagcgaattg | ggttttaatt | gttcacattc | gtttggctct | 1380 |

```
ctcgaggtga gtgataaagt atagaacttt cttatgctta ggatcttaaa ttcgagttct    1440
ttgatttacc tgtcatgtgt tattgattga tctcatttat attgtgtctg cttgatgttt    1500
aaagcttggt gtatgcaatt tgattgggtt tactggagat tgatctgtga cctaatcaat    1560
gagtgataac attgctggtt catctgattt ctcatctggt gtgtctgctc gattccctga    1620
agaaagtttg aaactcaggc ttggtttgtg cagtttgatt gatttatctc attacttgac    1680
tctggtgtac ttgattcttt gatgaaagct tgaagttaat gtttggtttg tgcaatatga    1740
ttgggattaa ctgcatttga tctctgacca aaatcagtga ttaattacat tgcttggtta    1800
tctcattact tgagtttggt gttcctgcat gatcccctga gcttgaagtt catgcttggt    1860
ttgtccaatt gtgacctaaa ttgatgtttt cttgtggtat cttttcgtag gttttgttac    1920
tgattgagaa a                                                         1931

<210> SEQ ID NO 13
<211> LENGTH: 1945
<212> TYPE: DNA
<213> ORGANISM: Arabidopsis thaliana
<220> FEATURE:
<221> NAME/KEY: promoter
<222> LOCATION: (1)..(1945)
<223> OTHER INFORMATION: transcription regulating sequence from
      Arabidopsis thaliana gene At5g45350

<400> SEQUENCE: 13
ccctgaggtt ctgctgagca aaagtctcga ccttttgtcc aatttcataa ggcctacttt     60
ctgtaaggtc ttctctctct ctctctctct gacctgattc tgcctgggtt ctgtggagtt    120
gaaatgaatc aaatgtagct cttgttttaa tcagtcagct ttgtaacgta tacatatata    180
tcattgtatg tgattaacat tgtccttaaa aagtgttaca cctagtaatt acgttccaac    240
tttatcagta aacctattgg taactagtaa tttgctcccg atattggttt tctcattaat    300
ttttatagcc attctttgtt catttaaacc atattacaaa tttgtcctgg ttagaactga    360
ttatgatgac aaatcgatga ttagttcaaa atgaagttta tagcaatata ttctaataac    420
tatacatcaa ttatcaccac tgatgtgttt gaatgaaaaa tgaattgata atcttaataa    480
atgtttgatt ttatagataa gtataaagta tgaatggatt tagaaaattt tagtatttag    540
tgagataagc ataagcaaaa ctagaaaaat gaaattatta ttaaataaat tcattaatac    600
acattggcaa tgtgacattg cctaaaatca aatatgtact aattcaatta atgttaataa    660 gaatttttg gattcgattc tcttgcgaaa gtgcaaatta aaagacattc ttatctccta    720
cgtaaacaga atcacgcgtc cattgcgcgt tctcgcaacg ctaaaatatt tacgttggaa    780
aatattctca taattctctc ctttgccccc acagtttaat atatttcata aacaccccca    840
cgagaaatta aaaaccgttc caaatttgaa aaaatacaac aaacaattca tgaaaatatt    900
caatctataa gcaaaacatt ggtagtgtta catgtgtcgt ccttcgtgct gaaaatttgg    960
atagcattgt taattatgac aacgtaagtg tagcctgtga ttcatagtaa aatataagga   1020
ctaaaaataa aaatatatct ttttggaaa tcgtaccgcg taagaaacat gtataaatac   1080
ctataaggtc ttattttttt ctcttccaat ttcgttgtcga catatttcgc gattcgtcta   1140
aggtaaaaaa aaactcatct tttttctttt tagatcgtta atttttgatc agcgattcgc   1200
tcttctgatc tgtgttcttt aagcttgtct tctctcttga ttcgatctgc tgaaaaccta   1260 gaaattttg atttttttgt tgttttgct ccatgtgtat gggtatattt acgatttaa   1320 caaaacaaaa atatgaattg aggttttta tttagcgaat tgggttttaa ttgttcacat   1380
```

```
tcgtttggct ctctcgaggt gagtgataaa gtatagaact ttcttatgct taggatctta    1440
aattcgagtt ctttgattta cctgtcatgt gttattgatt gatctcattt atattgtgtc    1500
tgcttgatgt ttaaagcttg gtgtatgcaa tttgattggg tttactggag attgatctgt    1560
gacctaatca atgagtgata acattgctgg ttcatctgat ttctcatctg gtgtgtctgc    1620
tcgattccct gaagaaagtt tgaaactcag gcttggtttg tgcagtttga ttgatttatc    1680
tcattacttg actctggtgt acttgattct ttgatgaaag cttgaagtta atgtttggtt    1740
tgtgcaatat gattgggatt aactgcattt gatctctgac caaaatcagt gattaattac    1800
attgcttggt tatctcatta cttgagtttg gtgttcctgc atgatcccct gagcttgaag    1860
ttcatgcttg gtttgtccaa ttgtgaccta aattgatgtt tcttgtggt atcttttcgt    1920 aggttttgtt actgattgag aaaac                                         1945
```

```
<210> SEQ ID NO 14
<211> LENGTH: 1088
<212> TYPE: DNA
<213> ORGANISM: Arabidopsis thaliana
<220> FEATURE:
<221> NAME/KEY: promoter
<222> LOCATION: (1)..(1088)
<223> OTHER INFORMATION: transcription regulating sequence from
      Arabidopsis thaliana gene At5g45350

<400> SEQUENCE: 14
```

```
gctgagcaaa agtctcgacc ttttgtccaa tttcataagg cctactttct gtaaggtctt      60
ctctctctct ctctctctga cctgattctg cctgggttct gtggagttga aatgaatcaa     120
atgtagctct tgttttaatc agtcagcttt gtaacgtata catatatatc attgtatgtg     180
attaacattg tccttaaaaa gtgttacacc tagtaattac gttccaactt tatcagtaaa     240
cctattggta actagtaatt tgctcccgat attggttttc tcattaattt ttatagccat     300
tctttgttca tttaaaccat attacaaatt tgtcctggtt agaactgatt atgatgacaa     360
atcgatgatt agttcaaaat gaagtttata gcaatatatt ctaataacta tacatcaatt     420
atcaccactg atgtgtttga atgaaaaatg aattgataat cttaataaat gtttgatttt     480
atagataagt ataaagtatg aatggattta gaaaatttta gtatttagtg agataagcat     540
aagcaaaact agaaaatgaa aattattatt aaataaattc attaatacac attggcaatg     600
tgacattgcc taaaatcaaa tatgtactaa ttcaattaat gttaataaga atttttttgga    660 ttcgattctc ttgcgaaagt gcaaattaaa agacattctt atctcctacg taaacagaat     720
cacgcgtcca ttgcgcgttc tcgcaacgct aaaatattta cgttggaaaa tattctcata     780
attctctcct ttgccccac agtttaatat atttcataaa cacccccacg agaaattaaa      840
aaccgttcca aatttgaaaa aatacaacaa acaattcatg aaaatattca atctataagc     900
aaaacattgg tagtgttaca tgtgtcgtcc ttcgtgctga aaatttggat agcattgtta     960
attatgacaa cgtaagtgta gcctgtgatt catagtaaaa tataaggact aaaaataaaa    1020 atatatctt tttggaaatc gtaccgcgta agaaacatgt ataaatacct ataaggtctt    1080
attttttt                                                            1088
```

```
<210> SEQ ID NO 15
<211> LENGTH: 1100
<212> TYPE: DNA
<213> ORGANISM: Arabidopsis thaliana
```

```
<220> FEATURE:
<221> NAME/KEY: promoter
<222> LOCATION: (1)..(1100)
<223> OTHER INFORMATION: transcription regulating sequence from
      Arabidopsis thaliana gene At5g45350

<400> SEQUENCE: 15
ccctgaggtt ctgctgagca aaagtctcga ccttttgtcc aatttcataa ggcctacttt      60
ctgtaaggtc ttctctctct ctctctctct gacctgattc tgcctgggtt ctgtggagtt     120
gaaatgaatc aaatgtagct cttgttttaa tcagtcagct ttgtaacgta tacatatata     180
tcattgtatg tgattaacat tgtccttaaa aagtgttaca cctagtaatt acgttccaac     240
tttatcagta aacctattgg taactagtaa tttgctcccg atattggttt tctcattaat     300
ttttatagcc attctttgtt catttaaacc atattacaaa tttgtcctgg ttagaactga     360
ttatgatgac aaatcgatga ttagttcaaa atgaagttta tagcaatata ttctaataac     420
tatacatcaa ttatccaccac tgatgtgttt gaatgaaaaa tgaattgata atcttaataa     480
atgtttgatt ttatagataa gtataaagta tgaatggatt tagaaaattt tagtatttag     540
tgagataagc ataagcaaaa ctagaaaaat gaaattatta ttaaataaat tcattaatac     600
acattggcaa tgtgacattg cctaaaatca aatatgtact aattcaatta atgttaataa     660
gaattttttg gattcgattc tcttgcgaaa gtgcaaatta aaagacattc ttatctccta     720
cgtaaacaga atcacgcgtc cattgcgcgt tctcgcaacg ctaaaatatt tacgttggaa     780
aatattctca taattctctc ctttgccccc acagtttaat atatttcata aacacccccca     840
cgagaaatta aaaccgttc caaatttgaa aaaatacaac aaacaattca tgaaaatatt      900
caatctataa gcaaaacatt ggtagtgtta catgtgtcgt ccttcgtgct gaaaatttgg     960
atagcattgt taattatgac aacgtaagtg tagcctgtga ttcatagtaa aatataagga    1020
ctaaaaataa aaatatatct tttttggaaa tcgtaccgcg taagaaacat gtataaatac    1080
ctataaggtc ttatttttt                                                 1100

<210> SEQ ID NO 16
<211> LENGTH: 862
<212> TYPE: DNA
<213> ORGANISM: Arabidopsis thaliana
<220> FEATURE:
<221> NAME/KEY: CDS
<222> LOCATION: (66)..(599)
<223> OTHER INFORMATION: encoding Arabidopsis thaliana proline-rich
      family protein

<400> SEQUENCE: 16
ctcttccaat ttcgtttcga catatttcgc gattcgtcta aggttttgtt actgattgag      60 aaaac atg gga ggt gac aat gat aat gac aaa gac aaa ggg ttt cat ggg    110
      Met Gly Gly Asp Asn Asp Asn Asp Lys Asp Lys Gly Phe His Gly
       1               5                  10                  15 tat cct ccc gct gga tac cca ccc cct ggg gct tat cca ccc gct gga    158
Tyr Pro Pro Ala Gly Tyr Pro Pro Pro Gly Ala Tyr Pro Pro Ala Gly
             20                  25                  30 tac cca caa caa ggt tac cct cca cca ccc ggt gct tac ccg cct gca    206
Tyr Pro Gln Gln Gly Tyr Pro Pro Pro Gly Ala Tyr Pro Pro Ala
         35                  40                  45 ggt tat cct ccg ggt gcc tac cca cct gct cct ggt ggt tat cct ccc    254
Gly Tyr Pro Pro Gly Ala Tyr Pro Pro Ala Pro Gly Gly Tyr Pro Pro
     50                  55                  60
```

```
gcc cct ggt tat ggt ggt tat cct cca gct cct ggt tat gga ggt tat       302
Ala Pro Gly Tyr Gly Gly Tyr Pro Pro Ala Pro Gly Tyr Gly Gly Tyr
 65                  70                  75 cct cct gca cct ggt cat ggt ggt tac cct cct gct ggc tat cct gct       350
Pro Pro Ala Pro Gly His Gly Gly Tyr Pro Pro Ala Gly Tyr Pro Ala
 80                  85                  90                  95 cat cac tca gga cac gca gga gga att ggg ggt atg att gca ggt gct       398
His His Ser Gly His Ala Gly Gly Ile Gly Gly Met Ile Ala Gly Ala
                100                 105                 110 gca gct gcc tat gga gct cac cac gta gct cat agc tct cac ggt cct       446
Ala Ala Ala Tyr Gly Ala His His Val Ala His Ser Ser His Gly Pro
            115                 120                 125 tac gga cat gct gca tat ggt cac ggt ttt ggc cat ggt cat ggc tat       494
Tyr Gly His Ala Ala Tyr Gly His Gly Phe Gly His Gly His Gly Tyr
        130                 135                 140 ggc tat ggt cat ggt cat ggt aag ttc aag cat ggg aag cac ggg aag       542
Gly Tyr Gly His Gly His Gly Lys Phe Lys His Gly Lys His Gly Lys
145                 150                 155 ttc aag cat ggg aag cat gga atg ttt gga gga ggc aag ttc aag aag       590
Phe Lys His Gly Lys His Gly Met Phe Gly Gly Gly Lys Phe Lys Lys
160                 165                 170                 175 tgg aag tga tctagttaat acctttgtg aatctgtctg gactgaccaa                639
Trp Lys tgtttcaaat aagccctaaa cattatataa gttgactttc gtcggttaga ttgctggttc     699
gagttggaat aattgaaact taattagtat caaatcttat tgtgtacttt aaagctatcg     759
ttggctttat aatgacagat tctggtttcg gtgtgttgtt ttaagatttt tgtatatact     819 gtttttaca ttgcttaagc ttatagaagt catgattatg att                        862

<210> SEQ ID NO 17
<211> LENGTH: 177
<212> TYPE: PRT
<213> ORGANISM: Arabidopsis thaliana

<400> SEQUENCE: 17

Met Gly Gly Asp Asn Asp Asn Asp Lys Asp Lys Gly Phe His Gly Tyr
 1               5                  10                  15

Pro Pro Ala Gly Tyr Pro Pro Gly Ala Tyr Pro Pro Ala Gly Tyr
            20                  25                  30

Pro Gln Gln Gly Tyr Pro Pro Pro Gly Ala Tyr Pro Pro Ala Gly
        35                  40                  45

Tyr Pro Pro Gly Ala Tyr Pro Ala Pro Gly Gly Tyr Pro Pro Ala
     50                  55                  60

Pro Gly Tyr Gly Gly Tyr Pro Pro Ala Pro Gly Tyr Gly Gly Tyr Pro
 65                  70                  75                  80

Pro Ala Pro Gly His Gly Gly Tyr Pro Pro Ala Gly Tyr Pro Ala His
                 85                  90                  95

His Ser Gly His Ala Gly Gly Ile Gly Gly Met Ile Ala Gly Ala Ala
            100                 105                 110

Ala Ala Tyr Gly Ala His His Val Ala His Ser Ser His Gly Pro Tyr
        115                 120                 125

Gly His Ala Ala Tyr Gly His Gly Phe Gly His Gly His Gly Tyr Gly
    130                 135                 140

Tyr Gly His Gly His Gly Lys Phe Lys His Gly Lys His Gly Lys Phe
145                 150                 155                 160
```

```
Lys His Gly Lys His Gly Met Phe Gly Gly Gly Lys Phe Lys Lys Trp
            165                 170                 175

Lys

<210> SEQ ID NO 18
<211> LENGTH: 1235
<212> TYPE: DNA
<213> ORGANISM: Arabidopsis thaliana
<220> FEATURE:
<221> NAME/KEY: promoter
<222> LOCATION: (1)..(1235)
<223> OTHER INFORMATION: transcription regulating sequence from
      Arabidopsis thaliana gene At2g39830

<400> SEQUENCE: 18
ccaaaaacaa gcagccttaa tagaaaataa gttatggatc gtccatacag agatcgactt     60
tagcaagttg ataaagaaat ggtcagatct caaggtggaa actgttgctg aaaaaagcta    120
gatttgatct gatgctgtct ttaacccaaa atattaattt gatcccaaaa aaaggtaat    180 ttaatcgaaa gaaagaactt aaacatgaca ataggttagg cttttgttct gtaaaaattg    240
ggtgtctgat ccactttga agcctctctt tcacctttgc tgcgtcatca ccggtcacga    300
ccttcctata gattgatgcc tcaaattata ataacaata ttattattgg tccgtcgttt    360
gtaatgtcat aaaagcttaa ttcccattat aaagttgtct gtggtaacgt tgcaaaagcg    420
catctttatc gtgtattaga gtatgacctt tgttaatacg cccatattat gtatagtgca    480
aacattgtta tactacttct catggattca tgagtcggat atttgaaacc caaaaacaat    540
tacaagaatc atacaaattt tgaaactaaa gttttagtta aaaaataaaa tgacatatct    600
tcaatgtagc tatagattca ttaaaaactc ggtgagggta tgagaccata aaaacaaaaa    660
caaggaaaat ttaacaaaac caaagtttaa aggcaaatag ttagagccga tggaacgagc    720
gtctccatca aaacccaaaa agaagaattt ttttttgctt tcgtttacaa atctaacttt    780 ttggttttc tccccaacaa aaaaaaaaa aataaagtgt aaaaagagag aagcttaaaa    840
ggtttcaact atcttcctcc tccccacacc gttgcttgaa ggattcttcc gcctcagcaa    900
aaaccaaaaa gacaaaaata ttctcttaaa aaaacatctc tttctctctg ttcctttcct    960
ttcagaagct aagcatctct tccttttctt tttctctttt aattttttt tgcccgatct   1020 cttctgcaaa gattctctct ttcttctc tcttttcatt tatgttttca ttctctaata   1080
acaaattgta atgacttata acttcttctt cttctcccct cttccttctt cttcctcctc   1140
ctcttctctt ctttgcttct ctctccggcc gtcgttttcg ctttactcac acgtttcaa   1200 gtatatttaa tcacgtgggg gccatttttc catcc                              1235

<210> SEQ ID NO 19
<211> LENGTH: 1249
<212> TYPE: DNA
<213> ORGANISM: Arabidopsis thaliana
<220> FEATURE:
<221> NAME/KEY: promoter
<222> LOCATION: (1)..(1249)
<223> OTHER INFORMATION: transcription regulating sequence from
      Arabidopsis thaliana gene At2g39830

<400> SEQUENCE: 19
aaatgagaat tcccaaaaac aagcagcctt aatagaaaat aagttatgga tcgtccatac     60
agagatcgac tttagcaagt tgataaagaa atggtcagat ctcaaggtgg aaactgttgc    120
tgaaaaaagc tagatttgat ctgatgctgt ctttaaccca aatattaat tgatcccaa    180
```

| | |
|---|---|
| aaaaaaggta atttaatcga aagaaagaac ttaaacatga caataggtta ggcttttgtt | 240 |
| ctgtaaaaat tgggtgtctg attccacttt gaagcctctc tttcacctttt gctgcgtcat | 300 |
| caccggtcac gaccttccta tagattgatg cctcaaatta taaataacaa tattattatt | 360 |
| ggtccgtcgt ttgtaatgtc ataaaagctt aattcccatt ataaagttgt ctgtggtaac | 420 |
| gttgcaaaag cgcatcttta tcgtgtatta gagtatgacc tttgttaata cgcccatatt | 480 |
| atgtatagtg caaacattgt tatactactt ctcatggatt catgagtcgg atatttgaaa | 540 |
| cccaaaaaca attacaagaa tcatacaaat tttgaaacta agttttagt taaaaaataa | 600 |
| aatgacatat cttcaatgta gctatagatt cattaaaaac tcggtgaggg tatgagacca | 660 |
| taaaaacaaa aacaaggaaa atttaacaaa accaaagttt aaaggcaaat agttagagcc | 720 |
| gatgaacga gcgtctccat caaaacccaa aagaagaat ttttttttgc tttcgtttac | 780 |
| aaatctaact ttttggttttt tctccccaac aaaaaaaaaa aaaataaagt gtaaaaagag | 840 |
| agaagcttaa aaggtttcaa ctatcttcct cctccccaca ccgttgcttg aaggattctt | 900 |
| ccgcctcagc aaaaaccaaa aagacaaaaa tattctctta aaaaacatc tctttctctc | 960 |
| tgttcctttc ctttcagaag ctaagcatct cttccttttc ttttctctt ttaattttt | 1020 |
| tttgcccgat ctcttctgca aagattctct cttcttttct tctcttttca tttatgtttt | 1080 |
| cattctctaa taacaaattg taatgactta taacttcttc ttcttctccc ctcttccttc | 1140 |
| ttcttcctcc tcctcttctc ttctttgctt ctctctccgg ccgtcgtttt cgctttactc | 1200 |
| acacgttttc aagtatattt aatcacgtgg gggccatttt tccatcctc | 1249 |

```
<210> SEQ ID NO 20
<211> LENGTH: 1135
<212> TYPE: DNA
<213> ORGANISM: Arabidopsis thaliana
<220> FEATURE:
<221> NAME/KEY: promoter
<222> LOCATION: (1)..(1135)
<223> OTHER INFORMATION: transcription regulating sequence from
      Arabidopsis thaliana gene At2g39830

<400> SEQUENCE: 20
```

| | |
|---|---|
| ccaaaaacaa gcagccttaa tagaaaataa gttatggatc gtccatacag agatcgactt | 60 |
| tagcaagttg ataagaaat ggtcagatct caaggtggaa actgttgctg aaaaaagcta | 120 |
| gatttgatct gatgctgtct ttaacccaaa atattaattt gatcccaaaa aaaaggtaat | 180 |
| ttaatcgaaa gaaagaactt aaacatgaca ataggttagg cttttgttct gtaaaaattg | 240 |
| ggtgtctgat tccactttga agcctctctt tcacctttgc tgcgtcatca ccggtcacga | 300 |
| ccttcctata gattgatgcc tcaaattata ataacaata ttattattgg tccgtcgttt | 360 |
| gtaatgtcat aaaagcttaa ttcccattat aaagttgtct gtggtaacgt tgcaaaagcg | 420 |
| catctttatc gtgtattaga gtatgacctt tgttaatacg cccatattat gtatagtgca | 480 |
| aacattgtta tactacttct catggattca tgagtcggat atttgaaacc caaaaacaat | 540 |
| tacaagaatc atacaaattt tgaaactaaa gttttagtta aaaataaaa tgacatatct | 600 |
| tcaatgtagc tatagattca ttaaaaactc ggtgagggta tgagaccata aaaacaaaaa | 660 |
| caaggaaaat ttaacaaaac caaagtttaa aggcaaatag ttagagccga tggaacgagc | 720 |
| gtctccatca aaacccaaaa agaagaattt tttttgctt tcgttacaa atctaacttt | 780 |
| ttggttttc tccccaacaa aaaaaaaaa aataaagtgt aaaaagagag aagcttaaaa | 840 |
| ggtttcaact atcttcctcc tccccacacc gttgcttgaa ggattcttcc gcctcagcaa | 900 |

| | |
|---|---|
| aaaccaaaaa gacaaaaata ttctcttaaa aaaacatctc tttctctctg ttcctttcct | 960 |
| ttcagaagct aagcatctct tccttttctt tttctctttt aatttttttt tgcccgatct | 1020 |
| cttctgcaaa gattctctct ttcttttctt tcttttcatt tatgttttca ttctctaata | 1080 |
| acaaattgta atgacttata acttcttctt cttctcccct cttccttctt cttcc | 1135 |

<210> SEQ ID NO 21
<211> LENGTH: 1147
<212> TYPE: DNA
<213> ORGANISM: Arabidopsis thaliana
<220> FEATURE:
<221> NAME/KEY: promoter
<222> LOCATION: (1)..(1147)
<223> OTHER INFORMATION: transcription regulating sequence from
    Arabidopsis thaliana gene At2g39830

<400> SEQUENCE: 21

| | |
|---|---|
| aaatgagaat tcccaaaaac aagcagcctt aatagaaaat aagttatgga tcgtccatac | 60 |
| agagatcgac tttagcaagt tgataaagaa atggtcagat ctcaaggtgg aaactgttgc | 120 |
| tgaaaaaagc tagatttgat ctgatgctgt ctttaaccca aaatattaat ttgatcccaa | 180 |
| aaaaaaggta atttaatcga aagaaagaac ttaaacatga caataggtta ggcttttgtt | 240 |
| ctgtaaaaat tgggtgtctg attccacttt gaagcctctc tttcacctttt gctgcgtcat | 300 |
| caccggtcac gaccttccta tagattgatg cctcaaatta taaataacaa tattattatt | 360 |
| ggtccgtcgt ttgtaatgtc ataaaagctt aattcccatt ataaagttgt ctgtggtaac | 420 |
| gttgcaaaag cgcatcttta tcgtgtatta gagtatgacc tttgttaata cgcccatatt | 480 |
| atgtatagtg caaacattgt tatactactt ctcatggatt catgagtcgg atatttgaaa | 540 |
| cccaaaaaca attacaagaa tcatacaaat tttgaaacta agttttagt taaaaaataa | 600 |
| aatgacatat cttcaatgta gctatagatt cattaaaaac tcggtgaggg tatgagacca | 660 |
| taaaaacaaa aacaaggaaa atttaacaaa accaaagttt aaaggcaaat agttagagcc | 720 |
| gatggaacga gcgtctccat caaaacccaa aagaagaat ttttttttgc tttcgtttac | 780 |
| aaatctaact ttttggtttt tctccccaac aaaaaaaaaa aaaataaagt gtaaaaagag | 840 |
| agaagcttaa aaggtttcaa ctatcttcct cctccccaca ccgttgcttg aaggattctt | 900 |
| ccgcctcagc aaaaaccaaa aagacaaaaa tattctctta aaaaaacatc tctttctctc | 960 |
| tgttcctttc ctttcagaag ctaagcatct cttccttttc tttttctctt ttaatttttt | 1020 |
| tttgcccgat ctcttctgca agattctct cttctttct tctcttttca tttatgtttt | 1080 |
| cattctctaa taacaaattg taatgactta taacttcttc ttcttctccc ctcttccttc | 1140 |
| ttcttcc | 1147 |

<210> SEQ ID NO 22
<211> LENGTH: 2399
<212> TYPE: DNA
<213> ORGANISM: Arabidopsis thaliana
<220> FEATURE:
<221> NAME/KEY: promoter
<222> LOCATION: (1)..(2399)
<223> OTHER INFORMATION: transcription regulating sequence from
    Arabidopsis thaliana gene At2g39830

<400> SEQUENCE: 22

| | |
|---|---|
| cttttttggc gggaaaatgt tgattttttt tttggtggta aactgttaaa tcgcggttta | 60 |
| ggagaaaaaa atgtgaaatc ttttttgaca aaaaaatgtt gattcacttg aaaaatgatt | 120 |
| ttaaaaaaaa tcgtgggtac ccataaccca atgaggtaaa cccatatgtg ttttatttat | 180 |

```
ttggatacccc agcccatttt aaacctgtgt tttatttcca gaaaaaatag atctatgagc      240
ttaaaatttt atgtgtgttt tgggtaccag tggattttaa cccatcatta acatctctag      300
gtacggtact ctagtggtgg cctacattgg ttgataaagt cataaagtca atatcgttta      360
aacatgcaaa tgcaaatttt atggaccgga ttaagtcgga atgatccgta tgttgaggct      420
tgaaagagcc catcaatgca atggaaaata gtcgtctctt ttcttttcct ttcttttctt      480
tacgatcata aagttctctt tttttttggg tgaatattgt aaaggttttg agtcattctt      540
tccaactcaa ttccacgttt ctcatctctc aaggcttttt actacaaaaa tctttacaga      600
tacaaagtta gagatttata acaacttgga taagatgtct catgcatgag ataagagaaa      660
gtaaattctt gtatttttagg tgattaaagg aataaagaca tatgcagcat ttttgcatcg      720
gctactcaaa ctcagctaaa ttcttcgcta tatatatata ctttattttg ttacaataat      780
tgtatcagac taatacaact tgatccatgt gtaggaaagt ttcaataaga ttgatcgttt      840
ttatgttacc aaaaataaaa aaagattgat cgtttaaaaa gtcattctta acaagaaata      900
aatacttgtt gaactagaag tctagaacaa atacatttgt tcagacattt taaattgtaa      960
gattaattac attcacaaaa aaaattgtaa gattaactga ggaatataat gatgtaatag     1020
gaaactaacg caaatgctta aaatgtttta acattttcat gatgaaaaat aagtaaacat     1080
ctttgggggt atagatactt aagataaaat atataacttg acaagaaaaa agaaaagata     1140
agcattttct ttaaatgaga attcccaaaa acaagcagcc ttaatagaaa ataagttatg     1200
gatcgtccat acagagatcg actttagcaa gttgataaag aaatggtcag atctcaaggt     1260
ggaaactgtt gctgaaaaaa gctagatttg atctgatgct gtcttttaacc caaaatatta     1320 atttgatccc aaaaaaaagg taatttaatc gaaagaaaga acttaaacat gacaataggt     1380
taggcttttg ttctgtaaaa attgggtgtc tgattccact ttgaagcctc tctttcacct     1440
ttgctgcgtc atcaccggtc acgaccttcc tatagattga tgcctcaaat tataaataac     1500
aatattatta ttggtccgtc gtttgtaatg tcataaaagc ttaattccca ttataaagtt     1560
gtctgtggta acgttgcaaa agcgcatctt tatcgtgtat tagagtatga cctttgttaa     1620
tacgcccata ttatgtatag tgcaaacatt gttatactac ttctcatgga ttcatgagtc     1680
ggatatttga aacccaaaaa caattacaag aatcatacaa attttgaaac taagttttta     1740
gttaaaaaat aaaatgacat atcttcaatg tagctataga ttcattaaaa actcggtgag     1800
ggtatgagac cataaaaaca aaacaaggaa aaatttaaca aaaccaaagt ttaaaggcaa     1860
atagttagag ccgatggaac gagcgtctcc atcaaaaccc aaaaagaaga attttttttt     1920
gctttcgttt acaaatctaa ctttttggtt tttctcccca acaaaaaaaa aaaaaataaa     1980
gtgtaaaaag agagaagctt aaaaggtttc aactatcttc ctcctcccca caccgttgct     2040
tgaaggattc ttccgcctca gcaaaaacca aaagacaaa atattctct taaaaaaaca     2100 tctctttctc tctgttccctt tcctttcaga agctaagcat ctcttccttt tcttttctc     2160 ttttaatttt tttttgcccg atctcttctg caagagattct ctctttcttt cttctctttt     2220
catttatgtt tcattctctc aataacaaat tgtaatgact tataacttct tcttcttctc     2280
ccctcttcct tcttcttcct cctcctcttc tcttctttgc ttctctctcc ggccgtcgtt     2340
ttcgctttac tcacacgttt tcaagtatat ttaatcacgt gggggccatt tttccatcc     2399
```

<210> SEQ ID NO 23
<211> LENGTH: 2413
<212> TYPE: DNA
<213> ORGANISM: Arabidopsis thaliana

```
<220> FEATURE:
<221> NAME/KEY: promoter
<222> LOCATION: (1)..(2413)
<223> OTHER INFORMATION: transcription regulating sequence from
      Arabidopsis thaliana gene At2g39830

<400> SEQUENCE: 23
aattttgaat gtcttttttg gcgggaaaat gttgattttt tttttggtgg taaactgtta      60
aatcgcggtt taggagaaaa aaatgtgaaa tcttttttga caaaaaaatg ttgattcact     120
tgaaaaatga ttttaaaaaa aatcgtgggt acccataacc caatgaggta aacccatatg     180
tgttttattt atttggatac ccagcccatt ttaaacctgt gttttatttc cagaaaaaat     240
agatctatga gcttaaaatt ttatgtgtgt tttgggtacc agtggatttt aacccatcat     300
taacatctct aggtacggta ctctagtggt ggcctacatt ggttgataaa gtcataaagt     360
caatatcgtt taaacatgca aatgcaaatt ttatggaccg gattaagtcg aatgatccg     420
tatgttgagg cttgaaagag cccatcaatg caatggaaaa tagtcgtctc ttttcttttc     480
ctttcttttc tttacgatca taaagttctc ttttttttg ggtgaatatt gtaaaggttt      540
tgagtcattc tttccaactc aattccacgt ttctcatctc tcaaggcttt ttactacaaa     600
aatctttaca gatacaaagt tagagattta taacaacttg gataagatgt ctcatgcatg     660
agataagaga aagtaaattc ttgtatttta ggtgattaaa ggaataaaga catatgcagc     720
atttttgcat cggctactca aactcagcta aattcttcgc tatatatata tactttatt     780
tgttacaata attgtatcag actaatacaa cttgatccat gtgtaggaaa gtttcaataa     840
gattgatcgt ttttatgtta ccaaaaataa aaaagattg atcgtttaaa aagtcattct     900
taacaagaaa taaatacttg ttgaactaga agtctagaac aaatacattt gttcagacat     960
tttaaattgt aagattaatt acattcacaa aaaaaattgt aagattaact gaggaatata    1020
atgatgtaat aggaaactaa cgcaaatgct taaaatgttt taacattttc atgatgaaaa    1080
ataagtaaac atctttgggg gtatagatac ttaagataaa atatataact tgacaagaaa    1140
aaagaaaaga taagcatttt ctttaaatga gaattcccaa aaacaagcag ccttaataga    1200
aaataagtta tggatcgtcc atacagagat cgactttagc aagttgataa agaaatggtc    1260
agatctcaag gtggaaactg ttgctgaaaa aagctagatt tgatctgatg ctgtctttaa    1320
cccaaaatat taatttgatc ccaaaaaaaa ggtaatttaa tcgaaagaaa gaacttaaac    1380
atgacaatag gttaggcttt tgttctgtaa aaattgggtg tctgattcca ctttgaagcc    1440
tctctttcac ctttgctgcg tcatcaccgg tcacgacctt cctatagatt gatgcctcaa    1500
attataaata acaatattat tattggtccg tcgtttgtaa tgtcataaaa gcttaattcc    1560
cattataaag ttgtctgtgg taacgttgca aaagcgcatc tttatcgtgt attagagtat    1620
gacctttgtt aatacgccca tattatgtat agtgcaaaca ttgttatact acttctcatg    1680
gattcatgag tcggatattt gaaacccaaa aacaattaca agaatcatac aaattttgaa    1740
actaaagttt tagttaaaaa ataaaatgac atatcttcaa tgtagctata gattcattaa    1800
aaactcggtg agggtatgag accataaaaa caaaacaag gaaatttaa caaaccaaa       1860
gtttaaaggc aaatagttag agccgatgga acgagcgtct ccatcaaaac ccaaaaagaa    1920
gaattttttt ttgctttcgt ttacaaatct aacttttttgg ttttctccc caacaaaaaa    1980
aaaaaaaata aagtgtaaaa agagagaagc ttaaaaggtt tcaactatct tcctcctccc    2040
cacaccgttg cttgaaggat tcttccgcct cagcaaaaac caaaaagaca aaatattct     2100
cttaaaaaaa catctctttc tctctgttcc tttccttttca gaagctaagc atctcttcct    2160
```

```
tttcttttc  tcttttaatt  ttttttgcc  cgatctcttc  tgcaaagatt  ctctctttct    2220
ttcttctctt  ttcatttatg  ttttcattct  ctaataacaa  attgtaatga  cttataactt   2280
cttcttcttc  tccctcttc   cttcttcttc  ctcctcctct  tctcttcttt  gcttctctct   2340
ccggccgtcg  ttttcgcttt  actcacacgt  tttcaagtat  atttaatcac  gtggggcca    2400 tttttccatc  ctc                                                          2413

<210> SEQ ID NO 24
<211> LENGTH: 2299
<212> TYPE: DNA
<213> ORGANISM: Arabidopsis thaliana
<220> FEATURE:
<221> NAME/KEY: promoter
<222> LOCATION: (1)..(2299)
<223> OTHER INFORMATION: transcription regulating sequence from
      Arabidopsis thaliana gene At2g39830

<400> SEQUENCE: 24
cttttttggc  gggaaaatgt  tgattttttt  tttggtggta  aactgttaaa  tcgcggttta     60
ggagaaaaaa  atgtgaaatc  ttttttgaca  aaaaaatgtt  gattcacttg  aaaaatgatt   120
ttaaaaaaaa  tcgtgggtac  ccataaccca  atgaggtaaa  cccatatgtg  ttttatttat   180
ttggataccc  agcccatttt  aaacctgtgt  tttatttcca  gaaaaaatag  atctatgagc   240
ttaaaatttt  atgtgtgttt  tgggtaccag  tggattttaa  cccatcatta  acatctctag   300
gtacggtact  ctagtggtgg  cctacattgg  ttgataaagt  cataaagtca  atatcgttta   360
aacatgcaaa  tgcaaatttt  atggaccgga  ttaagtcgga  atgatccgta  tgttgaggct   420
tgaaagagcc  catcaatgca  atggaaaata  gtcgtctctt  ttcttttcct  ttcttttctt   480
tacgatcata  aagttctctt  ttttttgg    tgaatattgt  aaaggttttg  agtcattctt   540
tccaactcaa  ttccacgttt  ctcatctctc  aaggctttt   actacaaaaa  tctttacaga   600
tacaaagtta  gagatttata  acaacttgga  taagatgtct  catgcatgag  ataagagaaa   660
gtaaattctt  gtattttagg  tgattaaagg  aataaagaca  tatgcagcat  ttttgcatcg   720
gctactcaaa  ctcagctaaa  ttcttcgcta  tatatatata  ctttattttg  ttacaataat   780
tgtatcagac  taatacaact  tgatccatgt  gtaggaaagt  ttcaataaga  ttgatcgttt   840
ttatgttacc  aaaaataaaa  aaagattgat  cgtttaaaaa  gtcattctta  acaagaaata   900
aatacttgtt  gaactagaag  tctagaacaa  atacatttgt  tcagacattt  taaattgtaa   960
gattaattac  attcacaaaa  aaattgtaa   gattaactga  ggaatataat  gatgtaatag  1020
gaaactaacg  caaatgctta  aaatgtttta  acattttcat  gatgaaaaat  aagtaaacat  1080 ctttggggt   atagatactt  aagataaaat  atataacttg  acaagaaaaa  agaaaagata  1140 agcatttct   ttaaatgaga  attcccaaaa  acaagcagcc  ttaatagaaa  ataagttatg  1200
gatcgtccat  acagagatcg  actttagcaa  gttgataaag  aaatggtcag  atctcaaggt  1260
ggaaactgtt  gctgaaaaaa  gctagatttg  atctgatgct  gtctttaacc  caaaatatta  1320
atttgatccc  aaaaaaaagg  taatttaatc  gaaagaaaga  acttaaacat  gacaataggt  1380
taggcttttg  ttctgtaaaa  attgggtgtc  tgattccact  tgaagcctc   tctttcacct  1440 ttgctgcgtc  atcaccggtc  acgaccttcc  tatagattga  tgcctcaaat  tataaataac  1500
aatattatta  ttggtccgtc  gtttgtaatg  tcataaaagc  ttaattccca  ttataaagtt  1560
gtctgtggta  acgttgcaaa  agcgcatctt  tatcgtgtat  tagagtatga  cctttgttaa  1620
tacgcccata  ttatgtatag  tgcaaacatt  gttatactac  ttctcatgga  ttcatgagtc  1680
```

```
ggatatttga aacccaaaaa caattacaag aatcatacaa attttgaaac taaagtttta    1740
gttaaaaaat aaaatgacat atcttcaatg tagctatata ttcattaaaa actcggtgag    1800
ggtatgagac cataaaaaca aaaacaagga aaatttaaca aaaccaaagt ttaaaggcaa    1860
atagttagag ccgatggaac gagcgtctcc atcaaaaccc aaaagaaga attttttttt    1920 gctttcgttt acaaatctaa cttttttggtt tttctcccca acaaaaaaaa aaaaaataaa    1980
gtgtaaaaag agagaagctt aaaaggtttc aactatcttc ctcctcccca caccgttgct    2040
tgaaggattc ttccgcctca gcaaaaacca aaaagacaaa atattctct taaaaaaaca    2100 tctctttctc tctgttccttt tcctttcaga agctaagcat ctcttccttt tcttttttctc    2160 ttttaatttt tttttgcccg atctcttctg caaagattct ctctttctttt cttctctttt    2220 catttatgtt ttcattctct aataacaaat tgtaatgact taaacttct tcttcttctc    2280 ccctcttcct tcttcttcc                                                  2299

<210> SEQ ID NO 25
<211> LENGTH: 2311
<212> TYPE: DNA
<213> ORGANISM: Arabidopsis thaliana
<220> FEATURE:
<221> NAME/KEY: promoter
<222> LOCATION: (1)..(2311)
<223> OTHER INFORMATION: transcription regulating sequence from
      Arabidopsis thaliana gene At2g39830

<400> SEQUENCE: 25
aattttgaat gtcttttttg gcgggaaaat gttgattttt ttttggtgg taaactgtta      60 aatcgcggtt taggagaaaa aaatgtgaaa tcttttttga caaaaaatg ttgattcact     120 tgaaaaatga tttaaaaaa aatcgtgggt acccataacc caatgaggta aacccatatg     180
tgttttattt atttggatac ccagcccatt ttaaacctgt gttttatttc cagaaaaaat     240
agatctatga gcttaaaatt ttatgtgtgt tttgggtacc agtggatttt aacccatcat     300
taacatctct aggtacggta ctctagtggt ggcctacatt ggttgataaa gtcataaagt     360
caatatcgtt taaacatgca aatgcaaatt ttatggaccg gattaagtcg gaatgatccg     420
tatgttgagg cttgaaagag cccatcaatg caatggaaaa tagtcgtctc ttttcttttc     480
cttttttttc tttacgatca taaagttctc tttttttttg ggtgaatatt gtaaaggttt     540
tgagtcattc tttccaactc aattccacgt ttctcatctc tcaaggcttt ttactacaaa     600
aatctttaca gatacaaagt tagagattta taacaacttg gataagatgt ctcatgcatg     660
agataagaga aagtaaattc ttgtatttta ggtgattaaa ggaataaaga catatgcagc     720
atttttgcat cggctactca aactcagcta aattcttcgc tatatatata tactttattt     780
tgttacaata attgtatcag actaatacaa cttgatccat gtgtaggaaa gtttcaataa     840
gattgatcgt ttttatgtta ccaaaaataa aaaaagattg atcgtttaaa aagtcattct     900
taacaagaaa taaatacttg ttgaactaga agtctagaac aaatacattt gttcagacat     960
tttaaattgt aagattaatt acattcacaa aaaaaattgt aagattaact gaggaatata    1020
atgatgtaat aggaaactaa cgcaaatgct taaaatgttt taacattttc atgatgaaaa    1080
ataagtaaac atctttgggg gtatagatac ttaagataaa atatataact tgacaagaaa    1140
aaagaaaaga taagcatttt ctttaaatga gaattcccaa aaacaagcag ccttaataga    1200
aaataagtta tggatcgtcc atacagagat cgactttagc aagttgataa agaaatggtc    1260
agatctcaag gtggaaactg ttgctgaaaa aagctagatt tgatctgatg ctgtctttaa    1320
```

-continued

```
cccaaaatat taatttgatc ccaaaaaaaa ggtaatttaa tcgaaagaaa gaacttaaac    1380
atgacaatag gttaggcttt tgttctgtaa aaattgggtg tctgattcca ctttgaagcc    1440
tctctttcac ctttgctgcg tcatcaccgg tcacgacctt cctatagatt gatgcctcaa    1500
attataaata acaatattat tattggtccg tcgtttgtaa tgtcataaaa gcttaattcc    1560
cattataaag ttgtctgtgg taacgttgca aaagcgcatc tttatcgtgt attagagtat    1620
gacctttgtt aatacgccca tattatgtat agtgcaaaca ttgttatact acttctcatg    1680
gattcatgag tcggatattt gaaacccaaa acaattaca agaatcatac aaattttgaa    1740
actaaagttt tagttaaaaa ataaaatgac atatcttcaa tgtagctata gattcattaa    1800
aaactcggtg agggtatgag accataaaaa caaaacaag gaaaatttaa caaaaccaaa    1860
gtttaaaggc aaatagttag agccgatgga acgagcgtct ccatcaaaac ccaaaaagaa    1920
gaattttttt ttgctttcgt ttacaaatct aacttttttgg ttttctccc caacaaaaaa    1980 aaaaaaaata aagtgtaaaa agagagaagc ttaaaaggtt tcaactatct tcctcctccc    2040
cacaccgttg cttgaaggat tcttccgcct cagcaaaaac caaaaagaca aaaatattct    2100
cttaaaaaaa catctctttc tctctgttcc tttccttttca gaagctaagc atctcttcct    2160 tttcttttttc tcttttaatt ttttttttgcc cgatctcttc tgcaaagatt ctctctttct    2220
ttcttctctt ttcatttatg ttttcattct ctaataacaa attgtaatga cttataactt    2280
cttcttcttc tccctcttc cttcttcttc c                                    2311
```

<210> SEQ ID NO 26
<211> LENGTH: 1787
<212> TYPE: DNA
<213> ORGANISM: Arabidopsis thaliana
<220> FEATURE:
<221> NAME/KEY: CDS
<222> LOCATION: (103)..(1614)
<223> OTHER INFORMATION: encoding LIM domain-containing protein

<400> SEQUENCE: 26

```
tcctcctctt ctcttctttg cttctctctc cggccgtcgt tttcgcttta ctcacacgtt     60
ttcaagtata tttaatcacg tgggggccat ttttccatcc tc atg gat tct tct        114
                                               Met Asp Ser Ser
                                                 1 tcc tct tcc tct tct tct tct cct tct tct tcc tac ggt gtt gct cgt      162
Ser Ser Ser Ser Ser Ser Ser Pro Ser Ser Ser Tyr Gly Val Ala Arg
 5                   10                  15                  20 gtc agc cat atc tcc aat cct tgc atc ttc ggg gaa gtt ggg tcg tca      210
Val Ser His Ile Ser Asn Pro Cys Ile Phe Gly Glu Val Gly Ser Ser
                 25                  30                  35 tct tcg tca acg tat aga gat aag aaa tgg aag ttg atg aaa tgg gtg      258
Ser Ser Ser Thr Tyr Arg Asp Lys Lys Trp Lys Leu Met Lys Trp Val
             40                  45                  50 agt aaa ctt ttc aag agt ggc tcg aat ggt ggt ggt agt ggt gct cac      306
Ser Lys Leu Phe Lys Ser Gly Ser Asn Gly Gly Gly Ser Gly Ala His
         55                  60                  65 act aat cat cat cct cct cag ttt caa gaa gac gag aat atg gtc ttt      354
Thr Asn His His Pro Pro Gln Phe Gln Glu Asp Glu Asn Met Val Phe
     70                  75                  80 cct cta cct cct tct tct ttg gat gat cgg tca aga ggt gca cgg gac      402
Pro Leu Pro Pro Ser Ser Leu Asp Asp Arg Ser Arg Gly Ala Arg Asp
 85                  90                  95                 100 aaa gaa gaa ctc gac cgt tca att tca ctt tct cta gct gac aac acg      450
Lys Glu Glu Leu Asp Arg Ser Ile Ser Leu Ser Leu Ala Asp Asn Thr
                105                 110                 115
```

| | | |
|---|---|---|
| aag cgc cca cat ggg tat ggt tgg tct atg gat aac aac cga gat ttt<br>Lys Arg Pro His Gly Tyr Gly Trp Ser Met Asp Asn Asn Arg Asp Phe<br>120 125 130 | | 498 |
| cca agg cct ttt cac ggt ggc ttg aat cca tca tct ttc att cca cct<br>Pro Arg Pro Phe His Gly Gly Leu Asn Pro Ser Ser Phe Ile Pro Pro<br>135 140 145 | | 546 |
| tat gag cct tcc tat caa tat aga cga aga caa aga ata tgt ggc ggt<br>Tyr Glu Pro Ser Tyr Gln Tyr Arg Arg Arg Gln Arg Ile Cys Gly Gly<br>150 155 160 | | 594 |
| tgc aat agc gat att gga tcg ggg aac tat cta gga tgc atg ggc aca<br>Cys Asn Ser Asp Ile Gly Ser Gly Asn Tyr Leu Gly Cys Met Gly Thr<br>165 170 175 180 | | 642 |
| ttc ttt cat cct gaa tgc ttc cgt tgc cat tct tgt ggt tat gct atc<br>Phe Phe His Pro Glu Cys Phe Arg Cys His Ser Cys Gly Tyr Ala Ile<br>185 190 195 | | 690 |
| act gag cat gag ata cca act aat gat gct ggc ttg atc gag tat cga<br>Thr Glu His Glu Ile Pro Thr Asn Asp Ala Gly Leu Ile Glu Tyr Arg<br>200 205 210 | | 738 |
| tgc cat ccg ttt tgg aac caa aag tat tgc ccg tct cac gaa tat gat<br>Cys His Pro Phe Trp Asn Gln Lys Tyr Cys Pro Ser His Glu Tyr Asp<br>215 220 225 | | 786 |
| aaa act gct cgt tgt tgt agc tgc gaa cgt ttg gag tca tgg gat gtg<br>Lys Thr Ala Arg Cys Cys Ser Cys Glu Arg Leu Glu Ser Trp Asp Val<br>230 235 240 | | 834 |
| aga tat tac acg tta gag gat ggg aga agt ttg tgt tta gaa tgt atg<br>Arg Tyr Tyr Thr Leu Glu Asp Gly Arg Ser Leu Cys Leu Glu Cys Met<br>245 250 255 260 | | 882 |
| gaa acc gcg ata acc gat act gga gaa tgt caa ccg ctt tac cac gct<br>Glu Thr Ala Ile Thr Asp Thr Gly Glu Cys Gln Pro Leu Tyr His Ala<br>265 270 275 | | 930 |
| ata aga gac tat tac gaa gga atg tac atg aaa ctt gat caa cag att<br>Ile Arg Asp Tyr Tyr Glu Gly Met Tyr Met Lys Leu Asp Gln Gln Ile<br>280 285 290 | | 978 |
| cct atg ctt ctt gtt caa aga gaa gct ctc aat gat gct atc gta gga<br>Pro Met Leu Leu Val Gln Arg Glu Ala Leu Asn Asp Ala Ile Val Gly<br>295 300 305 | | 1026 |
| gag aaa aac gga tac cat cac atg cct gag aca aga ggt tta tgc ttg<br>Glu Lys Asn Gly Tyr His His Met Pro Glu Thr Arg Gly Leu Cys Leu<br>310 315 320 | | 1074 |
| tct gaa gaa caa aca gtt aca agt gtt ctt aga aga ccg aga ctt ggt<br>Ser Glu Glu Gln Thr Val Thr Ser Val Leu Arg Arg Pro Arg Leu Gly<br>325 330 335 340 | | 1122 |
| gct cac cgt ctt gtt ggt atg aga act cag cct caa agg ctt aca cgc<br>Ala His Arg Leu Val Gly Met Arg Thr Gln Pro Gln Arg Leu Thr Arg<br>345 350 355 | | 1170 |
| aaa tgt gaa gtc aca gcg att cta gtt ctt tac ggg ctc ccg cga tta<br>Lys Cys Glu Val Thr Ala Ile Leu Val Leu Tyr Gly Leu Pro Arg Leu<br>360 365 370 | | 1218 |
| ctg acc gga gca att ctc gcc cat gag ctc atg cat gga tgg cta agg<br>Leu Thr Gly Ala Ile Leu Ala His Glu Leu Met His Gly Trp Leu Arg<br>375 380 385 | | 1266 |
| ctt aat ggt aca tac tgg ttt agg aac ctt aac cct gag gta gag gaa<br>Leu Asn Gly Thr Tyr Trp Phe Arg Asn Leu Asn Pro Glu Val Glu Glu<br>390 395 400 | | 1314 |
| gga atc tgc caa gtc ctc tct tac atg tgg ctt gaa tct gaa gtt ctc<br>Gly Ile Cys Gln Val Leu Ser Tyr Met Trp Leu Glu Ser Glu Val Leu<br>405 410 415 420 | | 1362 |
| tca gat cct tca aca aga aac ttg cct tca aca tca tcg gtg gcc aca<br>Ser Asp Pro Ser Thr Arg Asn Leu Pro Ser Thr Ser Ser Val Ala Thr<br>425 430 435 | | 1410 |

```
tca tca tca tca tcc ttc tcg aac aag aaa gga gga aaa tca aac gtg   1458
Ser Ser Ser Ser Ser Phe Ser Asn Lys Lys Gly Gly Lys Ser Asn Val
            440                 445                 450 gag aag aaa ctt gga gag ttc ttt aaa cat cag ata gct cat gat gcg   1506
Glu Lys Lys Leu Gly Glu Phe Phe Lys His Gln Ile Ala His Asp Ala
            455                 460                 465 tct cca gct tat gga gga ggt ttc agg gca gca aat gca gcg gct tgt   1554
Ser Pro Ala Tyr Gly Gly Gly Phe Arg Ala Ala Asn Ala Ala Ala Cys
    470                 475                 480 aag tac ggt ctt cgt cga aca ctc gat cat atc cgc tta act gga act   1602
Lys Tyr Gly Leu Arg Arg Thr Leu Asp His Ile Arg Leu Thr Gly Thr
485                 490                 495                 500 ttt cct ttg tga tcagatttaa tgttatgtgt catcttgcta tatgttcttg       1654
Phe Pro Leu atttggattt gatggatcac acagcgtttg tgttaacttt aaatagaatc tcaagacaga 1714 ctttatctcc ccttggattt tgaatgggga tatttgttgc ttggagattt tataagaaca 1774 atgactgaat act                                                    1787

<210> SEQ ID NO 27
<211> LENGTH: 503
<212> TYPE: PRT
<213> ORGANISM: Arabidopsis thaliana

<400> SEQUENCE: 27

Met Asp Ser Ser Ser Ser Ser Ser Ser Pro Ser Ser Tyr
1               5                   10                  15

Gly Val Ala Arg Val Ser His Ile Ser Asn Pro Cys Ile Phe Gly Glu
            20                  25                  30

Val Gly Ser Ser Ser Ser Thr Tyr Arg Asp Lys Lys Trp Lys Leu
        35                  40                  45

Met Lys Trp Val Ser Lys Leu Phe Lys Ser Gly Ser Asn Gly Gly Gly
    50                  55                  60

Ser Gly Ala His Thr Asn His His Pro Pro Gln Phe Gln Glu Asp Glu
65                  70                  75                  80

Asn Met Val Phe Pro Leu Pro Pro Ser Ser Leu Asp Asp Arg Ser Arg
                85                  90                  95

Gly Ala Arg Asp Lys Glu Glu Leu Asp Arg Ser Ile Ser Leu Ser Leu
            100                 105                 110

Ala Asp Asn Thr Lys Arg Pro His Gly Tyr Gly Trp Ser Met Asp Asn
        115                 120                 125

Asn Arg Asp Phe Pro Arg Pro Phe His Gly Gly Leu Asn Pro Ser Ser
    130                 135                 140

Phe Ile Pro Pro Tyr Glu Pro Ser Tyr Gln Tyr Arg Arg Arg Gln Arg
145                 150                 155                 160

Ile Cys Gly Gly Cys Asn Ser Asp Ile Gly Ser Gly Asn Tyr Leu Gly
                165                 170                 175

Cys Met Gly Thr Phe Phe His Pro Glu Cys Phe Arg Cys His Ser Cys
            180                 185                 190

Gly Tyr Ala Ile Thr Glu His Glu Ile Pro Thr Asn Asp Ala Gly Leu
        195                 200                 205

Ile Glu Tyr Arg Cys His Pro Phe Trp Asn Gln Lys Tyr Cys Pro Ser
    210                 215                 220

His Glu Tyr Asp Lys Thr Ala Arg Cys Cys Ser Cys Glu Arg Leu Glu
225                 230                 235                 240
```

```
Ser Trp Asp Val Arg Tyr Tyr Thr Leu Glu Asp Gly Arg Ser Leu Cys
            245                 250                 255

Leu Glu Cys Met Glu Thr Ala Ile Thr Asp Thr Gly Glu Cys Gln Pro
            260                 265                 270

Leu Tyr His Ala Ile Arg Asp Tyr Tyr Glu Gly Met Tyr Met Lys Leu
            275                 280                 285

Asp Gln Gln Ile Pro Met Leu Leu Val Gln Arg Glu Ala Leu Asn Asp
            290                 295                 300

Ala Ile Val Gly Glu Lys Asn Gly Tyr His His Met Pro Glu Thr Arg
305                 310                 315                 320

Gly Leu Cys Leu Ser Glu Glu Gln Thr Val Thr Ser Val Leu Arg Arg
            325                 330                 335

Pro Arg Leu Gly Ala His Arg Leu Val Gly Met Arg Thr Gln Pro Gln
            340                 345                 350

Arg Leu Thr Arg Lys Cys Glu Val Thr Ala Ile Leu Val Leu Tyr Gly
            355                 360                 365

Leu Pro Arg Leu Leu Thr Gly Ala Ile Leu Ala His Glu Leu Met His
        370                 375                 380

Gly Trp Leu Arg Leu Asn Gly Thr Tyr Trp Phe Arg Asn Leu Asn Pro
385                 390                 395                 400

Glu Val Glu Gly Ile Cys Gln Val Leu Ser Tyr Met Trp Leu Glu
            405                 410                 415

Ser Glu Val Leu Ser Asp Pro Ser Thr Arg Asn Leu Pro Ser Thr Ser
            420                 425                 430

Ser Val Ala Thr Ser Ser Ser Ser Phe Ser Asn Lys Lys Gly Gly
            435                 440                 445

Lys Ser Asn Val Glu Lys Lys Leu Gly Glu Phe Phe Lys His Gln Ile
450                 455                 460

Ala His Asp Ala Ser Pro Ala Tyr Gly Gly Phe Arg Ala Ala Asn
465                 470                 475                 480

Ala Ala Ala Cys Lys Tyr Gly Leu Arg Arg Thr Leu Asp His Ile Arg
            485                 490                 495

Leu Thr Gly Thr Phe Pro Leu
            500

<210> SEQ ID NO 28
<211> LENGTH: 1051
<212> TYPE: DNA
<213> ORGANISM: Arabidopsis thaliana
<220> FEATURE:
<221> NAME/KEY: promoter
<222> LOCATION: (1)..(1051)
<223> OTHER INFORMATION: transcription regulating sequence from
      Arabidopsis thaliana gene At1g68430

<400> SEQUENCE: 28
atatgttttt gatataaggg gaggccacca atttgtcaga cggaaaatgt ttcagagttg      60
ggccaaccga ggtatcttca aattcagtga tccaatttgt tttactattg agcccaaaaa     120
ttgaaggtgt tgtagttttg tcggatgtca ggatgtgtac tgagttaagt cagaagttcc     180
aaaaatatat gaaccaactt aaagtgacgt ggacataacg agaaaatgtt gtaacaatat     240
gcagtatata cttataagat tgtgataatt actaatggtg atttaaaggt atttctaatc     300
tgtgaaatat acttataagg ttgtgggatt gaatgggaga gtttaataag tttcttttt     360 tgttgcaaaa taatcagctt ttaaaatact tattacattc gaggcacatg aactattttt     420
ctatccattg gccgattcta aatataaata gatgttggat aatagagttt aaagaatttt     480
```

```
gagttttcta atatacagat tgagaggcca agtgctagat tcaatatgta acaatatcag      540
gctgatattt tcgattgaat atcaccagta ttcaataata aaatcatcaa taagactaac      600
aagtatggtc tcattctaaa cacagtaatc acgacaagaa ttctaatgag aatctatgac      660
caataaagac taacagtagg tgtcttgcat ctacgctcac attatttcat ttctttcaaa      720
aaaggagtaa aattgtaaaa accagagcta atgattcttc cttctatgca cattaaggaa      780
aaagtaaaag agaacaacat gagaaaaagc aaaggaatc  gaataaacaa acactttatc       840
tttttcaaaa tctcatcaat aatgacacaa tttggaattt cattggaaac tgtgtcctta      900
tggtccacaa aaattccaat tcaaagcaca cactttcgag acaaagactt gcttcaaaag      960
aatcaaaagg acaaagtttt ttgtgttgcc aagttttgga tccttttata atgaacctca     1020
cttgaaagca aagtttccac atttccaaat t                                    1051

<210> SEQ ID NO 29
<211> LENGTH: 1065
<212> TYPE: DNA
<213> ORGANISM: Arabidopsis thaliana
<220> FEATURE:
<221> NAME/KEY: promoter
<222> LOCATION: (1)..(1065)
<223> OTHER INFORMATION: transcription regulating sequence from
      Arabidopsis thaliana gene At1g68430

<400> SEQUENCE: 29
ataatcacta gaatatgttt ttgatataag gggaggccac caatttgtca gacggaaaat       60
gtttcagagt tgggccaacc gaggtatctt caaattcagt gatccaattt gttttactat      120
tgagcccaaa aattgaaggt gttgtagttt tgtcggatgt caggatgtgt actgagttaa      180
gtcagaagtt ccaaaaatat atgaaccaac ttaaagtgac gtggacataa cgagaaaatg      240
ttgtaacaat atgcagtata tacttataag attgtgataa ttactaatgg tgatttaaag      300
gtatttctaa tctgtgaaat atacttataa ggttgtggga ttgaatggga gagtttaata      360
agtttctttt tttgttgcaa aataatcagc ttttaaaata cttattacat tcgaggcaca      420
tgaactattt ttctatccat tggccgattc taaatataaa tagatgttgg ataatagagt      480
ttaaagaatt ttgagttttc taatatacag attgagaggc caagtgctag attcaatatg      540
taacaatatc aggctgatat tttcgattga atatcaccag tattcaataa taaaatcatc      600
aataagacta acaagtatgg tctcattcta aacacagtaa tcacgacaag aattctaatg      660
agaatctatg accaataaag actaacagta ggtgtcttgc atctacgctc acattatttc      720
atttctttca aaaaggagta aaattgtaa  aaaccagagc taatgattct tccttctatg      780
cacattaagg aaaagtaaa  agagaacaac atgagaaaaa gcaaaggaa  tcgaataaac      840 aaacacttta tcttttcaa  aatctcatca ataatgacac aatttggaat tcattggaa      900 actgtgtcct tatggtccac aaaaattcca attcaaagca cactttcg   agacaaagac      960 ttgcttcaaa agaatcaaaa ggacaaagtt ttttgtgttg ccaagttttg gatcctttta     1020
taatgaacct cacttgaaag caaagtttcc acatttccaa attct                     1065

<210> SEQ ID NO 30
<211> LENGTH: 1038
<212> TYPE: DNA
<213> ORGANISM: Arabidopsis thaliana
<220> FEATURE:
<221> NAME/KEY: promoter
<222> LOCATION: (1)..(1038)
<223> OTHER INFORMATION: transcription regulating sequence from
      Arabidopsis thaliana gene At1g68430
```

```
<400> SEQUENCE: 30
atatgttttt gatataaggg gaggccacca atttgtcaga cggaaaatgt tcagagttg      60 ggccaaccga ggtatcttca aattcagtga tccaatttgt tttactattg agcccaaaaa    120
ttgaaggtgt tgtagttttg tcggatgtca ggatgtgtac tgagttaagt cagaagttcc    180
aaaaatatat gaaccaactt aaagtgacgt ggacataacg agaaaatgtt gtaacaatat    240
gcagtatata cttataagat tgtgataatt actaatggtg atttaaggt atttctaatc     300 tgtgaaatat acttataagg ttgtgggatt gaatgggaga gtttaataag tttctttttt    360
tgttgcaaaa taatcagctt ttaaaatact tattacattc gaggcacatg aactattttt    420
ctatccattg gccgattcta aatataaata gatgttggat aatagagttt aaagaattt     480 gagttttcta atatacagat tgagaggcca agtgctagat caatatgta acaatatcag     540 gctgatattt tcgattgaat atcaccagta ttcaataata aaatcatcaa taagactaac    600
aagtatggtc tcattctaaa cacagtaatc acgacaagaa ttctaatgag aatctatgac    660
caataaagac taacagtagg tgtcttgcat ctacgctcac attatttcat ttctttcaaa    720
aaaggagtaa aattgtaaaa accagagcta atgattcttc cttctatgca cattaaggaa    780
aaagtaaaag agaacaacat gagaaaaagc aaaaggaatc gaataaacaa acactttatc    840
tttttcaaaa tctcatcaat aatgacacaa tttggaattt cattggaaac tgtgtcctta    900
tggtccacaa aaattccaat tcaaagcaca cactttcgag acaaagactt gcttcaaaag    960
aatcaaaagg acaaagtttt ttgtgttgcc aagttttgga tccttttata atgaacctca   1020
cttgaaagca agtttcc                                                  1038

<210> SEQ ID NO 31
<211> LENGTH: 1050
<212> TYPE: DNA
<213> ORGANISM: Arabidopsis thaliana
<220> FEATURE:
<221> NAME/KEY: promoter
<222> LOCATION: (1)..(1050)
<223> OTHER INFORMATION: transcription regulating sequence from
      Arabidopsis thaliana gene At1g68430

<400> SEQUENCE: 31
ataatcacta gaatatgttt ttgatataag gggaggccac caatttgtca gacggaaaat     60
gtttcagagt tgggccaacc gaggtatctt caaattcagt gatccaattt gttttactat    120
tgagcccaaa aattgaaggt gttgtagttt tgtcggatgt caggatgtgt actgagttaa    180
gtcagaagtt ccaaaaatat atgaaccaac ttaaagtgac gtggacataa cgagaaaatg    240
ttgtaacaat atgcagtata tacttataag attgtgataa ttactaatgg tgatttaaag    300
gtatttctaa tctgtgaaat atacttataa ggttgtggga ttgaatggga gagtttaata    360
agtttctttt tttgttgcaa ataatcagc ttttaaaata cttattacat tcgaggcaca    420
tgaactattt ttctatccat tggccgattc taaatataaa tagatgttgg ataatagagt    480
ttaaagaatt ttgagttttc taatatacag attgagaggc caagtgctag attcaatatg    540
taacaatatc aggctgatat tttcgattga atatcaccag tattcaataa taaaatcatc    600
aataagacta acaagtatgg tctcattcta aacacagtaa tcacgacaag aattctaatg    660
agaatctatg accaataaag actaacagta ggtgtcttgc atctacgctc acattatttc    720
atttctttca aaaaaggagt aaaattgtaa aaaccagagc taatgattct tccttctatg    780
cacattaagg aaaaagtaaa agagaacaac atgagaaaaa gcaaaaggaa tcgaataaac    840
```

```
aaacacttta tcttttttcaa aatctcatca ataatgacac aatttggaat ttcattggaa      900
actgtgtcct tatggtccac aaaaattcca attcaaagca cacactttcg agacaaagac      960
ttgcttcaaa agaatcaaaa ggacaaagtt ttttgtgttg ccaagttttg gatccttta     1020 taatgaacct cacttgaaag caaagtttcc                                      1050

<210> SEQ ID NO 32
<211> LENGTH: 2096
<212> TYPE: DNA
<213> ORGANISM: Arabidopsis thaliana
<220> FEATURE:
<221> NAME/KEY: promoter
<222> LOCATION: (1)..(2096)
<223> OTHER INFORMATION: transcription regulating sequence from
      Arabidopsis thaliana gene At1g68430

<400> SEQUENCE: 32
tttgtaggtt aacatttatt ttcttatcaa tttgtataaa aagaaaattt gactatatat       60
atatatctac aaataaatga atttgactat gatttcaaca gaaaaagaaa aagaattttc      120
gaaactgtat taaggatttt ctgtttaaat tttggcaaaa actatatatat tatttggaaa    180 atatattaga ttcgattaaa tttacaatat ggatgtgagt tttcggacat atgtgaatat     240
ttttggaaaa atagtttatt ctattcatga attattattc ataaataaac acagacaaag    300
ggaaaggtac tagaaacact cattatggac caatttgtga caatttgcaa tgtagaaaca    360
acgacatgcg aaccacacaa gtaatgccac gtgtaatctc ctgaatgaat agaagaaaga    420
aaaggcataa atagccttaa gattttctca ccagaatgac ctggcgttcg atttggtcca    480
aatcagtgaa atcaaaataa acgtttcttt ttctggttag atgcacgcca cgatttcgtc    540
taagagaagg cacaatttaa tcttactaga agaagggggct tatcaattta gttacgtttt    600
tggtttttac tcaaaaacaa cttgtatgtt ctacaagaaa cttcgaagca aatctaactt    660
gtaataatgg attgagttag atctaaaagc aatatgtatt tttaaggcta agaattttca    720
acagctatat accacaataa ttatcatttt gataatttca caaaattaaa gaaacgtgta    780
gagagaaact tattatactt ctagaaaaat gatttaactt ttaataaaaa aatttatact    840
taatatatgt atttgatatg cggtttatac aaaacaatca catgtgttta ataagaata     900 gttaatatta aaaatctaaa acaataatta ttctggaaca taaataatgc ttacataaaa    960
tttgatgtga aatggaatta gtatttattg acgttaaaaa aataaaaaat aattattgac    1020
gctaatgggt tatataatca ctagaatatg tttttgatat aaggggaggc caccaatttg    1080
tcagacggaa aatgtttcag agttgggcca accgaggtat cttcaaattc agtgatccaa    1140
tttgttttac tattgagccc aaaaattgaa ggtgttgtag ttttgtcgga tgtcaggatg    1200
tgtactgagt taagtcagaa gttccaaaaa tatatgaacc aacttaaagt gacgtggaca    1260
taacgagaaa atgttgtaac aatatgcagt atatacttat aagattgtga taattactaa    1320
tggtgattta aaggtatttc taatctgtga aatatactta aaggttgtg ggattgaatg     1380 ggagagttta ataagtttct ttttttgttg caaaataatc agcttttaaa atacttatta    1440
cattcgaggc acatgaacta ttttctatc cattggccga ttctaaatat aaatagatgt     1500
tggataatag agtttaaaga attttgagtt ttctaatata cagattgaga ggccaagtgc    1560
tagattcaat atgtaacaat atcaggctga tattttcgat tgaatatcac cagtattcaa    1620
taataaaatc atcaataaga ctaacaagta tggtctcatt ctaaacacag taatcacgac    1680
aagaattcta atgagaatct atgaccaata aagactaaca gtaggtgtct tgcatctacg    1740
```

```
ctcacattat tcatttctt tcaaaaaagg agtaaaattg taaaaaccag agctaatgat    1800
tcttccttct atgcacatta aggaaaaagt aaaagagaac aacatgagaa aaagcaaaag    1860
gaatcgaata aacaaacact ttatctttt caaaatctca tcaataatga cacaatttgg    1920
aatttcattg gaaactgtgt ccttatggtc cacaaaaatt ccaattcaaa gcacacactt    1980
tcgagacaaa gacttgcttc aaaagaatca aaggacaaa gttttttgtg ttgccaagtt    2040
ttggatcctt ttataatgaa cctcacttga agcaaagtt tccacatttc caaatt    2096
```

<210> SEQ ID NO 33
<211> LENGTH: 2110
<212> TYPE: DNA
<213> ORGANISM: Arabidopsis thaliana
<220> FEATURE:
<221> NAME/KEY: promoter
<222> LOCATION: (1)..(2110)
<223> OTHER INFORMATION: transcription regulating sequence from
      Arabidopsis thaliana gene At1g68430

<400> SEQUENCE: 33

```
taatacatta attttgtagg ttaacattta ttttcttatc aatttgtata aaagaaaat     60 ttgactatat atatatatct acaaataaat gaatttgact atgatttcaa cagaaaaga    120 aaagaattc tcgaaactgt attaaggatt ttctgtttaa attttggcaa aaactaatat   180
attatttgga aaatatatta gattcgatta aatttacaat atggatgtga gttttcggac   240
atatatgaat attttggaa aaatagttta ttctattcat gaattattat tcataaataa    300
acacagacaa agggaaaggt actagaaaca ctcattatgg accaatttgt gacaatttgc    360
aatgtagaaa caacgacatg cgaaccacac aagtaatgcc acgtgtaatc tcctgaatga    420
atagaagaaa gaaaaggcat aaatagcctt aagattttct caccagaatg acctggcgtt    480
cgatttggtc caaatcagtg aaatcaaat aaacgtttct ttttctggtt agatgcacgc    540
cacgatttcg tctaagagaa ggcacaattt aatcttacta gaagaagggg cttatcaatt    600
tagttacgtt tttggtttt actcaaaaac aacttgtatg ttctacaaga aacttcgaag    660
caaatctaac ttgtaataat ggattgagtt agatctaaaa gcaatatgta ttttaaggc    720 taagaattt caacagctat ataccacaat aattatcatt ttgataattt cacaaaatta    780
aagaaacgtg tagagagaaa cttattatac ttctagaaaa atgatttaac ttttaataaa    840
aaaatttata cttaatatat gtatttgata tgcggtttat acaaaacaat cacatgtgtt    900
taaataagaa tagttaatat taaaaatcta aaacaataat tattctggaa cataaataat    960
gcttacataa aatttgatgt gaaatggaat tagtatttat tgacgttaaa aaaataaaaa   1020
ataattattg acgctaatgg gttatataat cactagaata tgttttgat ataagggag    1080 gccaccaatt tgtcagacgg aaaatgtttc agagttgggc caaccgaggt atcttcaaat   1140
tcagtgatcc aatttgtttt actattgagc ccaaaaattg aaggtgttgt agttttgtcg   1200
gatgtcagga tgtgtactga gttaagtcag aagttccaaa aatatatgaa ccaacttaaa   1260
gtgacgtgga cataacgaga aaatgttgta acaatatgca gtatatactt ataagattgt   1320
gataattact aatggtgatt taaggtatt tctaatctgt gaaatatact tataaggttg    1380
tgggattgaa tgggagagtt taataagttt cttttttgt tgcaaaataa tcagctttta    1440
aaatacttat tacattcgag gcacatgaac tatttttcta tccattggcc gattctaaat   1500
ataaatagat gttggataat agagtttaaa gaattttgag ttttctaata tacagattga   1560
gaggccaagt gctagattca atatgtaaca atatcaggct gatatttcg attgaatatc    1620
```

```
accagtattc aataataaaa tcatcaataa gactaacaag tatggtctca ttctaaacac    1680
agtaatcacg acaagaattc taatgagaat ctatgaccaa taaagactaa cagtaggtgt    1740
cttgcatcta cgctcacatt atttcatttc tttcaaaaaa ggagtaaaat tgtaaaaacc    1800
agagctaatg attcttcctt ctatgcacat taaggaaaaa gtaaaagaga acaacatgag    1860
aaaaagcaaa aggaatcgaa taaacaaaca ctttatcttt ttcaaaatct catcaataat    1920
gacacaattt ggaatttcat tggaaactgt gtccttatgg tccacaaaaa ttccaattca    1980
aagcacacac tttcgagaca aagacttgct tcaaaagaat caaaaggaca aagttttttg    2040
tgttgccaag ttttggatcc ttttataatg aacctcactt gaaagcaaag tttccacatt    2100
tccaaattct                                                          2110
```

<210> SEQ ID NO 34
<211> LENGTH: 2083
<212> TYPE: DNA
<213> ORGANISM: Arabidopsis thaliana
<220> FEATURE:
<221> NAME/KEY: promoter
<222> LOCATION: (1)..(2083)
<223> OTHER INFORMATION: transcription regulating sequence from
      Arabidopsis thaliana gene At1g68430

<400> SEQUENCE: 34

```
tttgtaggtt aacatttatt ttcttatcaa tttgtataaa agaaaatttt gactatatat      60
atatatctac aaataaatga atttgactat gatttcaaca gaaaaagaaa aagaattttc     120
gaaactgtat taaggatttt ctgtttaaat tttggcaaaa actaatatat tatttggaaa     180
atatattaga ttcgattaaa tttacaatat ggatgtgagt tttcggacat atatgaatat     240
ttttggaaaa atagttttatt ctattcatga attattattc ataaataaac acagacaaag    300
ggaaaggtac tagaaacact cattatggac caatttgtga caatttgcaa tgtagaaaca    360 acgcatgcg aaccacacaa gtaatgccac gtgtaatctc ctgaatgaat agaagaaga     420 aaaggcataa atagccttaa gattttctca ccagaatgac ctggcgttcg atttggtcca    480
aatcagtgaa atcaaaataa acgtttcttt ttctggttag atgcacgcca cgatttcgtc    540
taagagaagg cacaatttaa tcttactaga agaaggggct tatcaattta gttacgtttt    600
tggtttttac tcaaaacaa cttgtatgtt ctacaagaaa cttcgaagca aatctaactt    660
gtaataatgg attgagttag atctaaaagc aatatgtatt tttaaggcta agaattttca    720
acagctatat accacaataa ttatcatttt gataatttca caaattaaa gaaacgtgta    780 gagagaaact tattatactt ctagaaaaat gatttaactt ttaataaaaa aatttatact    840
taatatatgt atttgatatg cggttttatac aaaacaatca catgtgttta ataagaata    900 gttaatatta aaaatctaaa acaataatta ttctggaaca taaataatgc ttacataaaa    960
tttgatgtga aatggaatta gtatttattg acgttaaaaa aataaaaaat aattattgac   1020
gctaatgggt tatataatca ctagaatatg ttttttgatat aaggggaggc caccaatttg   1080
tcagacggaa aatgtttcag agttgggcca accgaggtat cttcaaattc agtgatccaa   1140
tttgttttac tattgagccc aaaaattgaa ggtgttgtag ttttgtcgga tgtcaggatg   1200
tgtactgagt taagtcagaa gttccaaaaa tatatgaacc aacttaaagt gacgtggaca   1260
taacgagaaa atgttgtaac aatatgcagt atatacttat aagattgtga taattactaa   1320
tggtgattta aaggtatttc taatctgtga aatatactta aaggttgtg ggattgaatg   1380 ggagagttta ataagtttct tttttttgttg caaaataatc agcttttaaa atacttatta   1440
```

```
cattcgaggc acatgaacta tttttctatc cattggccga ttctaaatat aaatagatgt      1500
tggataatag agtttaaaga attttgagtt ttctaatata cagattgaga ggccaagtgc      1560
tagattcaat atgtaacaat atcaggctga tattttcgat tgaatatcac cagtattcaa      1620
taataaaatc atcaataaga ctaacaagta tggtctcatt ctaaacacag taatcacgac      1680
aagaattcta atgagaatct atgaccaata aagactaaca gtaggtgtct tgcatctacg      1740
ctcacattat ttcatttctt tcaaaaaagg agtaaaattg taaaaccag agctaatgat       1800 tcttccttct atgcacatta aggaaaaagt aaaagagaac aacatgagaa aaagcaaaag      1860
gaatcgaata aacaaacact ttatcttttt caaaatctca tcaataatga cacaatttgg      1920
aatttcattg gaaactgtgt ccttatggtc cacaaaaatt ccaattcaaa gcacacactt      1980
tcgagacaaa gacttgcttc aaaagaatca aaggacaaa gttttttgtg ttgccaagtt      2040
ttggatcctt ttataatgaa cctcacttga aagcaaagtt tcc                        2083
```

<210> SEQ ID NO 35
<211> LENGTH: 2095
<212> TYPE: DNA
<213> ORGANISM: Arabidopsis thaliana
<220> FEATURE:
<221> NAME/KEY: promoter
<222> LOCATION: (1)..(2095)
<223> OTHER INFORMATION: transcription regulating sequence from
      Arabidopsis thaliana gene At1g68430

<400> SEQUENCE: 35

```
taatacatta attttgtagg ttaacattta ttttcttatc aatttgtata aaagaaaat         60 ttgactatat atatatatct acaaataaat gaatttgact atgatttcaa cagaaaaga       120 aaaagaattt tcgaaactgt attaaggatt ttctgtttaa attttggcaa aaactaatat      180
attatttgga aaatatatta gattcgatta aatttacaat atggatgtga gttttcggac      240
atatatgaat attttggaa aaatagttta ttctattcat gaattattat tcataaataa       300
acacagacaa agggaaaggt actagaaaca ctcattatgg accaatttgt gacaatttgc      360
aatgtagaaa caacgacatg cgaaccacac aagtaatgcc acgtgtaatc tcctgaatga      420
atagaagaaa gaaaaggcat aaatagcctt aagattttct caccagaatg acctggcgtt      480
cgatttggtc caaatcagtg aaatcaaaat aaacgtttct ttttctggtt agatgcacgc      540
cacgatttcg tctaagagaa ggcacaattt aatcttacta gaagaagggg cttatcaatt      600
tagttacgtt tttggttttt actcaaaaac aacttgtatg ttctacaaga aacttcgaag      660
caaatctaac ttgtaataat ggattgagtt agatctaaaa gcaatatgta ttttaaggc       720 taagaatttt caacagctat ataccacaat aattatcatt ttgataattt cacaaaatta      780
aagaaacgtg tagagagaaa cttattatac ttctagaaaa atgatttaac ttttaataaa      840
aaaatttata cttaatatat gtatttgata tgcggtttat acaaaacaat cacatgtgtt      900
taaataagaa tagttaatat taaaaatcta aaacaataat tattctggaa cataaataat      960
gcttacataa aatttgatgt gaaatggaat tagtatttat tgacgttaaa aaaataaaaa     1020
ataattattg acgctaatgg gttatataat cactagaata tgttttttgat ataagggag     1080 gccaccaatt tgtcagacgg aaaatgtttc agagttgggc caaccgaggt atcttcaaat     1140
tcagtgatcc aatttgtttt actattgagc ccaaaaattg aaggtgttgt agttttgtcg     1200
gatgtcagga tgtgtactga gttaagtcag aagttccaaa aatatatgaa ccaacttaaa     1260
gtgacgtgga cataacgaga aaatgttgta acaatatgca gtatatactt ataagattgt     1320
```

-continued

```
gataattact aatggtgatt taaaggtatt tctaatctgt gaaatatact tataaggttg    1380
tgggattgaa tgggagagtt taataagttt cttttttgt tgcaaaataa tcagcttta      1440 aaatacttat tacattcgag gcacatgaac tatttttcta tccattggcc gattctaaat    1500
ataaatagat gttggataat agagtttaaa gaattttgag ttttctaata tacagattga    1560
gaggccaagt gctagattca atatgtaaca atatcaggct gatattttcg attgaatatc    1620
accagtattc aataataaaa tcatcaataa gactaacaag tatggtctca ttctaaacac    1680
agtaatcacg acaagaattc taatgagaat ctatgaccaa taagactaa cagtaggtgt     1740 cttgcatcta cgctcacatt atttcatttc tttcaaaaaa ggagtaaaat tgtaaaaacc    1800
agagctaatg attcttcctt ctatgcacat taaggaaaaa gtaaaagaga caacatgag     1860 aaaaagcaaa aggaatcgaa taaacaaaca ctttatcttt ttcaaaatct catcaataat    1920
gacacaattt ggaatttcat tggaaactgt gtccttatgg tccacaaaaa ttccaattca    1980
aagcacacac tttcgagaca aagacttgct tcaaaagaat caaaaggaca aagtttttg     2040 tgttgccaag ttttggatcc ttttataatg aacctcactt gaaagcaaag tttcc         2095
```

<210> SEQ ID NO 36
<211> LENGTH: 540
<212> TYPE: DNA
<213> ORGANISM: Arabidopsis thaliana
<220> FEATURE:
<221> NAME/KEY: CDS
<222> LOCATION: (16)..(456)
<223> OTHER INFORMATION: encoding expressed protein

<400> SEQUENCE: 36

```
acatttccaa attct atg gct aca ctg cag aga ttc aag ttc ttg ggg acg     51
               Met Ala Thr Leu Gln Arg Phe Lys Phe Leu Gly Thr
                 1               5                  10 cag tgc gga gta gca gca caa agc ccg aca cga agt ccg agt ccg agg       99
Gln Cys Gly Val Ala Ala Gln Ser Pro Thr Arg Ser Pro Ser Pro Arg
         15                  20                  25 aca agt cca ttg gta cag ctt cga cga aag aag aca act tta aag atg     147
Thr Ser Pro Leu Val Gln Leu Arg Arg Lys Lys Thr Thr Leu Lys Met
 30                  35                  40 ctt ttg agt ctt gca tct ccg agt cgc cga gag cag caa ccg ttg att     195
Leu Leu Ser Leu Ala Ser Pro Ser Arg Arg Glu Gln Gln Pro Leu Ile
45                  50                  55                  60 cat cat cat cac aag gac gta gcc gga cgg aaa ctt aaa gac tta ttc     243
His His His His Lys Asp Val Ala Gly Arg Lys Leu Lys Asp Leu Phe
                 65                  70                  75 gtc tct tcg tct tcc gca gag gaa gaa caa gaa gag gac gag aga cca     291
Val Ser Ser Ser Ser Ala Glu Glu Glu Gln Glu Glu Asp Glu Arg Pro
         80                  85                  90 aag ggg aaa aca aaa gaa gaa gtt ctt gca gcc atg gcg gct aaa ctg     339
Lys Gly Lys Thr Lys Glu Glu Val Leu Ala Ala Met Ala Ala Lys Leu
 95                 100                 105 aat gca gct tca aga tta caa tgt gag tct gct gat gca gca cca gtt     387
Asn Ala Ala Ser Arg Leu Gln Cys Glu Ser Ala Asp Ala Ala Pro Val
110                 115                 120 tgg ttc gga ttc agc aaa cgg ctt ctt cag cga gct tgg cgt cct aaa     435
Trp Phe Gly Phe Ser Lys Arg Leu Leu Gln Arg Ala Trp Arg Pro Lys
125                 130                 135                 140 ctt ggt acc att cac gag taa tgtaacccaa ttttcttctc tttttttggt        486
Leu Gly Thr Ile His Glu
                145 gtgactttgg aaaccattag tttcccatat gaatgaatat atatgtttct tctc          540
```

<210> SEQ ID NO 37
<211> LENGTH: 146
<212> TYPE: PRT
<213> ORGANISM: Arabidopsis thaliana

<400> SEQUENCE: 37

```
Met Ala Thr Leu Gln Arg Phe Lys Phe Leu Gly Thr Gln Cys Gly Val
1               5                   10                  15

Ala Ala Gln Ser Pro Thr Arg Ser Pro Ser Pro Arg Thr Ser Pro Leu
            20                  25                  30

Val Gln Leu Arg Arg Lys Lys Thr Thr Leu Lys Met Leu Leu Ser Leu
        35                  40                  45

Ala Ser Pro Ser Arg Arg Glu Gln Gln Pro Leu Ile His His His His
    50                  55                  60

Lys Asp Val Ala Gly Arg Lys Leu Lys Asp Leu Phe Val Ser Ser Ser
65                  70                  75                  80

Ser Ala Glu Glu Glu Gln Glu Glu Asp Glu Arg Pro Lys Gly Lys Thr
                85                  90                  95

Lys Glu Glu Val Leu Ala Ala Met Ala Ala Lys Leu Asn Ala Ala Ser
            100                 105                 110

Arg Leu Gln Cys Glu Ser Ala Asp Ala Ala Pro Val Trp Phe Gly Phe
        115                 120                 125

Ser Lys Arg Leu Leu Gln Arg Ala Trp Arg Pro Lys Leu Gly Thr Ile
    130                 135                 140

His Glu
145
```

<210> SEQ ID NO 38
<211> LENGTH: 1030
<212> TYPE: DNA
<213> ORGANISM: Arabidopsis thaliana
<220> FEATURE:
<221> NAME/KEY: promoter
<222> LOCATION: (1)..(1030)
<223> OTHER INFORMATION: transcription regulating sequence from
      Arabidopsis thaliana gene At5g67280

<400> SEQUENCE: 38

```
ttactacgta gtacatgtta aactacatat ataaggattc cataaatatg aatcaaatcg      60
aattcttctt atataactaa gacattaaat gtctacttgc acttcattaa aaagaatctt     120
ctgattttat ttttggtata tgcaaaatta taactgcatt taaaacagag attagatcat     180
gaaacgaata ttatttctga aaaagtaggt atatctagta atgttaattt attttttgct     240
aaggatatct agtaatattt tatatgaaac acttgttttt atttatgtgt tttgcgcata     300
aagtcaatat tataacgaat cactagatta gtttttatttt tatcttatag attagtttaa     360
taagcctata tctataagat gtactatgat cagagaaaca ttaggtgtaa tgagaaaaca     420
ataataaaac ggtcatatat aagtaaatcc aagtcagtga gagacctgca aaaatttcga     480 acttttgtg aatgtcttat agcaaagata ctattctccc atctgatcat gtttccatag     540
atattagtta attggctaat aatacaattc ttcacacaca tcacatgatc gatatgcgta     600
atctcacgtc acaatttccg tcataatcaa aaggagtaac agaattagta tattatatag     660
tttctgtgat ctagcaaaga tttaaatgta aacaaaacta tccagattta tatggtttg      720 ttacgtttct ttgaagatca atgtaaacaa tgatgaacca atattagggt ccacgttgaa     780
tataaacgtg aaaaacgaca aagcgacgtc agcataattt acgaatagga aaacagtgtt     840
aacttttgtt atcacattcc gtgcaattta cataggatat agaattttt atttacaaaa      900
```

```
gttatatttta taaagaatta ctcaaatcaa gaattccata aaaagataaa cactttcata        960
tatcgttcac aatcacatgg cctttcaaa aaatcaatct tttagttctc tatcgatgcg         1020
taggcttgaa                                                                1030
```

<210> SEQ ID NO 39
<211> LENGTH: 1044
<212> TYPE: DNA
<213> ORGANISM: Arabidopsis thaliana
<220> FEATURE:
<221> NAME/KEY: promoter
<222> LOCATION: (1)..(1044)
<223> OTHER INFORMATION: transcription regulating sequence from
    Arabidopsis thaliana gene At5g67280

<400> SEQUENCE: 39

```
ccattgggat tattactacg tagtacatgt taaactacat ataaaggat tccataaata          60 tgaatcaaat cgaattcttc ttatataact aagacattaa atgtctactt gcacttcatt       120
aaaaagaatc ttctgatttt attttggta tatgcaaaat tataactgca tttaaaacag         180
agattagatc atgaaacgaa tattatttct gaaaaagtag gtatatctag taatgttaat        240
ttattttttg ctaaggatat ctagtaatat tttatatgaa acacttgttt ttatttatgt       300
gttttgcgca taaagtcaat attataacga atcactagat tagttttatt tttatcttat       360
agattagttt aataagccta tatctataag atgtactatg atcagagaaa cattaggtgt       420
aatgagaaaa caataataaa acggtcatat ataagtaaat ccaagtcagt gagagacctg       480
caaaaatttc gaactttttg tgaatgtctt atagcaaaga tactattctc ccatctgatc       540
atgtttccat agatattagt taattggcta ataatacaat tcttcacaca catcacatga       600
tcgatatgcg taatctcacg tcacaatttc cgtcataatc aaaaggagta acagaattag       660
tatattatat agtttctgtg atctagcaaa gatttaaatg taaacaaaac tatccagatt       720
tatatggttt tgttacgttt ctttgaagat caatgtaaac aatgatgaac caatattagg       780
gtccacgttg aatataaacg tgaaaaacga caaagcgacg tcagcataat ttacgaatag       840
gaaaacagtg ttaactttg ttatcacatt ccgtgcaatt tacataggat atagaatttt        900
ttatttacaa aagttatatt tataaagaat tactcaaatc aagaattcca taaaagata        960 aacactttca tatcgttc acaatcacat ggcctttca aaaaatcaat cttttagttc         1020
tctatcgatg cgtaggcttg aagc                                                1044
```

<210> SEQ ID NO 40
<211> LENGTH: 968
<212> TYPE: DNA
<213> ORGANISM: Arabidopsis thaliana
<220> FEATURE:
<221> NAME/KEY: promoter
<222> LOCATION: (1)..(968)
<223> OTHER INFORMATION: transcription regulating sequence from
    Arabidopsis thaliana gene At5g67280

<400> SEQUENCE: 40

```
ttactacgta gtacatgtta aactacatat ataaggattc cataaatatg aatcaaatcg        60
aattcttctt atataactaa gacattaaat gtctacttgc acttcattaa aaagaatctt       120
ctgattttat tttggtata tgcaaaatta taactgcatt taaaacagag attagatcat        180
gaaacgaata ttatttctga aaaagtaggt atatctagta atgttaattt attttttgct       240
aaggatatct agtaatattt tatatgaaac acttgttttt atttatgtgt ttgcgcata        300 aagtcaatat tataacgaat cactagatta gttttatttt tatcttatag attagttaa        360
```

```
taagcctata tctataagat gtactatgat cagagaaaca ttaggtgtaa tgagaaaaca      420
ataataaaac ggtcatatat aagtaaatcc aagtcagtga gagacctgca aaaatttcga      480 acttttttgtg aatgtcttat agcaaagata ctattctccc atctgatcat gtttccatag    540
atattagtta attggctaat aatacaattc ttcacacaca tcacatgatc gatatgcgta     600
atctcacgtc acaatttccg tcataatcaa aaggagtaac agaattagta tattatatag    660
tttctgtgat ctagcaaaga tttaaatgta aacaaaacta tccagattta tatggttttg    720
ttacgtttct ttgaagatca atgtaaacaa tgatgaacca atattagggt ccacgttgaa    780
tataaacgtg aaaaacgaca aagcgacgtc agcataattt acgaatagga aaacagtgtt    840
aacttttgtt atcacattcc gtgcaattta cataggatat agaattttt atttacaaaa     900 gttatattta taaagaatta ctcaaatcaa gaattccata aaaagataaa cactttcata   960
tatcgttc                                                              968
```

```
<210> SEQ ID NO 41
<211> LENGTH: 980
<212> TYPE: DNA
<213> ORGANISM: Arabidopsis thaliana
<220> FEATURE:
<221> NAME/KEY: promoter
<222> LOCATION: (1)..(980)
<223> OTHER INFORMATION: transcription regulating sequence from
      Arabidopsis thaliana gene At5g67280

<400> SEQUENCE: 41
```

```
ccattgggat tattactacg tagtacatgt taaactacat atataaggat tccataaata     60
tgaatcaaat cgaattcttc ttatataact aagacattaa atgtctactt gcacttcatt    120
aaaaagaatc ttctgatttt attttggta tatgcaaaat tataactgca tttaaaacag     180
agattagatc atgaaacgaa tattatttct gaaaagtag gtatatctag taatgttaat    240 ttatttttg ctaaggatat ctagtaatat tttatatgaa acacttgttt ttatttatgt     300
gttttgcgca taaagtcaat attataacga atcactagat tagtttttatt tttatcttat  360 agattagttt aataagccta tatctataag atgtactatg atcagagaaa cattaggtgt    420
aatgagaaaa caataataaa acggtcatat ataagtaaat ccaagtcagt gagagacctg   480
caaaaatttc gaacttttttg tgaatgtctt atagcaaaga tactattctc ccatctgatc  540
atgtttccat agatattagt taattggcta ataatacaat tcttcacaca catcacatga   600
tcgatatgcg taatctcacg tcacaatttc cgtcataatc aaaaggagta acagaattag   660
tatattatat agtttctgtg atctagcaaa gatttaaatg taaacaaaac tatccagatt   720
tatatggttt tgttacgttt ctttgaagat caatgtaaac aatgatgaac caatattagg   780
gtccacgttg aatataaacg tgaaaaacga caaagcgacg tcagcataat ttacgaatag   840
gaaaacagtg ttaacttttg ttatcacatt ccgtgcaatt tacataggat atagaattttt  900 ttatttacaa aagttatatt tataaagaat tactcaaatc aagaattcca taaaagata   960 aacactttca tatatcgttc                                                980
```

```
<210> SEQ ID NO 42
<211> LENGTH: 2022
<212> TYPE: DNA
<213> ORGANISM: Arabidopsis thaliana
<220> FEATURE:
<221> NAME/KEY: promoter
<222> LOCATION: (1)..(2022)
<223> OTHER INFORMATION: transcription regulating sequence from
      Arabidopsis thaliana gene At5g67280
```

<400> SEQUENCE: 42

```
aaaaacaccc gaccgatcaa gtgacaatgc gcagtgttgt attattatat tatcactgtt        60
tgaaaaattg tcgaactcag gattggttta aactttgca agacgataat aactttggag        120
ttttgcataa tggtaagtag aaaacgccat ttttcatgca tctcccgtct ttgtccaccg       180
ccaaactagt agccatcctc taattaataa tgtattacta cagctttgta tatattcgta       240
ttggagttta cagactaatc acatagtggt tacgttaggg aagataaaac atacagaaat      300
ggtaaatagc ttgtgaacct gaatctcgaa acttaccttg tccaatttgt aacatgaatg      360
tcgactataa gtaaatttgc tctgacaatt tacagtcaaa ctcaactatg agtctataat     420
atcactgtag tgggtattgt tcacacacaa cgattaatac tgtaattaat gctgaaactt     480
ggactacacg acactcatat gttttattgt ttcacacaca gcagaagaaa taattggatt     540
ttttttcggt ccagtgattg cactggtttg cagaaaaatt cttaaacgat aaataaacca     600
tgttcatctc atgattactt aatcgtttga gaaaccgtga catatggtgg taacaaacaa     660
aaacaaacaa ataccaaccg gtaaaacata tatacagtat tttatacata aacaattttg     720
tgattttggc aatcaaataa caaggaccac aatgacgctc gcgaaattta attaaaacgg     780
ggaccaattt taatcaattt gacccggtgt acattaatct tgacatgcat ttatttacgt     840
gtgatgttga cctcttggta gatacagtac tacatttata tattttttgat gcaacacata     900
actgtttagt gttttttgata tttcctttt ttatcagtct aactctcgtg agtcgtgagt     960
cgtgagttgt gagtcgtgat ccattgggat tattactacg tagtacatgt taaactacat    1020
atataaggat tccataaata tgaatcaaat cgaattcttc ttatataact aagacattaa    1080
atgtctactt gcacttcatt aaaaagaatc ttctgatttt atttttggta tatgcaaaat    1140
tataactgca tttaaaacag agattagatc atgaaacgaa tattatttct gaaaaagtag    1200
gtatatctag taatgttaat ttattttttg ctaaggatat ctagtaatat tttatatgaa    1260
acacttgttt ttatttatgt gttttgcgca taaagtcaat attataacga atcactagat    1320
tagttttatt tttatcttat agattagttt aataagccta tatctataag atgtactatg    1380
atcagagaaa cattaggtgt aatgagaaaa caataataaa acggtcatat ataagtaaat    1440
ccaagtcagt gagagacctg caaaaatttc gaactttttg tgaatgtctt atagcaaaga    1500
tactattctc ccatctgatc atgtttccat agatattagt taattggcta ataatacaat    1560
tcttcacaca catcacatga tcgatatgcg taatctcacg tcacaatttc cgtcataatc    1620
aaaaggagta acagaattag tatattatat agtttctgtg atctagcaaa gatttaaatg    1680
taaacaaaac tatccagatt tatatggttt tgttacgttt ctttgaagat caatgtaaac    1740
aatgatgaac caatattagg gtccacgttg aatataaacg tgaaaaacga caaagcgacg    1800
tcagcataat ttacgaatag gaaaacagtg ttaacttttg ttatcacatt ccgtgcaatt    1860
tacataggat atagaatttt ttatttacaa aagttatatt tataaagaat tactcaaatc    1920
aagaattcca taaaaagata aacactttca tatatcgttc acaatcacat ggccttttca    1980
aaaaatcaat cttttagttc tctatcgatg cgtaggcttg aa                        2022
```

<210> SEQ ID NO 43
<211> LENGTH: 2036
<212> TYPE: DNA
<213> ORGANISM: Arabidopsis thaliana

```
<220> FEATURE:
<221> NAME/KEY: promoter
<222> LOCATION: (1)..(2036)
<223> OTHER INFORMATION: transcription regulating sequence from
      Arabidopsis thaliana gene At5g67280

<400> SEQUENCE: 43
```

| | | | | |
|---|---|---|---|---|
| tataatatat | ccaaaaacac | ccgaccgatc | aagtgacaat | gcgcagtgtt | gtattattat | 60 |
| attatcactg | tttgaaaaat | tgtcgaactc | aggattggtt | tataactttg | caagacgata | 120 |
| ataactttgg | agttttgcat | aatggtaagt | agaaaacgcc | attttcatg | catctcccgt | 180 |
| ctttgtccac | cgccaaacta | gtagccatcc | tctaattaat | aatgtattac | tacagctttg | 240 |
| tatatattcg | tattggagtt | tacagactaa | tcacatagtg | gttacgttta | ggaagataaa | 300 |
| acatacagaa | atggtaaata | gcttgtgaac | ctgaatctcg | aaacttacct | tgtccaattt | 360 |
| gtaacatgaa | tgtcgactat | aagtaaattt | gctctgacaa | tttacagtca | aactcaacta | 420 |
| tgagtctata | atatcactgt | agtgggtatt | gttcacacac | aacgattaat | actgtaatta | 480 |
| atgctgaaac | ttggactaca | cgacactcat | atgttttatt | gtttcacaca | cagcagaaga | 540 |
| aataattgga | tttttttcg | gtccagtgat | tgcactggtt | tgcagaaaaa | ttcttaaacg | 600 |
| ataaataaac | catgttcatc | tcatgattac | ttaatcgttt | gagaaaccgt | gacatatggt | 660 |
| ggtaacaaac | aaaaacaaac | aaataccaac | cggtaaaaca | tatatacagt | attttataca | 720 |
| taaacaattt | tgtgattttg | gcaatcaaat | aacaaggacc | acaatgacgc | tcgcgaaatt | 780 |
| taattaaaac | ggggaccaat | tttaatcaat | ttgacccggt | gtacattaat | cttgacatgc | 840 |
| atttatttac | gtgtgatgtt | gacctcttgg | tagatacagt | actacattta | tatattttg | 900 |
| atgcaacaca | taactgttta | gtgtttttga | tatttccttt | ttttatcagt | ctaactctcg | 960 |
| tgagtcgtga | gtcgtgagtt | gtgagtcgtg | atccattggg | attattacta | cgtagtacat | 1020 |
| gttaaactac | atatataagg | attccataaa | tatgaatcaa | atcgaattct | tcttatataa | 1080 |
| ctaagacatt | aaatgtctac | ttgcacttca | ttaaaaagaa | tcttctgatt | ttattttgg | 1140 |
| tatatgcaaa | attataactg | catttaaaac | agagattaga | tcatgaaacg | aatattattt | 1200 |
| ctgaaaaagt | aggtatatct | agtaatgtta | atttattttt | tgctaaggat | atctagtaat | 1260 |
| attttatatg | aaacacttgt | ttttatttat | gtgttttgcg | cataaagtca | atattataac | 1320 |
| gaatcactag | attagtttta | tttttatctt | atagattagt | ttaataagcc | tatatctata | 1380 |
| agatgtacta | tgatcagaga | aacattaggt | gtaatgagaa | aacaataata | aaacggtcat | 1440 |
| atataagtaa | atccaagtca | gtgagagacc | tgcaaaaatt | tcgaactttt | tgtgaatgtc | 1500 |
| ttatagcaaa | gatactattc | tcccatctga | tcatgtttcc | atagatatta | gttaattggc | 1560 |
| taataataca | attcttcaca | cacatcacat | gatcgatatg | cgtaatctca | cgtcacaatt | 1620 |
| tccgtcataa | tcaaaaggag | taacagaatt | agtatattat | atagtttctg | tgatctagca | 1680 |
| aagatttaaa | tgtaaacaaa | actatccaga | tttatatggt | tttgttacgt | ttctttgaag | 1740 |
| atcaatgtaa | acaatgatga | accaatatta | gggtccacgt | tgaatataaa | cgtgaaaaac | 1800 |
| gacaaagcga | cgtcagcata | atttacgaat | aggaaaacag | tgttaacttt | tgttatcaca | 1860 |
| ttccgtgcaa | tttacatagg | atatagaatt | ttttatttac | aaaagttata | tttataaaga | 1920 |
| attactcaaa | tcaagaattc | cataaaaaga | taaaacttt | catatatcgt | tcacaatcac | 1980 |
| atggccttt | caaaaaatca | atcttttagt | tctctatcga | tgcgtaggct | tgaagc | 2036 |

```
<210> SEQ ID NO 44
<211> LENGTH: 1960
<212> TYPE: DNA
<213> ORGANISM: Arabidopsis thaliana
<220> FEATURE:
<221> NAME/KEY: promoter
<222> LOCATION: (1)..(1960)
<223> OTHER INFORMATION: transcription regulating sequence from
      Arabidopsis thaliana gene At5g67280

<400> SEQUENCE: 44
aaaaacaccc gaccgatcaa gtgacaatgc gcagtgttgt attattatat tatcactgtt      60
tgaaaaattg tcgaactcag gattggttta aactttgca agacgataat aactttggag      120
ttttgcataa tggtaagtag aaaacgccat ttttcatgca tctcccgtct tgtccaccg      180 ccaaactagt agccatcctc taattaataa tgtattacta cagctttgta tatattcgta     240
ttggagttta cagactaatc acatagtggt tacgtttagg aagataaaac atacagaaat     300
ggtaaatagc ttgtgaacct gaatctcgaa acttaccttg tccaatttgt aacatgaatg     360
tcgactataa gtaaatttgc tctgacaatt tacagtcaaa ctcaactatg agtctataat     420
atcactgtag tgggtattgt tcacacacaa cgattaatac tgtaattaat gctgaaactt     480
ggactacacg acactcatat gtttttattgt ttcacacaca gcagaagaaa taattggatt    540
ttttttcggt ccagtgattg cactggtttg cagaaaaatt cttaaacgat aaataaacca    600
tgttcatctc atgattactt aatcgtttga gaaaccgtga catatggtgg taacaaacaa    660
aaacaaacaa ataccaaccg gtaaaacata tatacagtat tttatacata aacaattttg    720
tgattttggc aatcaaataa caaggaccac aatgacgctc gcgaaattta attaaaacgg    780
ggaccaattt taatcaattt gacccggtgt acattaatct tgacatgcat ttatttacgt    840
gtgatgttga cctcttggta gatacagtac tacatttata tattttttgat gcaacacata   900 actgtttagt gttttttgata tttccttttt ttatcagtct aactctcgtg agtcgtgagt   960
cgtgagttgt gagtcgtgat ccattgggat tattactacg tagtacatgt taaactacat    1020
atataaggat tccataaata tgaatcaaat cgaattcttc ttatataact aagacattaa   1080
atgtctactt gcacttcatt aaaaagaatc ttctgatttt atttttggta tatgcaaaat   1140
tataactgca tttaaaacag agattagatc atgaaacgaa tattatttct gaaaaagtag   1200
gtatatctag taatgttaat ttattttttg ctaaggatat ctagtaatat tttatatgaa   1260
acacttgttt ttatttatgt gttttgcgca taaagtcaat attataacga atcactagat   1320 tagtttatt tttatcttat agattagttt aataagccta tatctataag atgtactatg    1380
atcagagaaa cattaggtgt aatgagaaaa caataataaa acggtcatat ataagtaaat   1440
ccaagtcagt gagagacctg caaaaatttc gaacttttttg tgaatgtctt atagcaaaga   1500
tactattctc ccatctgatc atgttttccat agatatagt taattggcta ataatacaat    1560
tcttcacaca catcacatga tcgatatgcg taatctcacg tcacaattc cgtcataatc   1620 aaaaggagta acagaattag tatattatat agtttctgtg atctagcaaa gatttaaatg   1680
taaacaaaac tatccagatt tatatggttt tgttacgttt ctttgaagat caatgtaaac   1740
aatgatgaac caatattagg gtccacgttg aatataaacg tgaaaaacga caaagcgacg   1800
tcagcataat ttacgaatag gaaaacagtg ttaactttttg ttatcacatt ccgtgcaatt   1860
tacataggat atagaatttt ttatttacaa aagttatatt tataaagaat tactcaaatc   1920
aagaattcca taaaaagata aacactttca tatatcgttc                         1960
```

```
<210> SEQ ID NO 45
<211> LENGTH: 1972
<212> TYPE: DNA
<213> ORGANISM: Arabidopsis thaliana
<220> FEATURE:
<221> NAME/KEY: promoter
<222> LOCATION: (1)..(1972)
<223> OTHER INFORMATION: transcription regulating sequence from
      Arabidopsis thaliana gene At5g67280

<400> SEQUENCE: 45
tataatatat ccaaaaacac ccgaccgatc aagtgacaat gcgcagtgtt gtattattat      60
attatcactg tttgaaaaat tgtcgaactc aggattggtt tataactttg caagacgata     120
ataactttgg agttttgcat aatggtaagt agaaaacgcc attttcatg catctcccgt      180
ctttgtccac cgccaaacta gtagccatcc tctaattaat aatgtattac tacagctttg     240
tatatattcg tattggagtt tacagactaa tcacatagtg gttacgttta ggaagataaa     300
acatacagaa atggtaaata gcttgtgaac ctgaatctcg aaacttacct tgtccaattt     360
gtaacatgaa tgtcgactat aagtaaattt gctctgacaa tttacagtca aactcaacta     420
tgagtctata atatcactgt agtgggtatt gttcacacac aacgattaat actgtaatta     480
atgctgaaac ttggactaca cgacactcat atgtttatt gtttcacaca cagcagaaga     540
aataattgga ttttttttcg gtccagtgat tgcactggtt tgcagaaaaa ttcttaaacg     600
ataaataaac catgttcatc tcatgattac ttaatcgttt gagaaaccgt gacatatggt     660
ggtaacaaac aaaacaaac aaataccaac cggtaaaaca tatatacagt attttataca      720
taaacaattt tgtgattttg gcaatcaaat aacaaggacc acaatgacgc tcgcgaaatt     780
taattaaaac ggggaccaat tttaatcaat ttgacccggt gtacattaat cttgacatgc     840
atttatttac gtgtgatgtt gacctcttgg tagatacagt actacattta tatatttttg     900
atgcaacaca taactgttta gtgtttttga tatttccttt ttttatcagt ctaactctcg     960
tgagtcgtga gtcgtgagtt gtgagtcgtg atccattggg attattacta cgtagtacat    1020
gttaaactac atatataagg attccataaa tatgaatcaa atcgaattct tcttatataa    1080
ctaagacatt aaatgtctac ttgcacttca ttaaaaagaa tcttctgatt ttattttgg     1140
tatatgcaaa attataactg catttaaaac agagattaga tcatgaaacg aatattattt    1200
ctgaaaaagt aggtatatct agtaatgtta atttattttt tgctaaggat atctagtaat    1260
attttatatg aaacacttgt ttttatttat gtgttttgcg cataaagtca atattataac    1320
gaatcactag attagtttta tttttatctt atagattagt ttaataagcc tatatctata    1380
agatgtacta tgatcagaga aacattaggt gtaatgagaa aacaataata aaacggtcat    1440
atataagtaa atccaagtca gtgagagacc tgcaaaaatt tcgaactttt tgtgaatgtc    1500
ttatagcaaa gatactattc tcccatctga tcatgtttcc atagatatta gttaattggc    1560
taataataca attcttcaca cacatcacat gatcgatatg cgtaatctca cgtcacaatt    1620
tccgtcataa tcaaaggag taacagaatt agtatattat atagtttctg tgatctagca    1680
aagatttaaa tgtaaacaaa actatccaga tttatatggt tttgttacgt ttctttgaag    1740
atcaatgtaa acaatgatga accaatatta gggtccacgt tgaatataaa cgtgaaaaac    1800
gacaaagcga cgtcagcata atttacgaat aggaaaacag tgttaacttt tgttatcaca    1860
ttccgtgcaa tttacatagg atatagaatt ttttatttac aaaagttata tttataaga    1920
attactcaaa tcaagaattc cataaaaaga taaacacttt catatatcgt tc             1972
```

<210> SEQ ID NO 46
<211> LENGTH: 2480
<212> TYPE: DNA
<213> ORGANISM: Arabidopsis thaliana
<220> FEATURE:
<221> NAME/KEY: CDS
<222> LOCATION: (65)..(2320)
<223> OTHER INFORMATION: encoding putative leucine-rich repeat
      transmembrane protein kinase

<400> SEQUENCE: 46

```
acaatcacat ggccttttca aaaaatcaat cttttagttc tctatcgatg cgtaggcttg          60 aagc atg atg acg aca gtc gcc gcc gat ctc cac cgt tat ctt ttc ctg         109
     Met Met Thr Thr Val Ala Ala Asp Leu His Arg Tyr Leu Phe Leu
     1               5                   10                  15 att acc gtt ttt ctt ttc ttc ctc tgc gac aaa acc tct ctt gct ctg         157
Ile Thr Val Phe Leu Phe Phe Leu Cys Asp Lys Thr Ser Leu Ala Leu
                20                  25                  30 acc aca gac ggt gtt ctt ctt ctc tct ttc cgt tac tca atc gtt gac         205
Thr Thr Asp Gly Val Leu Leu Leu Ser Phe Arg Tyr Ser Ile Val Asp
            35                  40                  45 gat cct ctt tac gtt ttt cgg agc tgg aga ttc gac gac gag act cct         253
Asp Pro Leu Tyr Val Phe Arg Ser Trp Arg Phe Asp Asp Glu Thr Pro
        50                  55                  60 tgc tct tgg cgt ggt gtc acg tgc gat gca tct tcc cgg cac gtg act         301
Cys Ser Trp Arg Gly Val Thr Cys Asp Ala Ser Ser Arg His Val Thr
65                  70                  75 gtt ctg tca ctt cca agc tcg aac ctt acc ggc aca cta cct tca aat         349
Val Leu Ser Leu Pro Ser Ser Asn Leu Thr Gly Thr Leu Pro Ser Asn
80                  85                  90                  95 ttg ggt tca ctc aat tca ctt caa aga ctt gat ctt tcc aac aat tcc         397
Leu Gly Ser Leu Asn Ser Leu Gln Arg Leu Asp Leu Ser Asn Asn Ser
                100                 105                 110 atc aat ggg tct ttc ccg gtt tcg ctt ctc aac gcg acg gag ctt cga         445
Ile Asn Gly Ser Phe Pro Val Ser Leu Leu Asn Ala Thr Glu Leu Arg
            115                 120                 125 ttt ctt gat ctg tcc gat aat cac atc tcc ggt gca cta ccg gcg agt         493
Phe Leu Asp Leu Ser Asp Asn His Ile Ser Gly Ala Leu Pro Ala Ser
        130                 135                 140 ttt ggc gcg ctt tcg aac ctc caa gtg ttg aat ctc tcc gat aat tcc         541
Phe Gly Ala Leu Ser Asn Leu Gln Val Leu Asn Leu Ser Asp Asn Ser
    145                 150                 155 ttc gtc ggc gaa tta ccg aac aca tta gga tgg aac cgg aac tta acg         589
Phe Val Gly Glu Leu Pro Asn Thr Leu Gly Trp Asn Arg Asn Leu Thr
160                 165                 170                 175 gag att tca ctt cag aaa aac tat tta tcc ggc ggg att ccg gga ggt         637
Glu Ile Ser Leu Gln Lys Asn Tyr Leu Ser Gly Gly Ile Pro Gly Gly
                180                 185                 190 ttt aag tcg acg gag tat ctt gat ctc tcg tca aat ttg atc aaa ggc         685
Phe Lys Ser Thr Glu Tyr Leu Asp Leu Ser Ser Asn Leu Ile Lys Gly
            195                 200                 205 tcg ttg ccg tca cat ttc aga ggg aat cgt cta cgc tat ttc aac gct         733
Ser Leu Pro Ser His Phe Arg Gly Asn Arg Leu Arg Tyr Phe Asn Ala
        210                 215                 220 tcg tac aac aga atc tcc ggc gag att ccg tca ggt ttc gcc gac gaa         781
Ser Tyr Asn Arg Ile Ser Gly Glu Ile Pro Ser Gly Phe Ala Asp Glu
    225                 230                 235 atc ccg gaa gac gcc acc gtt gat ctc tca ttc aac caa ctt aca ggt         829
Ile Pro Glu Asp Ala Thr Val Asp Leu Ser Phe Asn Gln Leu Thr Gly
240                 245                 250                 255
```

```
caa atc ccg ggt ttt cgg gtt ctc gat aac caa gaa tcc aac tct ttc      877
Gln Ile Pro Gly Phe Arg Val Leu Asp Asn Gln Glu Ser Asn Ser Phe
            260                 265                 270 tcc ggt aac ccg ggt ctc tgc gga tcc gac cat gca aaa cac cct tgt      925
Ser Gly Asn Pro Gly Leu Cys Gly Ser Asp His Ala Lys His Pro Cys
        275                 280                 285 cgt gac ggt gaa gca acc tct cca cct cca tcg ccg act cca aat tct      973
Arg Asp Gly Glu Ala Thr Ser Pro Pro Pro Ser Pro Thr Pro Asn Ser
    290                 295                 300 cct cct gca tta gct gct ata cca aat act att ggc tta acc aat cac     1021
Pro Pro Ala Leu Ala Ala Ile Pro Asn Thr Ile Gly Leu Thr Asn His
305                 310                 315 cca att agc tcc aaa acc ggt ccg aaa tca aaa tgg gat cat aaa ccg     1069
Pro Ile Ser Ser Lys Thr Gly Pro Lys Ser Lys Trp Asp His Lys Pro
320                 325                 330                 335 gtg ctt atc att ggc att gtt gtc ggt gac tta gcc ggt tta gca atc     1117
Val Leu Ile Ile Gly Ile Val Val Gly Asp Leu Ala Gly Leu Ala Ile
                340                 345                 350 ctc ggg att gtg ttt ttc tac att tac cag tcg aga aaa cgg aag acc     1165
Leu Gly Ile Val Phe Phe Tyr Ile Tyr Gln Ser Arg Lys Arg Lys Thr
            355                 360                 365 gta acg gct acg tca aaa tgg tcc acg tca tca aca gat tcc aag gtc     1213
Val Thr Ala Thr Ser Lys Trp Ser Thr Ser Ser Thr Asp Ser Lys Val
        370                 375                 380 tca aaa tgg tac tgt tta cgc aaa tcc gtt tac gtt gac ggt gac tgc     1261
Ser Lys Trp Tyr Cys Leu Arg Lys Ser Val Tyr Val Asp Gly Asp Cys
    385                 390                 395 gaa gaa gaa gaa gag gaa tct gag aca tcg gaa tcc gaa tcc gac gaa     1309
Glu Glu Glu Glu Glu Glu Ser Glu Thr Ser Glu Ser Glu Ser Asp Glu
400                 405                 410                 415 gag aac ccg gtc gga cca aat cga cgg tca gga tta gac gat caa gaa     1357
Glu Asn Pro Val Gly Pro Asn Arg Arg Ser Gly Leu Asp Asp Gln Glu
                420                 425                 430 aaa aag gga acg tta gtg aat ctc gat tca gag aaa gag ctt gaa atc     1405
Lys Lys Gly Thr Leu Val Asn Leu Asp Ser Glu Lys Glu Leu Glu Ile
            435                 440                 445 gaa acg ctt ctc aaa gca tca gct tat att ttg gga gcc acc ggt tcg     1453
Glu Thr Leu Leu Lys Ala Ser Ala Tyr Ile Leu Gly Ala Thr Gly Ser
        450                 455                 460 agc ata atg tat aaa gcg gtg ctt caa gac gga aca gct gtg gcg gtt     1501
Ser Ile Met Tyr Lys Ala Val Leu Gln Asp Gly Thr Ala Val Ala Val
    465                 470                 475 cga cga ata gct gaa tgc ggt tta gac cgg ttt aga gat ttc gaa gct     1549
Arg Arg Ile Ala Glu Cys Gly Leu Asp Arg Phe Arg Asp Phe Glu Ala
480                 485                 490                 495 cag gtt cga gcc gtg gct aag tta ata cat cca aac ctg gta cga att     1597
Gln Val Arg Ala Val Ala Lys Leu Ile His Pro Asn Leu Val Arg Ile
                500                 505                 510 cgc ggt ttc tat tgg gga tcc gac gag aaa ctt gtc att tac gat ttt     1645
Arg Gly Phe Tyr Trp Gly Ser Asp Glu Lys Leu Val Ile Tyr Asp Phe
            515                 520                 525 gtc cct aac ggc agc ctc gct aac gcc cgt tac cgg aaa gtg ggc tcc     1693
Val Pro Asn Gly Ser Leu Ala Asn Ala Arg Tyr Arg Lys Val Gly Ser
        530                 535                 540 tct cct tgt cat tta cct tgg gac gct cgg ctc aag ata gca aaa ggc     1741
Ser Pro Cys His Leu Pro Trp Asp Ala Arg Leu Lys Ile Ala Lys Gly
    545                 550                 555 ata gct cgc ggg cta aca tac gta cac gac aag aag tac gtg cat ggt     1789
Ile Ala Arg Gly Leu Thr Tyr Val His Asp Lys Lys Tyr Val His Gly
560                 565                 570                 575
```

-continued

```
aac ctc aag cct agc aat atc ctt ttg ggc tta gat atg gag cct aaa      1837
Asn Leu Lys Pro Ser Asn Ile Leu Leu Gly Leu Asp Met Glu Pro Lys
                580                 585                 590 gtt gcg gat ttc ggt ctt gag aag ctt ttg att ggg gac atg agt tat      1885
Val Ala Asp Phe Gly Leu Glu Lys Leu Leu Ile Gly Asp Met Ser Tyr
            595                 600                 605 aga acc ggt gga tcg gct cca ata ttc gga agc aag aga tcc aca acg      1933
Arg Thr Gly Gly Ser Ala Pro Ile Phe Gly Ser Lys Arg Ser Thr Thr
        610                 615                 620 tct ctt gag ttt ggg ccg agt cca agc cca agt cca agt tca gtc ggg      1981
Ser Leu Glu Phe Gly Pro Ser Pro Ser Pro Ser Pro Ser Ser Val Gly
    625                 630                 635 tta ccc tac aat gct cca gaa tct ctt cgg agt att aag ccg aat tcg      2029
Leu Pro Tyr Asn Ala Pro Glu Ser Leu Arg Ser Ile Lys Pro Asn Ser
640                 645                 650                 655 aaa tgg gat gtg tac tcg ttc gga gtt att ctg ctt gag cta cta acg      2077
Lys Trp Asp Val Tyr Ser Phe Gly Val Ile Leu Leu Glu Leu Leu Thr
                660                 665                 670 gga aag atc gtg gtg gtc gac gag ctt gga cag gtt aat ggg ctt gtg      2125
Gly Lys Ile Val Val Val Asp Glu Leu Gly Gln Val Asn Gly Leu Val
            675                 680                 685 att gat gac ggt gag cgg gca att cgg atg gcg gac tct gct ata cgg      2173
Ile Asp Asp Gly Glu Arg Ala Ile Arg Met Ala Asp Ser Ala Ile Arg
        690                 695                 700 gct gag tta gaa ggc aaa gaa gaa gct gtg ttg gca tgt ttg aaa atg      2221
Ala Glu Leu Glu Gly Lys Glu Glu Ala Val Leu Ala Cys Leu Lys Met
    705                 710                 715 ggc cta gct tgt gcg tct cca ata cca cag aga agg ccc aat atc aaa      2269
Gly Leu Ala Cys Ala Ser Pro Ile Pro Gln Arg Arg Pro Asn Ile Lys
720                 725                 730                 735 gag gct ttg caa gtt ctc gag aga ttc cct gtt cat tct agt caa cag      2317
Glu Ala Leu Gln Val Leu Glu Arg Phe Pro Val His Ser Ser Gln Gln
                740                 745                 750 taa tgataataat taagaccaag aaagagttaa ataacttgac tgtgtgtact           2370
tagagttaga ttgataggca agtttgatct tcttttgtgg cttctgattt tgaatttatt    2430
tttggttatg attttagtga caattatatc tctgggcttg ttacaaattt               2480
```

<210> SEQ ID NO 47
<211> LENGTH: 751
<212> TYPE: PRT
<213> ORGANISM: Arabidopsis thaliana

<400> SEQUENCE: 47

```
Met Met Thr Thr Val Ala Ala Asp Leu His Arg Tyr Leu Phe Leu Ile
1               5                   10                  15

Thr Val Phe Leu Phe Phe Leu Cys Asp Lys Thr Ser Leu Ala Leu Thr
                20                  25                  30

Thr Asp Gly Val Leu Leu Ser Phe Arg Tyr Ser Ile Val Asp Asp
            35                  40                  45

Pro Leu Tyr Val Phe Arg Ser Trp Arg Phe Asp Asp Glu Thr Pro Cys
        50                  55                  60

Ser Trp Arg Gly Val Thr Cys Asp Ala Ser Ser Arg His Val Thr Val
65                  70                  75                  80

Leu Ser Leu Pro Ser Ser Asn Leu Thr Gly Thr Leu Pro Ser Asn Leu
                85                  90                  95

Gly Ser Leu Asn Ser Leu Gln Arg Leu Asp Leu Ser Asn Asn Ser Ile
            100                 105                 110
```

-continued

```
Asn Gly Ser Phe Pro Val Ser Leu Leu Asn Ala Thr Glu Leu Arg Phe
    115                 120                 125

Leu Asp Leu Ser Asp Asn His Ile Ser Gly Ala Leu Pro Ala Ser Phe
130                 135                 140

Gly Ala Leu Ser Asn Leu Gln Val Leu Asn Leu Ser Asp Asn Ser Phe
145                 150                 155                 160

Val Gly Glu Leu Pro Asn Thr Leu Gly Trp Asn Arg Asn Leu Thr Glu
                165                 170                 175

Ile Ser Leu Gln Lys Asn Tyr Leu Ser Gly Ile Pro Gly Gly Phe
            180                 185                 190

Lys Ser Thr Glu Tyr Leu Asp Leu Ser Ser Asn Leu Ile Lys Gly Ser
            195                 200                 205

Leu Pro Ser His Phe Arg Gly Asn Arg Leu Arg Tyr Phe Asn Ala Ser
    210                 215                 220

Tyr Asn Arg Ile Ser Gly Glu Ile Pro Ser Gly Phe Ala Asp Glu Ile
225                 230                 235                 240

Pro Glu Asp Ala Thr Val Asp Leu Ser Phe Asn Gln Leu Thr Gly Gln
                245                 250                 255

Ile Pro Gly Phe Arg Val Leu Asp Asn Gln Glu Ser Asn Ser Phe Ser
            260                 265                 270

Gly Asn Pro Gly Leu Cys Gly Ser Asp His Ala Lys His Pro Cys Arg
        275                 280                 285

Asp Gly Glu Ala Thr Ser Pro Pro Ser Pro Thr Pro Asn Ser Pro
    290                 295                 300

Pro Ala Leu Ala Ala Ile Pro Asn Thr Ile Gly Leu Thr Asn His Pro
305                 310                 315                 320

Ile Ser Ser Lys Thr Gly Pro Lys Ser Lys Trp Asp His Lys Pro Val
                325                 330                 335

Leu Ile Ile Gly Ile Val Gly Asp Leu Ala Gly Leu Ala Ile Leu
            340                 345                 350

Gly Ile Val Phe Phe Tyr Ile Tyr Gln Ser Arg Lys Arg Lys Thr Val
        355                 360                 365

Thr Ala Thr Ser Lys Trp Ser Thr Ser Ser Thr Asp Ser Lys Val Ser
    370                 375                 380

Lys Trp Tyr Cys Leu Arg Lys Ser Val Tyr Val Asp Gly Asp Cys Glu
385                 390                 395                 400

Glu Glu Glu Glu Ser Glu Thr Ser Glu Ser Glu Ser Asp Glu Glu
                405                 410                 415

Asn Pro Val Gly Pro Asn Arg Arg Ser Gly Leu Asp Asp Gln Glu Lys
            420                 425                 430

Lys Gly Thr Leu Val Asn Leu Asp Ser Glu Lys Glu Leu Glu Ile Glu
        435                 440                 445

Thr Leu Leu Lys Ala Ser Ala Tyr Ile Leu Gly Ala Thr Gly Ser Ser
    450                 455                 460

Ile Met Tyr Lys Ala Val Leu Gln Asp Gly Thr Ala Val Ala Val Arg
465                 470                 475                 480

Arg Ile Ala Glu Cys Gly Leu Asp Arg Phe Arg Asp Phe Glu Ala Gln
                485                 490                 495

Val Arg Ala Val Ala Lys Leu Ile His Pro Asn Leu Val Arg Ile Arg
            500                 505                 510

Gly Phe Tyr Trp Gly Ser Asp Glu Lys Leu Val Ile Tyr Asp Phe Val
        515                 520                 525
```

```
Pro Asn Gly Ser Leu Ala Asn Ala Arg Tyr Arg Lys Val Gly Ser Ser
        530                 535                 540
Pro Cys His Leu Pro Trp Asp Ala Arg Leu Lys Ile Ala Lys Gly Ile
545                 550                 555                 560
Ala Arg Gly Leu Thr Tyr Val His Asp Lys Tyr Val His Gly Asn
                565                 570                 575
Leu Lys Pro Ser Asn Ile Leu Leu Gly Leu Asp Met Glu Pro Lys Val
        580                 585                 590
Ala Asp Phe Gly Leu Glu Lys Leu Leu Ile Gly Asp Met Ser Tyr Arg
        595                 600                 605
Thr Gly Gly Ser Ala Pro Ile Phe Gly Ser Lys Arg Ser Thr Thr Ser
        610                 615                 620
Leu Glu Phe Gly Pro Ser Pro Ser Pro Ser Ser Val Gly Leu
625                 630                 635                 640
Pro Tyr Asn Ala Pro Glu Ser Leu Arg Ser Ile Lys Pro Asn Ser Lys
                645                 650                 655
Trp Asp Val Tyr Ser Phe Gly Val Ile Leu Leu Glu Leu Leu Thr Gly
                660                 665                 670
Lys Ile Val Val Asp Glu Leu Gly Gln Val Asn Gly Leu Val Ile
        675                 680                 685
Asp Asp Gly Glu Arg Ala Ile Arg Met Ala Asp Ser Ala Ile Arg Ala
        690                 695                 700
Glu Leu Glu Gly Lys Glu Glu Ala Val Leu Ala Cys Leu Lys Met Gly
705                 710                 715                 720
Leu Ala Cys Ala Ser Pro Ile Pro Gln Arg Arg Pro Asn Ile Lys Glu
                725                 730                 735
Ala Leu Gln Val Leu Glu Arg Phe Pro Val His Ser Ser Gln Gln
        740                 745                 750

<210> SEQ ID NO 48
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 48
gaccatacta gtgtccttga aaatcag                                     27

<210> SEQ ID NO 49
<211> LENGTH: 25
<212> TYPE: DNA
<213> ORGANISM: Artificial Sequence
<220> FEATURE:
<223> OTHER INFORMATION: oligonuceotide primer

<400> SEQUENCE: 49
ccctcgccat ggttagctaa ttagg                                       25

<210> SEQ ID NO 50
<211> LENGTH: 25
<212> TYPE: DNA
<213> ORGANISM: Artificial Sequence
<220> FEATURE:
<223> OTHER INFORMATION: oligonuceotide primer

<400> SEQUENCE: 50
gacgggacta gtcacacatc gaagc                                       25
```

```
<210> SEQ ID NO 51
<211> LENGTH: 25
<212> TYPE: DNA
<213> ORGANISM: Artificial Sequence
<220> FEATURE:
<223> OTHER INFORMATION: oligonuceotide primer

<400> SEQUENCE: 51
ccctcgccat ggttagctaa ttagg                                          25

<210> SEQ ID NO 52
<211> LENGTH: 30
<212> TYPE: DNA
<213> ORGANISM: Artificial Sequence
<220> FEATURE:
<223> OTHER INFORMATION: oligonuceotide primer

<400> SEQUENCE: 52
tccaccggat cctcaattat taaaaaaata                                     30

<210> SEQ ID NO 53
<211> LENGTH: 25
<212> TYPE: DNA
<213> ORGANISM: Artificial Sequence
<220> FEATURE:
<223> OTHER INFORMATION: oligonuceotide primer

<400> SEQUENCE: 53
ccctcgccat ggttagctaa ttagg                                          25

<210> SEQ ID NO 54
<211> LENGTH: 24
<212> TYPE: DNA
<213> ORGANISM: Artificial Sequence
<220> FEATURE:
<223> OTHER INFORMATION: oligonuceotide primer

<400> SEQUENCE: 54
ttctcagaat tctctccttt gccc                                           24

<210> SEQ ID NO 55
<211> LENGTH: 24
<212> TYPE: DNA
<213> ORGANISM: Artificial Sequence
<220> FEATURE:
<223> OTHER INFORMATION: oligonuceotide primer

<400> SEQUENCE: 55
cacctcccat ggtttctcaa tcag                                           24

<210> SEQ ID NO 56
<211> LENGTH: 30
<212> TYPE: DNA
<213> ORGANISM: Artificial Sequence
<220> FEATURE:
<223> OTHER INFORMATION: oligonuceotide primer

<400> SEQUENCE: 56
aaaaaaccat ggccttatag gtatttatac                                     30

<210> SEQ ID NO 57
<211> LENGTH: 26
<212> TYPE: DNA
<213> ORGANISM: Artificial Sequence
<220> FEATURE:
<223> OTHER INFORMATION: oligonuceotide primer
```

<400> SEQUENCE: 57
ccctgaggat ccgctgagca aaagtc                                    26

<210> SEQ ID NO 58
<211> LENGTH: 24
<212> TYPE: DNA
<213> ORGANISM: Artificial Sequence
<220> FEATURE:
<223> OTHER INFORMATION: oligonuceotide primer

<400> SEQUENCE: 58
cacctcccat ggtttctcaa tcag                                      24

<210> SEQ ID NO 59
<211> LENGTH: 30
<212> TYPE: DNA
<213> ORGANISM: Artificial Sequence
<220> FEATURE:
<223> OTHER INFORMATION: oligonuceotide primer

<400> SEQUENCE: 59
aaaaaaccat ggccttatag gtatttatac                                30

<210> SEQ ID NO 60
<211> LENGTH: 24
<212> TYPE: DNA
<213> ORGANISM: Artificial Sequence
<220> FEATURE:
<223> OTHER INFORMATION: oligonuceotide primer

<400> SEQUENCE: 60
aaatgagaat tcccaaaaac aagc                                      24

<210> SEQ ID NO 61
<211> LENGTH: 25
<212> TYPE: DNA
<213> ORGANISM: Artificial Sequence
<220> FEATURE:
<223> OTHER INFORMATION: oligonuceotide primer

<400> SEQUENCE: 61
aagaatccat ggggatggaa aaatg                                     25

<210> SEQ ID NO 62
<211> LENGTH: 28
<212> TYPE: DNA
<213> ORGANISM: Artificial Sequence
<220> FEATURE:
<223> OTHER INFORMATION: oligonuceotide primer

<400> SEQUENCE: 62
ggaagaccat ggaagagggg agaagaag                                  28

<210> SEQ ID NO 63
<211> LENGTH: 25
<212> TYPE: DNA
<213> ORGANISM: Artificial Sequence
<220> FEATURE:
<223> OTHER INFORMATION: oligonuceotide primer

<400> SEQUENCE: 63
aattttggat ccctttttg gcggg                                      25

```
<210> SEQ ID NO 64
<211> LENGTH: 25
<212> TYPE: DNA
<213> ORGANISM: Artificial Sequence
<220> FEATURE:
<223> OTHER INFORMATION: oligonuceotide primer

<400> SEQUENCE: 64
aagaatccat ggggatggaa aaatg                                         25

<210> SEQ ID NO 65
<211> LENGTH: 28
<212> TYPE: DNA
<213> ORGANISM: Artificial Sequence
<220> FEATURE:
<223> OTHER INFORMATION: oligonuceotide primer

<400> SEQUENCE: 65
ggaagaccat ggaagagggg agaagaag                                      28

<210> SEQ ID NO 66
<211> LENGTH: 23
<212> TYPE: DNA
<213> ORGANISM: Artificial Sequence
<220> FEATURE:
<223> OTHER INFORMATION: oligonuceotide primer

<400> SEQUENCE: 66
ataatcacta gtatatgttt ttg                                           23

<210> SEQ ID NO 67
<211> LENGTH: 24
<212> TYPE: DNA
<213> ORGANISM: Artificial Sequence
<220> FEATURE:
<223> OTHER INFORMATION: oligonuceotide primer

<400> SEQUENCE: 67
gtgtagccat ggaatttgga aatg                                          24

<210> SEQ ID NO 68
<211> LENGTH: 29
<212> TYPE: DNA
<213> ORGANISM: Artificial Sequence
<220> FEATURE:
<223> OTHER INFORMATION: oligonuceotide primer

<400> SEQUENCE: 68
ggaaccatgg ctttcaagtg aggttcatt                                     29

<210> SEQ ID NO 69
<211> LENGTH: 25
<212> TYPE: DNA
<213> ORGANISM: Artificial Sequence
<220> FEATURE:
<223> OTHER INFORMATION: oligonuceotide primer

<400> SEQUENCE: 69
taatacacta gttttgtagg ttaac                                         25

<210> SEQ ID NO 70
<211> LENGTH: 24
<212> TYPE: DNA
<213> ORGANISM: Artificial Sequence
<220> FEATURE:
<223> OTHER INFORMATION: oligonuceotide primer
```

```
<400> SEQUENCE: 70
gtgtagccat ggaatttgga aatg                                          24

<210> SEQ ID NO 71
<211> LENGTH: 29
<212> TYPE: DNA
<213> ORGANISM: Artificial Sequence
<220> FEATURE:
<223> OTHER INFORMATION: oligonuceotide primer

<400> SEQUENCE: 71
ggaaccatgg ctttcaagtg aggttcatt                                     29

<210> SEQ ID NO 72
<211> LENGTH: 26
<212> TYPE: DNA
<213> ORGANISM: Artificial Sequence
<220> FEATURE:
<223> OTHER INFORMATION: oligonuceotide primer

<400> SEQUENCE: 72
ccattgggat ccttactacg tagtac                                        26

<210> SEQ ID NO 73
<211> LENGTH: 25
<212> TYPE: DNA
<213> ORGANISM: Artificial Sequence
<220> FEATURE:
<223> OTHER INFORMATION: oligonuceotide primer

<400> SEQUENCE: 73
tcgtcaccat ggttcaagcc tacgc                                         25

<210> SEQ ID NO 74
<211> LENGTH: 32
<212> TYPE: DNA
<213> ORGANISM: Artificial Sequence
<220> FEATURE:
<223> OTHER INFORMATION: oligonuceotide primer

<400> SEQUENCE: 74
gaacgaccat ggaaagtgtt tatcttttta tg                                 32

<210> SEQ ID NO 75
<211> LENGTH: 27
<212> TYPE: DNA
<213> ORGANISM: Artificial Sequence
<220> FEATURE:
<223> OTHER INFORMATION: oligonuceotide primer

<400> SEQUENCE: 75
tataatggat ccaaaaacac ccgaccg                                       27

<210> SEQ ID NO 76
<211> LENGTH: 25
<212> TYPE: DNA
<213> ORGANISM: Artificial Sequence
<220> FEATURE:
<223> OTHER INFORMATION: oligonuceotide primer

<400> SEQUENCE: 76
tcgtcaccat ggttcaagcc tacgc                                         25
```

<210> SEQ ID NO 77
<211> LENGTH: 32
<212> TYPE: DNA
<213> ORGANISM: Artificial Sequence
<220> FEATURE:
<223> OTHER INFORMATION: oligonuceotide primer

<400> SEQUENCE: 77

| gaacgaccat ggaaagtgtt tatctttta tg | 32 |
|---|---|

<210> SEQ ID NO 78
<211> LENGTH: 8986
<212> TYPE: DNA
<213> ORGANISM: Artificial Sequence
<220> FEATURE:
<223> OTHER INFORMATION: binary vector pSUN0301

<400> SEQUENCE: 78

| cgttgtaaaa cgacggccag tgaattcgag ctcggtacct cgagcccggg cgatatcgga | 60 |
|---|---|
| tccactagtc tagagtcgat cgaccatggt acgtcctgta gaaacccaa cccgtgaaat | 120 |
| caaaaaactc gacggcctgt gggcattcag tctggatcgc gaaaactgtg aattggtca | 180 |
| gcgttggtgg gaaagcgcgt tacaagaaag ccgggcaatt gctgtgccag cagttttaa | 240 |
| cgatcagttc gccgatgcag atattcgtaa ttatgcgggc aacgtctggt atcagcgcga | 300 |
| agtctttata ccgaaaggtt gggcaggcca gcgtatcgtg ctgcgtttcg atgcggtcac | 360 |
| tcattacggc aaagtgtggg tcaataatca ggaagtgatg gagcatcagg gcggctatac | 420 |
| gccatttgaa gccgatgtca cgccgtatgt tattgccggg aaaagtgtac gtaagtttct | 480 |
| gcttctacct ttgatatata taataatt atcattaatt agtagtaata taatatttca | 540 |
| aatattttt tcaaaataaa agaatgtagt atatagcaat tgcttttctg tagtttataa | 600 |
| gtgtgtatat tttaatttat aacttttcta atatatgacc aaaatttgtt gatgtgcagg | 660 |
| tatcaccgtt tgtgtgaaca acgaactgaa ctggcagact atcccgccgg gaatggtgat | 720 |
| taccgacgaa acggcaaga aaagcagtc ttacttccat gatttcttta actatgccgg | 780 |
| aatccatcgc agcgtaatgc tctacaccac gccgaacacc tgggtggacg atatcaccgt | 840 |
| ggtgacgcat gtcgcgcaag actgtaacca cgcgtctgtt gactggcagg tggtggccaa | 900 |
| tggtgatgtc agcgttgaac tgcgtgatgc ggatcaacag gtggttgcaa ctggacaagg | 960 |
| cactagcggg actttgcaag tggtgaatcc gcacctctgg caaccgggtg aaggttatct | 1020 |
| ctatgaactg tgcgtcacag ccaaaagcca gacagagtgt gatatctacc cgcttcgcgt | 1080 |
| cggcatccgg tcagtggcag tgaagggcga acagttcctg attaaccaca accgttcta | 1140 |
| ctttactggc tttggtcgtc atgaagatgc ggacttacgt ggcaaggat tcgataacgt | 1200 |
| gctgatggtg cacgaccacg cattaatgga ctggattggg gccaactcct accgtacctc | 1260 |
| gcattaccct tacgctgaag agatgctcga ctgggcagat gaacatggca tcgtggtgat | 1320 |
| tgatgaaact gctgctgtcg gctttaacct ctctttaggc attggtttcg aagcgggcaa | 1380 |
| caagccgaaa gaactgtaca gcgaagaggc agtcaacggg gaaactcagc aagcgcactt | 1440 |
| acaggcgatt aaagagctga tagcgcgtga caaaaaccac ccaagcgtgg tgatgtggag | 1500 |
| tattgccaac gaaccggata cccgtccgca agtgcacggg aatatttcgc cactggcgga | 1560 |
| agcaacgcgt aaactcgacc cgacgcgtcc gatcacctgc gtcaatgtaa tgttctgcga | 1620 |
| cgctcacacc gataccatca gcgatctctt tgatgtgctg tgcctgaacc gttattacgg | 1680 |
| atggtatgtc caaagcggcg atttggaaac ggcagagaag gtactggaaa agaacttct | 1740 |

```
ggcctggcag gagaaactgc atcagccgat tatcatcacc gaatacgcg tggatacgtt    1800 agccgggctg cactcaatgt acaccgacat gtggagtgaa gagtatcagt gtgcatggct    1860
ggatatgtat caccgcgtct ttgatcgcgt cagcgccgtc gtcggtgaac aggtatggaa    1920
tttcgccgat tttgcgacct cgcaaggcat attgcgcgtt ggcggtaaca agaaagggat    1980
cttcactcgc gaccgcaaac cgaagtcggc ggcttttctg ctgcaaaaac gctggactgg    2040
catgaacttc ggtgaaaaac cgcagcaggg aggcaaacaa tgaatcaaca actctcctgg    2100
cgcaccatcg tcggctacag cctcgggaat tgctaccgag ctcggtaccc ggcgcaaaaa    2160
tcaccagtct ctctctacaa atctatctct ctctattttt ctccagaata atgtgtgagt    2220
agttcccaga taagggaatt agggttctta tagggtttcg ctcatgtgtt gagcatataa    2280 gaaacccctta gtatgtattt gtatttgtaa aatacttcta tcaataaaat ttctaattcc    2340
taaaaccaaa atccagtgac cgggtaccga gctcgaattt cgacctgcag gcatgcaagc    2400
ttggcgtaat catggtcata gctgtttcct actagatctg attgtcgttt cccgccttca    2460
gtttaaacta tcagtgtttg acaggatata ttggcgggta aacctaagag aaaagagcgt    2520
ttattagaat aatcggatat ttaaaagggc gtgaaaaggt ttatccgttc gtccatttgt    2580
atgtccatga taagtcgcgc tgtatgtgtt tgtttgaata ttcatggaac gcagtggcgg    2640
ttttcatggc ttgttatgac tgttttttg gggtacagtc tatgcctcgg gcatccaagc    2700
agcaagcgcg ttacgccgtg ggtcgatgtt tgatgttatg gagcagcaac gatgttacgc    2760
agcagggcag tcgccctaaa acaaagttaa acatcatggg ggaagcggtg atcgccgaag    2820
tatcgactca actatcagag gtagttggcg tcatcgagcg ccatctcgaa ccgacgttgc    2880
tggccgtaca tttgtacggc tccgcagtgg atggcggcct gaagccacac agtgatattg    2940
atttgctggt tacggtgacc gtaaggcttg atgaaacaac gcggcgagct ttgatcaacg    3000
accttttgga aacttcggct tcccctggag agagcgagat tctccgcgct gtagaagtca    3060
ccattgttgt gcacgacgac atcattccgt ggcgttatcc agctaagcgc gaactgcaat    3120
ttggagaatg gcagcgcaat gacattcttg caggtatctt cgagccagcc acgatcgaca    3180
ttgatctggc tatcttgctg acaaaagcaa gagaacatag cgttgccttg gtaggtccag    3240
cggcggagga actctttgat ccggttcctg aacaggatct atttgaggcg ctaaatgaaa    3300
ccttaacgct atggaactcg ccgcccgact gggctggcga tgagcgaaat gtagtgctta    3360
cgttgtcccg catttggtac agcgcagtaa ccggcaaaat cgcgccgaag gatgtcgctg    3420
ccgactgggc aatggagcgc ctgccggccc agtatcagcc cgtcatactt gaagctagac    3480
aggcttatct tggacaagaa gaagatcgct tggcctcgcg cgcagatcag ttggaagaat    3540
ttgtccacta cgtgaaaggc gagatcacca aggtagtcgg caaataatgt ctagctagaa    3600
attcgttcaa gccgacgccg cttcgcggcg cggcttaact caagcgttag atgcactaag    3660
cacataattg ctcacagcca aactatcagg tcaagtctgc ttttattatt tttaagcgtg    3720
cataataagc cctacacaaa ttgggagata tatcatgcat gaccaaaatc ccttaacgtg    3780
agttttcgtt ccactgagcg tcagaccccg tagaaaagat caaaggatct tcttgagatc    3840
ctttttttct gcgcgtaatc tgctgcttgc aaacaaaaaa accaccgcta ccagcggtgg    3900
tttgtttgcc ggatcaagag ctaccaactc tttttccgaa ggtaactggc ttcagcagag    3960
cgcagatacc aaatactgtc cttctagtgt agccgtagtt aggccaccac ttcaagaact    4020
ctgtagcacc gcctacatac ctcgctctgc taatcctgtt accagtggct gctgccagtg    4080
gcgataagtc gtgtcttacc gggttggact caagacgata gttaccggat aaggcgcagc    4140
```

```
ggtcgggctg aacgggggt tcgtgcacac agcccagctt ggagcgaacg acctacaccg    4200
aactgagata cctacagcgt gagctatgag aaagcgccac gcttcccgaa gggagaaagg    4260
cggacaggta tccggtaagc ggcagggtcg gaacaggaga gcgcacgagg gagcttccag    4320
ggggaaacgc ctggtatctt tatagtcctg tcgggtttcg ccacctctga cttgagcgtc    4380
gattttgtg atgctcgtca gggggcgga gcctatggaa aaacgccagc aacgcggcct    4440
ttttacggtt cctggccttt tgctggcctt ttgctcacat gttctttcct gcgttatccc    4500
ctgattctgt ggataaccgt attaccgcct ttgagtgagc tgataccgct cgccgcagcc    4560
gaacgaccga gcgcagcgag tcagtgagcg aggaagcgga agagcgcctg atgcggtatt    4620
ttctccttac gcatctgtgc ggtatttcac accgcatagg ccgcgatagg ccgacgcgaa    4680
gcggcgggc gtagggagcg cagcgaccga agggtaggcg ctttttgcag ctcttcggct    4740
gtgcgctggc cagacagtta tgcacaggcc aggcgggttt taagagtttt aataagtttt    4800
aaagagtttt aggcggaaaa atcgcctttt ttctcttta tatcagtcac ttacatgtgt    4860
gaccggttcc caatgtacgg ctttgggttc ccaatgtacg ggttccggtt cccaatgtac    4920
ggctttgggt tcccaatgta cgtgctatcc acaggaaaga ccttttcg acctttttcc    4980
cctgctaggg caatttgccc tagcatctgc tccgtacatt aggaaccggc ggatgcttcg    5040
ccctcgatca ggttgcggta gcgcatgact aggatcgggc cagcctgccc cgcctcctcc    5100
ttcaaatcgt actccggcag gtcatttgac ccgatcagct tgcgcacggt gaaacagaac    5160
ttcttgaact ctccggcgct gccactgcgt tcgtagatcg tcttgaacaa ccatctggct    5220
tctgccttgc ctgcggcgcg gcgtgccagg cggtagagaa aacggccgat gccgggatcg    5280
atcaaaaagt aatcggggtg aaccgtcagc acgtccgggt tcttgccttc tgtgatctcg    5340
cggtacatcc aatcagctag ctcgatctcg atgtactccg gccgcccggt ttcgctcttt    5400
acgatcttgt agcggctaat caaggcttca ccctcggata ccgtcaccag gcggccgttc    5460
ttggccttct tcgtacgctg catggcaacg tgcgtggtgt ttaaccgaat gcaggtttct    5520
accaggtcgt ctttctgctt tccgccatcg gctcgccggc agaacttgag tacgtccgca    5580
acgtgtggac ggaacacgcg gccgggcttg tctcccttcc cttcccggta tcggttcatg    5640
gattcggtta gatgggaaac cgccatcagt accaggtcgt aatcccacac actggccatg    5700
ccggccggcc ctgcggaaac ctctacgtgc ccgtctggaa gctcgtagcg gatcacctcg    5760
ccagctcgtc ggtcacgctt cgacagacgg aaaacggcca cgtccatgat gctgcgacta    5820
tcgcgggtgc ccacgtcata gagcatcgga acgaaaaaat ctggttgctc gtcgcccttg    5880
ggcggcttcc taatcgacgg cgcaccggct gccggcggtt gccgggattc tttgcggatt    5940
cgatcagcgg ccccttgcca cgattcaccg gggcgtgctt ctgcctcgat gcgttgccgc    6000
tgggcggcct gcgcggcctt caacttctcc accaggtcat cacccagcgc cgcgccgatt    6060
tgtaccgggc cggatggttt gcgaccgctc acgccgattc ctcgggcttg ggggttccag    6120
tgccattgca gggccggcag acaacccagc cgcttacgcc tggccaaccg cccgttcctc    6180
cacacatggg gcattccacg gcgtcggtgc ctggttgttc ttgattttcc atgccgcctc    6240
ctttagccgc taaaattcat ctactcattt attcatttgc tcatttactc tggtagctgc    6300
gcgatgtatt cagatagcag ctcggtaatg gtcttgcctt ggcgtaccgc gtacatcttc    6360
agcttggtgt gatcctccgc cggcaactga agttgacccc gcttcatggc tggcgtgtct    6420
gccaggctgg ccaacgttgc agccttgctg ctgcgtgcgc tcggacggcc ggcacttagc    6480
gtgtttgtgc ttttgctcat tttctcttta cctcattaac tcaaatgagt tttgatttaa    6540
```

```
tttcagcggc cagcgcctgg acctcgcggg cagcgtcgcc ctcgggttct gattcaagaa    6600
cggttgtgcc ggcggcggca gtgcctgggt agctcacgcg ctgcgtgata cgggactcaa    6660
gaatgggcag ctcgtacccg ccagcgcct  cggcaacctc accgccgatg cgcgtgcctt    6720
tgatcgcccg cgacacgaca aaggccgctt gtagccttcc atccgtgacc tcaatgcgct    6780
gcttaaccag ctccaccagg tcggcggtgg cccatatgtc gtaagggctt ggctgcaccg    6840
gaatcagcac gaagtcggct gccttgatcg cggacacagc caagtccgcc gcctggggcg    6900
ctccgtcgat cactacgaag tcgcgccggc cgatggcctt cacgtcgcgg tcaatcgtcg    6960
ggcggtcgat gccgacaacg gttagcggtt gatcttcccg cacggccgcc caatcgcggg    7020
cactgccctg gggatcggaa tcgactaaca gaacatcggc ccggcgagt  tgcagggcgc    7080
gggctagatg ggttgcgatg gtcgtcttgc ctgacccgcc tttctggtta agtacagcga    7140
taaccttcat gcgttcccct tgcgtatttg tttatttact catcgcatca tatacgcagc    7200
gaccgcatga cgcaagctgt tttactcaaa tacacatcac cttttagac  gcgtggtgat    7260
tttgtgccga gctgccggtc ggggagctgt tggctggctg gtggcaggat atattgtggt    7320
gtaaacaaat tgacgcttag acaacttaat aacacattgc ggacgtcttt aatgtactga    7380
attaacatcc gtttgatact tgtctaaaat tggctgattt cgagtgcatc tatgcataaa    7440
aacaatctaa tgacaattat taccaagcag tgatcctgtc aaacactgat agtttaaact    7500
gaaggcggga aacgacaatc tgatcatgag cggagaatta agggagtcac gttatgaccc    7560
ccgccgatga cgcgggacaa gccgttttac gtttggaact gacagaaccg caacgttgaa    7620
ggagccactc agccgcgggt ttctggagtt taatgagcta agcacatacg tcagaaacca    7680
ttattgcgcg ttcaaaagtc gcctaaggtc actatcagct agcaaatatt tcttgtcaaa    7740
aatgctccac tgacgttcca taaattcccc tcggtatcca attagagtct catattcact    7800
ctcaatccaa ataatctgca ccggatctgg atcgtttcgc atgattgaac aagatggatt    7860
gcacgcaggt tctccggccg cttgggtgga gaggctattc ggctatgact gggcacaaca    7920
gacaatcggc tgctctgatg ccgccgtgtt ccggctgtca gcgcaggggc gcccggttct    7980
ttttgtcaag accgacctgt ccggtgccct gaatgaactg caggacgagg cagcgcggct    8040
atcgtggctg gccacgacgg gcgttccttg cgcagctgtg ctcgacgttg tcactgaagc    8100
gggaagggac tggctgctat tgggcgaagt gccggggcag gatctcctgt catctcacct    8160
tgctcctgcc gagaaagtat ccatcatggc tgatgcaatg cggcggctgc atacgcttga    8220
tccggctacc tgcccattcg accaccaagc gaaacatcgc atcgagcgag cacgtactcg    8280
gatggaagcc ggtcttgtcg atcaggatga tctggacgaa gagcatcagg gctcgcgcc   8340
agccgaactg ttcgccaggc tcaaggcgcg catgcccgac ggcgaggatc tcgtcgtgac    8400
acatggcgat gcctgcttgc cgaatatcat ggtggaaaat ggccgctttt ctggattcat    8460
cgactgtggc cggctgggtg tggcggaccg ctatcaggac atagcgttgg ctacccgtga    8520
tattgctgaa gagcttggcg gcgaatgggc tgaccgcttc ctcgtgcttt acggtatcgc    8580
cgctcccgat tcgcagcgca tcgccttcta tcgccttctt gacgagttct tctgagcggg    8640
acccaagctc tagatcttgc tgcgttcgga tattttcgtg gagttcccgc cacagacccg    8700
gatgatcccc gatcgttcaa acatttggca ataaagtttc ttaagattga atcctgttgc    8760
cggtcttgcg atgattatca tataatttct gttgaattac gttaagcatg taataattaa    8820
catgtaatgc atgacgttat ttatgagatg gttttttatg attagagtcc cgcaattata    8880
```

```
catttaatac gcgatagaaa acaaaatata gcgcgcaaac taggataaat tatcgcgcgc    8940
ggtgtcatct atgttactag atcgggcctc ctgtcaagct ctgagt                   8986
```